(12) United States Patent
Sinha

(10) Patent No.: US 10,968,477 B2
(45) Date of Patent: *Apr. 6, 2021

(54) METHOD FOR GENETIC DETECTION USING INTERSPERSED GENETIC ELEMENTS: A MULTIPLEXED DNA ANALYSIS SYSTEM

(71) Applicant: Life Genetics Lab, LLC, New Orleans, LA (US)

(72) Inventor: Sudhir Sinha, New Orleans, LA (US)

( * ) Notice: Subject to any disclaimer, the term of this patent is extended or adjusted under 35 U.S.C. 154(b) by 274 days.

This patent is subject to a terminal disclaimer.

(21) Appl. No.: 14/923,295

(22) Filed: Oct. 26, 2015

(65) Prior Publication Data
US 2016/0108462 A1  Apr. 21, 2016

Related U.S. Application Data

(63) Continuation-in-part of application No. 14/054,680, filed on Oct. 15, 2013, now Pat. No. 10,004,561.

(60) Provisional application No. 62/068,337, filed on Oct. 24, 2014, provisional application No. 61/714,088, filed on Oct. 15, 2012.

(51) Int. Cl.
| | |
|---|---|
| *C12Q 1/68* | (2018.01) |
| *C12Q 1/686* | (2018.01) |
| *C12Q 1/6874* | (2018.01) |
| *G16B 25/00* | (2019.01) |
| *A61B 18/24* | (2006.01) |

(52) U.S. Cl.
CPC ............ *C12Q 1/686* (2013.01); *A61B 18/245* (2013.01); *C12Q 1/6874* (2013.01); *G16B 25/00* (2019.02)

(58) Field of Classification Search
None
See application file for complete search history.

(56) References Cited

PUBLICATIONS

ScienceDirect, Next Generation Sequencing, available at https://www.sciencedirect.com/topics/medicine-and-dentistry/next-generation-sequencing, accessed Dec. 10, 2019.*

(Continued)

*Primary Examiner* — Aaron A Priest
(74) *Attorney, Agent, or Firm* — Stonebridge IP, PLLC

(57) ABSTRACT

By utilizing a Mini-Primer strategy targeting the target site duplication (TSD) sequence of retrotransposons, insertion and null allele (INNUL) markers, which include short interspersed nuclear elements (SINEs), long interspersed nuclear elements (LINEs), and composite SVA retrotransposons (SINE/VNTR/Alu, where VNTR represents "variable number of tandem repeats" and Alu represents a type of primate specific SINE that has reached a copy number in excess of one million in the human genome), can be effectively used as markers for human identification and bio-ancestry studies regardless of the size of the inserted element. The size of the amplicons for INNULs and the difference between allelic states can be reduced substantially such that these markers have utility for analyzing high and low quality human DNA samples. Multiplexes including either 15 or 20 retrotransposable element (RE) markers plus Amelogenin for single tube amplification of DNA in four color detection were successfully designed. The multiplexes provided power of discrimination suitable for forensic and paternity analyses.

29 Claims, 15 Drawing Sheets
(8 of 15 Drawing Sheet(s) Filed in Color)
Specification includes a Sequence Listing.

(56) References Cited

PUBLICATIONS https://en.wikipedia.org/wiki/Race_and_ethnicity_in_the_United_States, accessed Dec. 10, 2019.*

* cited by examiner

*Alu*

LINE1

SVA

FIG. 3A

Filled Site Reaction of marker Ya5ac2305:

CAAACTATGGTATAATCTTCTAATTGTCTCATTATAAAGTATTCTATTCTATAGGACAGGTAATAATCCAGAA
AATGAAACTAAGATGATCAAAACCTGTAGTTAATACTTTAAATACAATCCAACACCATTTAATC*TCTGAGTTG*
*GTGACACTCCA*ATTTCTCTCTCTAACGTTTCCTTAGACTGTAT[...]ACGGGTA
ATCCAGCACTTGGAGGCGAGCGGGGGATCATGAGGATGTAGAGATCGCGCCTGTAACGCTACTTGGA
AACCCGTCTACTAAATACAAATTACGCGCTGGACCTACAGTGAGCGGCCCTGAGCACTGACTCGAG
GCTGAGCAGAGATGCGGTGAACCTGGACGTACAGTGAGGCTACAAAAAAAAAAAAAAAAAAAAA
CCTGGGACGCGACTGCTCTCAAAAAAAAAAAAAAAAAAAAAAAAAAAG*AAGACTTGTATTCAAGGAT*
*GCCTGGGTAAGAC*GCTGGGTTTGGTTTTGGTACTTAGTCTTTGGTAATTCATTTAGCACCACTGAATTATCATTA
GTGCTTAAGAGCTGCCTTTGTGATAGAATGAATTATACATTCATCATTTTGTCTCTACTGATACAT
TAAGGAGTGGAGATACAATATTTCATCCAATAGGTCACAATGCATATAATTGCTGACATTT

SEQ ID NO: 296

FIG. 3B

Empty site Reaction of marker of Ya5ac2305:

CAAACTATGGTATAATCTTCTAATTGTCTCATTATAAAGTATTCTATTCTATAGGACAGGTAATAATCCAGAA
AATGAAACTAAGATGATCAAAACCTGTAGTTAATACTTTAAATACAATCCAACACCATTTAATCTCTGAGTTG
GTGACACTCCAATTTCTCTCTAACGTTTCCTTA*ACGTTTATTC*AAGGATGCCTGGTAAGACTGGGTTTG
GTTTGGTACTTAGTCTTTGGTAATTCATTTAGCACCACTGAATTATCATTAGTGCTTAAGAGCTGCCTTT
GTGATAGAATGAATTATACATTCATCATTTGTCTCTACTGATACATTTCATCCAATAGGTCACATATAATTGCTGACATTT

SEQ ID NO: 297

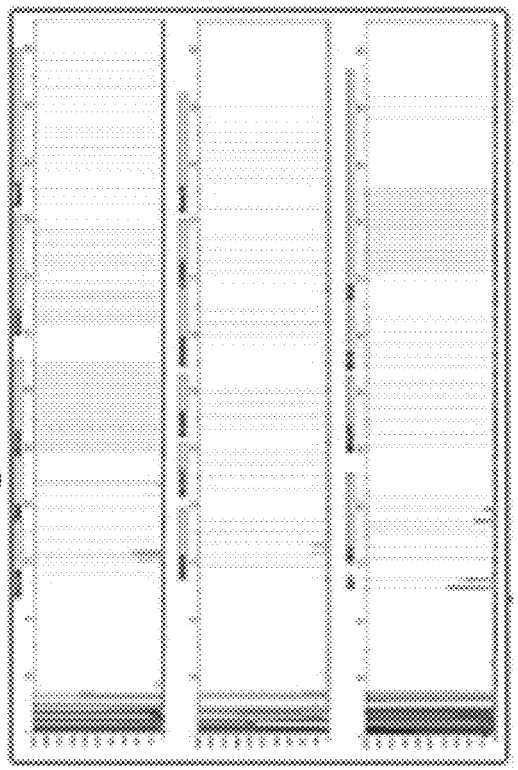
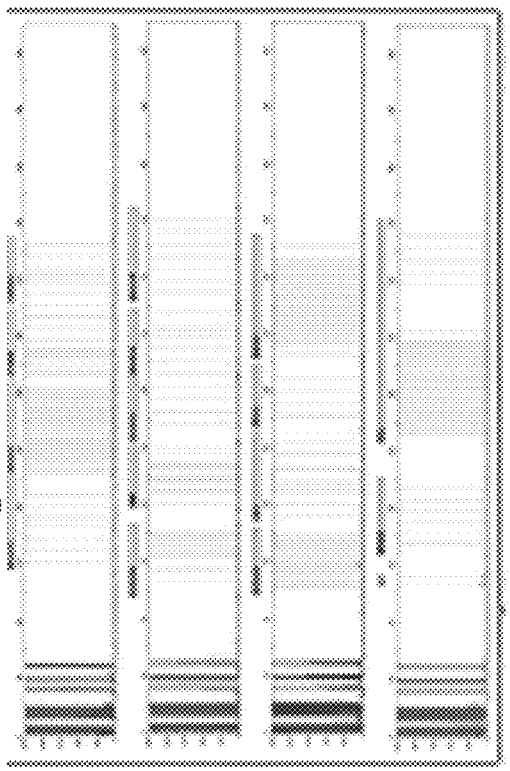
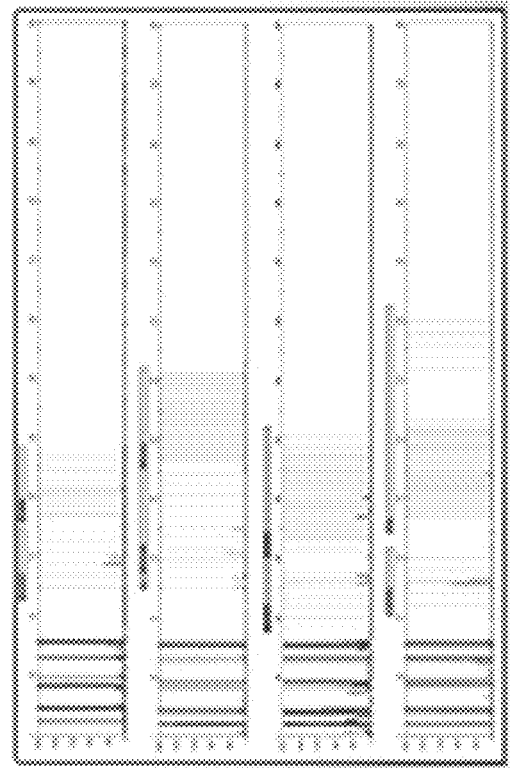
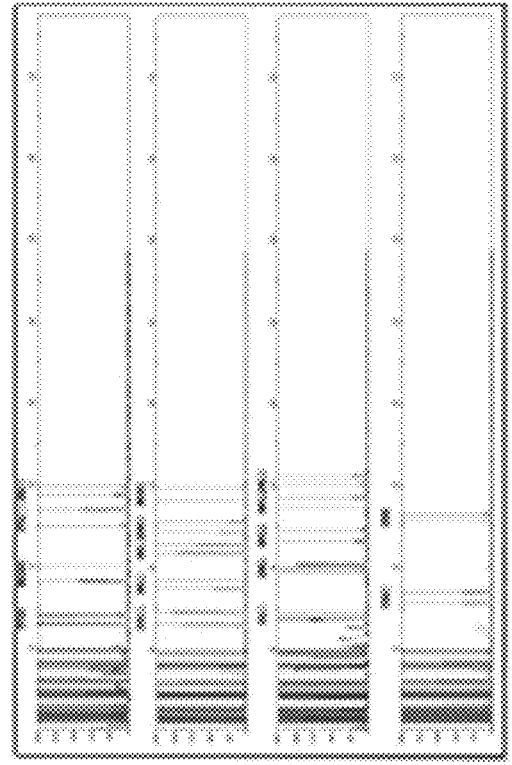

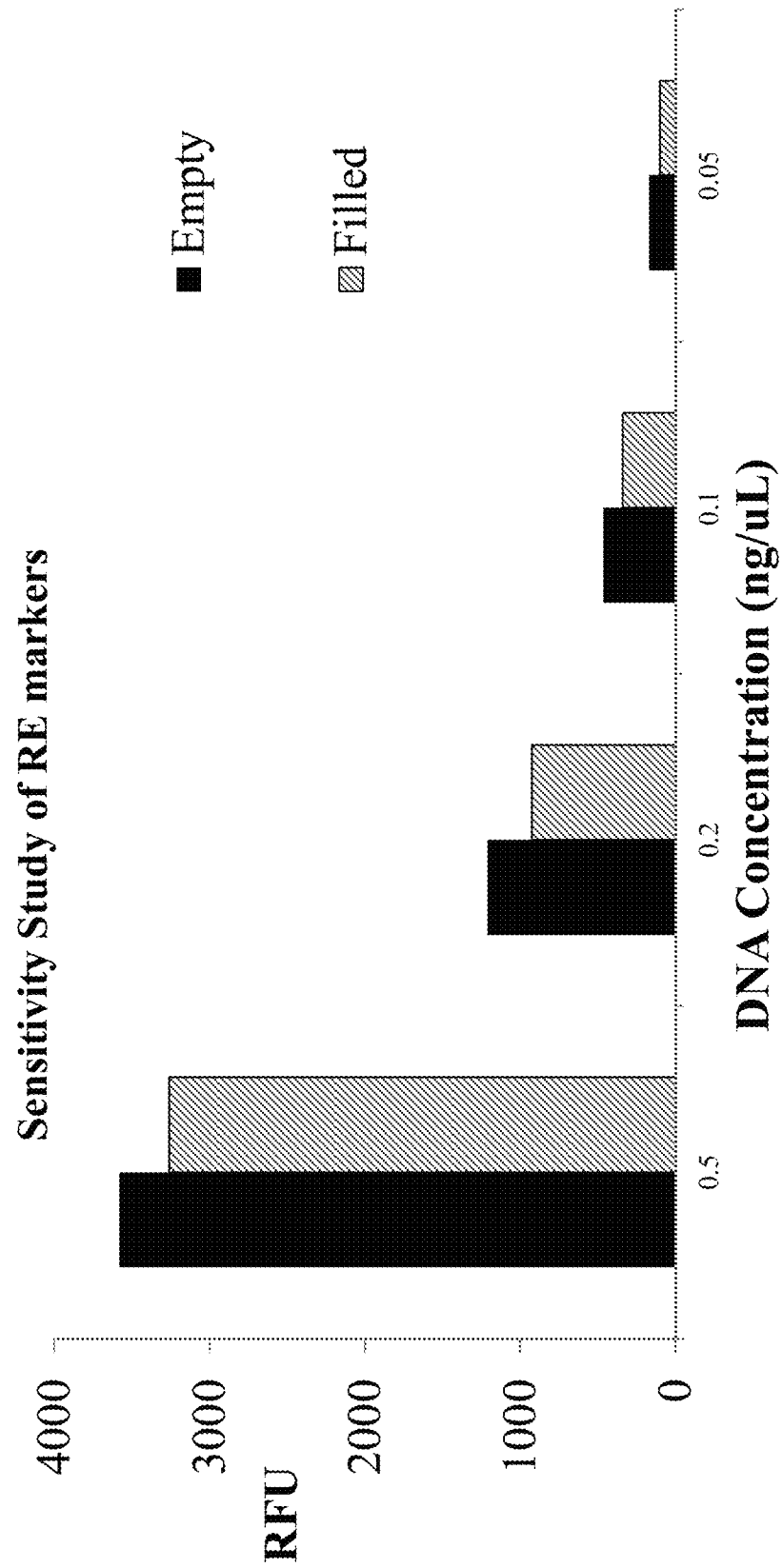

SEQUENCE LISTING

```
<160> NUMBER OF SEQ ID NOS: 298

<210> SEQ ID NO 1
<211> LENGTH: 20
<212> TYPE: DNA
<213> ORGANISM: Artificial Sequence
<220> FEATURE:
<223> OTHER INFORMATION: Labeled forward primer for CH1-6217, a human
      genetic marker that is useful for genetic detection for forensic
      or bio-ancestry studies.  The "n" is to be replaced with a thymine
      labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 1
nggcccacct atgtctaaaa                                                    20

<210> SEQ ID NO 2
<211> LENGTH: 20
<212> TYPE: DNA
<213> ORGANISM: Artificial Sequence
```

```
<220> FEATURE:
<223> OTHER INFORMATION: Forward primer for CH1-6217, a human genetic
      marker that is useful for genetic detection for forensic or bio-
      ancestry studies.

<400> SEQUENCE: 2
tggcccacct atgtctaaaa                                              20

<210> SEQ ID NO 3
<211> LENGTH: 22
<212> TYPE: DNA
<213> ORGANISM: Artificial Sequence
<220> FEATURE:
<223> OTHER INFORMATION: Reverse primer for empty sequence for CH1-6217,
      a human genetic marker that is useful for genetic detection for
      forensic or bio-ancestry studies.

<400> SEQUENCE: 3
gttgattcaa agcaaccaat cc                                           22

<210> SEQ ID NO 4
<211> LENGTH: 20
<212> TYPE: DNA
<213> ORGANISM: Artificial Sequence
<220> FEATURE:
<223> OTHER INFORMATION: Reverse primer for filled sequence for CH1-
      6217, a human genetic marker that is useful for genetic detection
      for forensic or bio-ancestry studies.

<400> SEQUENCE: 4
gtcaaggcaa accaatccaa                                              20

<210> SEQ ID NO 5
<211> LENGTH: 22
<212> TYPE: DNA
<213> ORGANISM: Artificial Sequence
<220> FEATURE:
<223> OTHER INFORMATION: Labeled forward primer for pAlu1-2767, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 5
ngtacttggg agctcagagc ag                                           22

<210> SEQ ID NO 6
<211> LENGTH: 22
<212> TYPE: DNA
<213> ORGANISM: Artificial Sequence
<220> FEATURE:
<223> OTHER INFORMATION: Forward primer for pAlu1-2767, a human genetic
      marker that is useful for genetic detection for forensic or bio-
      ancestry studies.

<400> SEQUENCE: 6
tgtacttggg agctcagagc ag                                           22

<210> SEQ ID NO 7
<211> LENGTH: 20
<212> TYPE: DNA
<213> ORGANISM: Artificial Sequence
```

```
<220> FEATURE:
<223> OTHER INFORMATION: Labeled reverse primer for empty sequence for
      pAlu1-2767, a human genetic marker that is useful for genetic
      detection for forensic or bio-ancestry studies.  The "n" is to be
      replaced with a thymine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 7
ngctcttcct tcttccttct                                                   20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for empty sequence for pAlu1-
      2767, a human genetic marker that is useful for genetic detection
      for forensic or bio-ancestry studies.

<400> SEQUENCE: 8
tgctcttcct tcttccttct                                                   20

<210> SEQ ID NO 9
<211> LENGTH: 20
<212> TYPE: DNA
<213> ORGANISM: Artificial Sequence
<220> FEATURE:
<223> OTHER INFORMATION: Reverse primer for filled sequence for pAlu1-
      2767, a human genetic marker that is useful for genetic detection
      for forensic or bio-ancestry studies.  The "n" is to be replaced
      with a thymine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 9
ntccggcccc cttcttcctt                                                   20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for filled sequence for pAlu1-
      2767, a human genetic marker that is useful for genetic detection
      for forensic or bio-ancestry studies.

<400> SEQUENCE: 10
ttccggcccc cttcttcctt                                                   20

<210> SEQ ID NO 11
<211> LENGTH: 25
<212> TYPE: DNA
<213> ORGANISM: Artificial Sequence
<220> FEATURE:
<223> OTHER INFORMATION: Labeled forward primer for TARBP1, a human
      genetic marker that is useful for genetic detection for forensic
      or bio-ancestry studies.  The "n" is to be replaced with a
      cytosine labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 11
ncaaagttta ctataaggag gcaaa                                             25
```

<210> SEQ ID NO 12
<211> LENGTH: 25
<212> TYPE: DNA
<213> ORGANISM: Artificial Sequence
<220> FEATURE:
<223> OTHER INFORMATION: Forward primer for TARBP1, a human genetic
      marker that is useful for genetic detection for forensic or bio-
      ancestry studies.

<400> SEQUENCE: 12
ccaaagttta ctataaggag gcaaa                                           25

<210> SEQ ID NO 13
<211> LENGTH: 24
<212> TYPE: DNA
<213> ORGANISM: Artificial Sequence
<220> FEATURE:
<223> OTHER INFORMATION: Reverse primer for empty sequence for TARBP1, a
      human genetic marker that is useful for genetic detection for
      forensic or bio-ancestry studies.

<400> SEQUENCE: 13
tgatccagtc attcatcatt ttat                                            24

<210> SEQ ID NO 14
<211> LENGTH: 18
<212> TYPE: DNA
<213> ORGANISM: Artificial Sequence
<220> FEATURE:
<223> OTHER INFORMATION: Reverse primer for filled sequence for TARBP1,
      a human genetic marker that is useful for genetic detection for
      forensic or bio-ancestry studies.

<400> SEQUENCE: 14
cggcccattc atcagttt                                                   18

<210> SEQ ID NO 15
<211> LENGTH: 22
<212> TYPE: DNA
<213> ORGANISM: Artificial Sequence
<220> FEATURE:
<223> OTHER INFORMATION: Labeled forward primer for TARBP1, a human
      genetic marker that is useful for genetic detection for forensic
      or bio-ancestry studies.  The "n" is to be replaced with an
      adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 15
naggaggcaa aggaagaata ca                                              22

<210> SEQ ID NO 16
<211> LENGTH: 22
<212> TYPE: DNA
<213> ORGANISM: Artificial Sequence
<220> FEATURE:
<223> OTHER INFORMATION: Forward primer for TARBP1, a human genetic
      marker that is useful for genetic detection for forensic or bio-
      ancestry studies.

<400> SEQUENCE: 16
aaggaggcaa aggaagaata ca                                              22

<210> SEQ ID NO 17
<211> LENGTH: 26
<212> TYPE: DNA
<213> ORGANISM: Artificial Sequence

```
<220> FEATURE:
<223> OTHER INFORMATION: Reverse primer for empty sequence for TARBP1, a
      human genetic marker that is useful for genetic detection for
      forensic or bio-ancestry studies.

<400> SEQUENCE: 17
gttgatccag tcattcatca ttttat                                          26

<210> SEQ ID NO 18
<211> LENGTH: 19
<212> TYPE: DNA
<213> ORGANISM: Artificial Sequence
<220> FEATURE:
<223> OTHER INFORMATION: Reverse primer for filled sequence for TARPB1,
      a human genetic marker that is useful for genetic detection for
      forensic or bio-ancestry studies.

<400> SEQUENCE: 18
gcggcccatt catcagttt                                                  19

<210> SEQ ID NO 19
<211> LENGTH: 22
<212> TYPE: DNA
<213> ORGANISM: Artificial Sequence
<220> FEATURE:
<223> OTHER INFORMATION: Labeled forward primer for Ya5-MLS48, a human
      genetic marker that is useful for genetic detection for forensic
      or bio-ancestry studies.  The "n" is to be replaced with a thymine
      labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 19
ntggcttgta aactaattgc tg                                              22

<210> SEQ ID NO 20
<211> LENGTH: 22
<212> TYPE: DNA
<213> ORGANISM: Artificial Sequence
<220> FEATURE:
<223> OTHER INFORMATION: Forward primer for Ya5-MLS48, a human genetic
      marker that is useful for genetic detection for forensic or bio-
      ancestry studies.

<400> SEQUENCE: 20
ttggcttgta aactaattgc tg                                              22

<210> SEQ ID NO 21
<211> LENGTH: 24
<212> TYPE: DNA
<213> ORGANISM: Artificial Sequence
<220> FEATURE:
<223> OTHER INFORMATION: Reverse primer for empty sequence for
      Ya5-MLS48, a human genetic marker that is useful for genetic
      detection for forensic or bio-ancestry studies.

<400> SEQUENCE: 21
gcaaagcaac ttgcaccttt tcta                                            24

<210> SEQ ID NO 22
<211> LENGTH: 21
<212> TYPE: DNA
<213> ORGANISM: Artificial Sequence
<220> FEATURE:
<223> OTHER INFORMATION: Reverse primer for filled sequence for
      Ya5-MLS48, a human genetic marker that is useful for genetic
      detection for forensic or bio-ancestry studies.
```

-continued

```
<400> SEQUENCE: 22
gcggccgcac cttttctatt g                                              21

<210> SEQ ID NO 23
<211> LENGTH: 28
<212> TYPE: DNA
<213> ORGANISM: Artificial Sequence
<220> FEATURE:
<223> OTHER INFORMATION: Labeled forward primer for Yb8AC1141, a human
      genetic marker that is useful for genetic detection for forensic
      or bio-ancestry studies.  The "n" is to be replaced with a thymine
      labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 23
nacaaatact acagacaaaa gctactga                                       28

<210> SEQ ID NO 24
<211> LENGTH: 28
<212> TYPE: DNA
<213> ORGANISM: Artificial Sequence
<220> FEATURE:
<223> OTHER INFORMATION: Forward primer for Yb8AC1141, a human genetic
      marker that is useful for genetic detection for forensic or bio-
      ancestry studies.

<400> SEQUENCE: 24
tacaaatact acagacaaaa gctactga                                       28

<210> SEQ ID NO 25
<211> LENGTH: 21
<212> TYPE: DNA
<213> ORGANISM: Artificial Sequence
<220> FEATURE:
<223> OTHER INFORMATION: Reverse primer for empty sequence for
      Yb8AC1141, a human genetic marker that is useful for genetic
      detection for forensic or bio-ancestry studies.

<400> SEQUENCE: 25 gagaaccccca ccaacctgac t                                             21

<210> SEQ ID NO 26
<211> LENGTH: 18
<212> TYPE: DNA
<213> ORGANISM: Artificial Sequence
<220> FEATURE:
<223> OTHER INFORMATION: Reverse primer for filled sequence for
      Yb8AC1141, a human genetic marker that is useful for genetic
      detection for forensic or bio-ancestry studies.

<400> SEQUENCE: 26
ccggcccaac ctgactta                                                  18

<210> SEQ ID NO 27
<211> LENGTH: 27
<212> TYPE: DNA
<213> ORGANISM: Artificial Sequence
<220> FEATURE:
<223> OTHER INFORMATION: Labeled forward primer for Yb8AC1141, a
      human genetic marker that is useful for genetic detection for
      forensic or bio-ancestry studies.  The "n" is to be replaced with
      an adenine labeled with ROX dye.
<220> FEATURE:
<221> NAME/KEY: misc_feature
<222> LOCATION: (1)..(1)
<223> OTHER INFORMATION: n is a, c, g, or t
```

<400> SEQUENCE: 27
ncaaatacta cagacaaaag ctactga         27

<210> SEQ ID NO 28
<211> LENGTH: 27
<212> TYPE: DNA
<213> ORGANISM: Artificial Sequence
<220> FEATURE:
<223> OTHER INFORMATION: Forward primer for Yb8AC1141, a human genetic marker that is useful for genetic detection for forensic or bio-ancestry studies.

<400> SEQUENCE: 28
acaaatacta cagacaaaag ctactga         27

<210> SEQ ID NO 29
<211> LENGTH: 19
<212> TYPE: DNA
<213> ORGANISM: Artificial Sequence
<220> FEATURE:
<223> OTHER INFORMATION: Reverse primer for empty sequence for Yb8AC1141, a human genetic marker that is useful for genetic detection for forensic or bio-ancestry studies.

<400> SEQUENCE: 29
gaaccccacc aacctgact         19

<210> SEQ ID NO 30
<211> LENGTH: 18
<212> TYPE: DNA
<213> ORGANISM: Artificial Sequence
<220> FEATURE:
<223> OTHER INFORMATION: Reverse primer for filled sequence for Yb8AC1141, a human genetic marker that is useful for genetic detection for forensic or bio-ancestry studies.

<400> SEQUENCE: 30
ggcccaacct gacttact         18

<210> SEQ ID NO 31
<211> LENGTH: 21
<212> TYPE: DNA
<213> ORGANISM: Artificial Sequence
<220> FEATURE:
<223> OTHER INFORMATION: Labeled forward primer for LC3-2601, a human genetic marker that is useful for genetic detection for forensic or bio-ancestry studies. The "n" is to be replaced with a thymine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 31
ntggccatag aaaaaccagt c         21

<210> SEQ ID NO 32
<211> LENGTH: 21
<212> TYPE: DNA
<213> ORGANISM: Artificial Sequence
<220> FEATURE:
<223> OTHER INFORMATION: Forward primer for LC3-2601, a human genetic marker that is useful for genetic detection for forensic or bio-ancestry studies.

<400> SEQUENCE: 32
ttggccatag aaaaaccagt c         21

<210> SEQ ID NO 33
<211> LENGTH: 19
<212> TYPE: DNA
<213> ORGANISM: Artificial Sequence
<220> FEATURE:
<223> OTHER INFORMATION: Reverse primer for empty sequence for CHR20-
      79712, a human genetic marker that is useful for genetic detection
      for forensic or bio-ancestry studies. The "n" is to be replaced
      with an adenine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 33
ngaatcagaa tggggtctt                                               19

<210> SEQ ID NO 34
<211> LENGTH: 19
<212> TYPE: DNA
<213> ORGANISM: Artificial Sequence
<220> FEATURE:
<223> OTHER INFORMATION: Reverse primer for empty sequence for LC3-2601,
      a human genetic marker that is useful for genetic detection for
      forensic or bio-ancestry studies.

<400> SEQUENCE: 34
agaatcagaa tggggtctt                                               19

<210> SEQ ID NO 35
<211> LENGTH: 20
<212> TYPE: DNA
<213> ORGANISM: Artificial Sequence
<220> FEATURE:
<223> OTHER INFORMATION: Reverse primer for filled sequence for LC3-
      2601, a human genetic marker that is useful for genetic detection
      for forensic or bio-ancestry studies. The "n" is to be replaced
      with an adenine labeled with JOE dye.

<400> SEQUENCE: 35
atcttggctc ctccgtttgt                                              20

<210> SEQ ID NO 36
<211> LENGTH: 20
<212> TYPE: DNA
<213> ORGANISM: Artificial Sequence
<220> FEATURE:
<223> OTHER INFORMATION: Reverse primer for filled sequence for
      LC3-2601, a human genetic marker that is useful for genetic
      detection for forensic or bio-ancestry studies.

<400> SEQUENCE: 36
atcttggctc ctccgtttgt                                              20

<210> SEQ ID NO 37
<211> LENGTH: 21
<212> TYPE: DNA
<213> ORGANISM: Artificial Sequence
<220> FEATURE:
<223> OTHER INFORMATION: Labeled forward primer for Ya5NBC51, a human
      genetic marker that is useful for genetic detection for forensic
      or bio-ancestry studies. The "n" is to be replaced with a thymine
      labeled with TMR dye.

<400> SEQUENCE: 37
tcgccatctc ttcttccttc a                                            21

```
<210> SEQ ID NO 38
<211> LENGTH: 21
<212> TYPE: DNA
<213> ORGANISM: Artificial Sequence
<220> FEATURE:
<223> OTHER INFORMATION: Forward primer for Ya5NBC51, a human genetic
      marker that is useful for genetic detection for forensic or bio-
      ancestry studies.

<400> SEQUENCE: 38
tcgccatctc ttcttccttc a                                              21

<210> SEQ ID NO 39
<211> LENGTH: 21
<212> TYPE: DNA
<213> ORGANISM: Artificial Sequence
<220> FEATURE:
<223> OTHER INFORMATION: Reverse primer for empty sequence for Ya5NBC51,
      a human genetic marker that is useful for genetic detection for
      forensic or bio-ancestry studies.

<400> SEQUENCE: 39
gtccagggtt aatgctttgt t                                              21

<210> SEQ ID NO 40
<211> LENGTH: 20
<212> TYPE: DNA
<213> ORGANISM: Artificial Sequence
<220> FEATURE:
<223> OTHER INFORMATION: Reverse primer for filled sequence for
      Ya5NBC51, a human genetic marker that is useful for genetic
      detection for forensic or bio-ancestry studies.

<400> SEQUENCE: 40
ttacaggcgt gagaatgctt                                                20

<210> SEQ ID NO 41
<211> LENGTH: 21
<212> TYPE: DNA
<213> ORGANISM: Artificial Sequence
<220> FEATURE:
<223> OTHER INFORMATION: Labeled forward primer for Ya5NBC51, a human
      genetic marker that is useful for genetic detection for forensic
      or bio-ancestry studies.  The "n" is to be replaced with a thymine
      labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 41
ncgccatctc ttcttccttc a                                              21

<210> SEQ ID NO 42
<211> LENGTH: 20
<212> TYPE: DNA
<213> ORGANISM: Artificial Sequence
<220> FEATURE:
<223> OTHER INFORMATION: Reverse primer for empty sequence for Ya5NBC51,
      a human genetic marker that is useful for genetic detection for
      forensic or bio-ancestry studies.

<400> SEQUENCE: 42
gtccagggtt aatgctttgt                                                20

<210> SEQ ID NO 43
<211> LENGTH: 20
<212> TYPE: DNA
<213> ORGANISM: Artificial Sequence
```

<220> FEATURE:
<223> OTHER INFORMATION: Reverse primer for filled sequence for
      Ya5NBC51, a human genetic marker that is useful for genetic
      detection for forensic or bio-ancestry studies.

<400> SEQUENCE: 43
gtccagggtt aatgctttgt                                           20

<210> SEQ ID NO 44
<211> LENGTH: 25
<212> TYPE: DNA
<213> ORGANISM: Artificial Sequence
<220> FEATURE:
<223> OTHER INFORMATION: Labeled forward primer for HS4.69
      (NC000005.10), a human genetic marker that is useful for genetic
      detection for forensic or bio-ancestry studies. The "n" is to be
      replaced with a thymine labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 44
ngccaggtga tagtattagg aggtg                                     25

<210> SEQ ID NO 45
<211> LENGTH: 25
<212> TYPE: DNA
<213> ORGANISM: Artificial Sequence
<220> FEATURE:
<223> OTHER INFORMATION: Forward primer for HS4.69 (NC000005.10), a
      human genetic marker that is useful for genetic detection for
      forensic or bio-ancestry studies.

<400> SEQUENCE: 45
tgccaggtga tagtattagg aggtg                                     25

<210> SEQ ID NO 46
<211> LENGTH: 21
<212> TYPE: DNA
<213> ORGANISM: Artificial Sequence
<220> FEATURE:
<223> OTHER INFORMATION: Reverse primer for empty sequence for HS4.69
      (NC000005.10), a human genetic marker that is useful for genetic
      detection for forensic or bio-ancestry studies.

<400> SEQUENCE: 46
gctagctaac tctctaaggt c                                         21

<210> SEQ ID NO 47
<211> LENGTH: 20
<212> TYPE: DNA
<213> ORGANISM: Artificial Sequence
<220> FEATURE:
<223> OTHER INFORMATION: Reverse primer for filled sequence for HS4.69
      (NC000005.10), a human genetic marker that is useful for genetic
      detection for forensic or bio-ancestry studies.

<400> SEQUENCE: 47
ccggcctcta aggtcttttt                                           20

<210> SEQ ID NO 48
<211> LENGTH: 25
<212> TYPE: DNA
<213> ORGANISM: Artificial Sequence

```
<220> FEATURE:
<223> OTHER INFORMATION: Labeled forward primer for HS4.69
      (NC000005.10), a human genetic marker that is useful for genetic
      detection for forensic or bio-ancestry studies.  The "n" is to be
      replaced with a thymine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 48
ngccaggtga tagtattagg aggtg                                           25

<210> SEQ ID NO 49
<211> LENGTH: 28
<212> TYPE: DNA
<213> ORGANISM: Artificial Sequence
<220> FEATURE:
<223> OTHER INFORMATION: Reverse primer for empty sequence for HS4.69
      (NC000005.10), a human genetic marker that is useful for genetic
      detection for forensic or bio-ancestry studies.

<400> SEQUENCE: 49
ggcatcgtat ctattcatgt gattttta                                        28

<210> SEQ ID NO 50
<211> LENGTH: 20
<212> TYPE: DNA
<213> ORGANISM: Artificial Sequence
<220> FEATURE:
<223> OTHER INFORMATION: Reverse primer for filled sequence for HS4.69
      (NC000005.10), a human genetic marker that is useful for genetic
      detection for forensic or bio-ancestry studies.

<400> SEQUENCE: 50
ccggcctatt catgtgattt                                                 20

<210> SEQ ID NO 51
<211> LENGTH: 20
<212> TYPE: DNA
<213> ORGANISM: Artificial Sequence
<220> FEATURE:
<223> OTHER INFORMATION: Labeled forward primer for Ya5ACA1736, a human
      genetic marker that is useful for genetic detection for forensic
      or bio-ancestry studies.  The "n" is to be replaced with a
      cytosine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 51
nctgctctgc acacttcttg                                                 20

<210> SEQ ID NO 52
<211> LENGTH: 20
<212> TYPE: DNA
<213> ORGANISM: Artificial Sequence
<220> FEATURE:
<223> OTHER INFORMATION: Forward primer for Ya5ACA1736, a human genetic
      marker that is useful for genetic detection for forensic or bio-
      ancestry studies.

<400> SEQUENCE: 52
cctgctctgc acacttcttg                                                 20
```

```
<210> SEQ ID NO 53
<211> LENGTH: 23
<212> TYPE: DNA
<213> ORGANISM: Artificial Sequence
<220> FEATURE:
<223> OTHER INFORMATION: Reverse primer for empty sequence for
      Ya5ACA1736, a human genetic marker that is useful for genetic
      detection for forensic or bio-ancestry studies.

<400> SEQUENCE: 53
gaccttgacc tagagaaggc aat                                           23

<210> SEQ ID NO 54
<211> LENGTH: 20
<212> TYPE: DNA
<213> ORGANISM: Artificial Sequence
<220> FEATURE:
<223> OTHER INFORMATION: Reverse primer for filled sequence for
      Ya5ACA1736, a human genetic marker that is useful for genetic
      detection for forensic or bio-ancestry studies.

<400> SEQUENCE: 54
gccgagaagg caattttcta                                               20

<210> SEQ ID NO 55
<211> LENGTH: 21
<212> TYPE: DNA
<213> ORGANISM: Artificial Sequence
<220> FEATURE:
<223> OTHER INFORMATION: Labeled forward primer for CH26240, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 55
nggtgacaga gtgagacctt g                                             21

<210> SEQ ID NO 56
<211> LENGTH: 21
<212> TYPE: DNA
<213> ORGANISM: Artificial Sequence
<220> FEATURE:
<223> OTHER INFORMATION: Forward primer for CH26240, a human genetic
      marker that is useful for genetic detection for forensic or bio-
      ancestry studies.

<400> SEQUENCE: 56
tggtgacaga gtgagacctt g                                             21

<210> SEQ ID NO 57
<211> LENGTH: 24
<212> TYPE: DNA
<213> ORGANISM: Artificial Sequence
<220> FEATURE:
<223> OTHER INFORMATION: Reverse primer for empty sequence for CH26240,
      a human genetic marker that is useful for genetic detection for
      forensic or bio-ancestry studies.  The "n" is to be replaced with
      a thymine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 57
ngactcatgt aacttgtctg cttg                                          24
```

```
<210> SEQ ID NO 58
<211> LENGTH: 24
<212> TYPE: DNA
<213> ORGANISM: Artificial Sequence
<220> FEATURE:
<223> OTHER INFORMATION: Reverse primer for empty sequence for CH26240,
      a human genetic marker that is useful for genetic detection for
      forensic or bio-ancestry studies.

<400> SEQUENCE: 58
tgactcatgt aacttgtctg cttg                                              24

<210> SEQ ID NO 59
<211> LENGTH: 20
<212> TYPE: DNA
<213> ORGANISM: Artificial Sequence
<220> FEATURE:
<223> OTHER INFORMATION: Reverse primer for filled sequence for CH26240,
      a human genetic marker that is useful for genetic detection for
      forensic or bio-ancestry studies.  The "n" is to be replaced with
      a thymine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 59
ngttggacat ttgcataccc                                                   20

<210> SEQ ID NO 60
<211> LENGTH: 20
<212> TYPE: DNA
<213> ORGANISM: Artificial Sequence
<220> FEATURE:
<223> OTHER INFORMATION: Reverse primer for filled sequence for CH26240,
      a human genetic marker that is useful for genetic detection for
      forensic or bio-ancestry studies.

<400> SEQUENCE: 60
tgttggacat ttgcataccc                                                   20

<210> SEQ ID NO 61
<211> LENGTH: 24
<212> TYPE: DNA
<213> ORGANISM: Artificial Sequence
<220> FEATURE:
<223> OTHER INFORMATION: Labeled forward primer for Ya5NBC327, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 61
ngtcatgtac aaacagggat agtt                                              24

<210> SEQ ID NO 62
<211> LENGTH: 24
<212> TYPE: DNA
<213> ORGANISM: Artificial Sequence
<220> FEATURE:
<223> OTHER INFORMATION: Forward primer for Ya5NBC327, a human genetic
      marker that is useful for genetic detection for forensic or bio-
      ancestry studies.

<400> SEQUENCE: 62
tgtcatgtac aaacagggat agtt                                              24
```

<210> SEQ ID NO 63
<211> LENGTH: 20
<212> TYPE: DNA
<213> ORGANISM: Artificial Sequence
<220> FEATURE:
<223> OTHER INFORMATION: Reverse primer for empty sequence for
     Ya5NBC327, a human genetic marker that is useful for genetic
     detection for forensic or bio-ancestry studies.

<400> SEQUENCE: 63
gcgcccggcc ctcattattc                                              20

<210> SEQ ID NO 64
<211> LENGTH: 27
<212> TYPE: DNA
<213> ORGANISM: Artificial Sequence
<220> FEATURE:
<223> OTHER INFORMATION: Reverse primer for filled sequence for
     Ya5NBC327, a human genetic marker that is useful for genetic
     detection for forensic or bio-ancestry studies.

<400> SEQUENCE: 64
caaggatacc cattctcatt attctta                                      27

<210> SEQ ID NO 65
<211> LENGTH: 19
<212> TYPE: DNA
<213> ORGANISM: Artificial Sequence
<220> FEATURE:
<223> OTHER INFORMATION: Labeled forward primer for CH6-28-9163, a human
     genetic marker that is useful for genetic detection for forensic
     or bio-ancestry studies.  The "n" is to be replaced with a thymine
     labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 65
nggctgtggt ggaggataa                                               19

<210> SEQ ID NO 66
<211> LENGTH: 19
<212> TYPE: DNA
<213> ORGANISM: Artificial Sequence
<220> FEATURE:
<223> OTHER INFORMATION: Forward primer for CH6-28-9163, a human genetic
     marker that is useful for genetic detection for forensic or bio-
     ancestry studies.

<400> SEQUENCE: 66
tggctgtggt ggaggataa                                               19

<210> SEQ ID NO 67
<211> LENGTH: 20
<212> TYPE: DNA
<213> ORGANISM: Artificial Sequence
<220> FEATURE:
<223> OTHER INFORMATION: Reverse primer for empty sequence for CH6-28-
     9163, a human genetic marker that is useful for genetic detection
     for forensic or bio-ancestry studies.

<400> SEQUENCE: 67
gcacatgcca ccatacccag                                              20

<210> SEQ ID NO 68
<211> LENGTH: 22
<212> TYPE: DNA
<213> ORGANISM: Artificial Sequence

```
<220> FEATURE:
<223> OTHER INFORMATION: Reverse primer for filled sequence for CH6-28-
      9163, a human genetic marker that is useful for genetic detection
      for forensic or bio-ancestry studies.

<400> SEQUENCE: 68
gccatcttgg ctccagttag tt                                              22

<210> SEQ ID NO 69
<211> LENGTH: 20
<212> TYPE: DNA
<213> ORGANISM: Artificial Sequence
<220> FEATURE:
<223> OTHER INFORMATION: Labeled forward primer for Ya5NBC239, a human
      genetic marker that is useful for genetic detection for forensic
      or bio-ancestry studies.  The "n" is to be replaced with a thymine
      labeled with 6-FAM dye.

<400> SEQUENCE: 69
ttcctgctat gagccacgta                                                 20

<210> SEQ ID NO 70
<211> LENGTH: 20
<212> TYPE: DNA
<213> ORGANISM: Artificial Sequence
<220> FEATURE:
<223> OTHER INFORMATION: Forward primer for Ya5NBC239, a human genetic
      marker that is useful for genetic detection for forensic or bio-
      ancestry studies.

<400> SEQUENCE: 70
ttcctgctat gagccacgta                                                 20

<210> SEQ ID NO 71
<211> LENGTH: 27
<212> TYPE: DNA
<213> ORGANISM: Artificial Sequence
<220> FEATURE:
<223> OTHER INFORMATION: Reverse primer for empty sequence for
      Ya5NBC239, a human genetic marker that is useful for genetic
      detection for forensic or bio-ancestry studies.

<400> SEQUENCE: 71
catttagatc tcacatgatt cttatgc                                         27

<210> SEQ ID NO 72
<211> LENGTH: 20
<212> TYPE: DNA
<213> ORGANISM: Artificial Sequence
<220> FEATURE:
<223> OTHER INFORMATION: Reverse primer for filled sequence for
      Ya5NBC239, a human genetic marker that is useful for genetic
      detection for forensic or bio-ancestry studies.

<400> SEQUENCE: 72
ccggcctcac atgattctta                                                 20

<210> SEQ ID NO 73
<211> LENGTH: 26
<212> TYPE: DNA
<213> ORGANISM: Artificial Sequence
<220> FEATURE:
<223> OTHER INFORMATION: Labeled forward primer for Yb7AD155, a human
      genetic marker that is useful for genetic detection for forensic
      or bio-ancestry studies.  The "n" is to be replaced with a thymine
      labeled with ROX dye.
```

```
<220> FEATURE:
<221> NAME/KEY: misc_feature
<222> LOCATION: (1)..(1)
<223> OTHER INFORMATION: n is a, c, g, or t

<400> SEQUENCE: 73
ngtacacatt aagcacatgg aagtca                                              26

<210> SEQ ID NO 74
<211> LENGTH: 26
<212> TYPE: DNA
<213> ORGANISM: Artificial Sequence
<220> FEATURE:
<223> OTHER INFORMATION: Forward primer for Yb7AD155, a human genetic
      marker that is useful for genetic detection for forensic or bio-
      ancestry studies.

<400> SEQUENCE: 74
tgtacacatt aagcacatgg aagtca                                              26

<210> SEQ ID NO 75
<211> LENGTH: 23
<212> TYPE: DNA
<213> ORGANISM: Artificial Sequence
<220> FEATURE:
<223> OTHER INFORMATION: Reverse primer for empty sequence for Yb7AD155,
      a human genetic marker that is useful for genetic detection for
      forensic or bio-ancestry studies.

<400> SEQUENCE: 75
gcatgaaatg ttctttttca tct                                                 23

<210> SEQ ID NO 76
<211> LENGTH: 18
<212> TYPE: DNA
<213> ORGANISM: Artificial Sequence
<220> FEATURE:
<223> OTHER INFORMATION: Reverse primer for filled sequence for
      Yb7AD155, a human genetic marker that is useful for genetic
      detection for forensic or bio-ancestry studies.

<400> SEQUENCE: 76
gcccggccgt tcttttc                                                        18

<210> SEQ ID NO 77
<211> LENGTH: 23
<212> TYPE: DNA
<213> ORGANISM: Artificial Sequence
<220> FEATURE:
<223> OTHER INFORMATION: Labeled forward primer for Ya5-MLS18, a human
      genetic marker that is useful for genetic detection for forensic
      or bio-ancestry studies.  The "n" is to be replaced with an
      adenine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 77
nacttcaagg tatttgcatc atg                                                 23

<210> SEQ ID NO 78
<211> LENGTH: 23
<212> TYPE: DNA
<213> ORGANISM: Artificial Sequence
<220> FEATURE:
<223> OTHER INFORMATION: Forward primer for Ya5-MLS18, a human genetic
      marker that is useful for genetic detection for forensic or bio-
      ancestry studies.
```

<400> SEQUENCE: 78
aacttcaagg tatttgcatc atg                                    23

<210> SEQ ID NO 79
<211> LENGTH: 24
<212> TYPE: DNA
<213> ORGANISM: Artificial Sequence
<220> FEATURE:
<223> OTHER INFORMATION: Reverse primer for empty sequence for
      Ya5-MLS18, a human genetic marker that is useful for genetic
      detection for forensic or bio-ancestry studies.

<400> SEQUENCE: 79
tgctagctaa ctctctaagg tctt                                   24

<210> SEQ ID NO 80
<211> LENGTH: 20
<212> TYPE: DNA
<213> ORGANISM: Artificial Sequence
<220> FEATURE:
<223> OTHER INFORMATION: Reverse primer for filled sequence for
      Ya5-MLS18, a human genetic marker that is useful for genetic
      detection for forensic or bio-ancestry studies.

<400> SEQUENCE: 80
ccggcctcta aggtcttttt                                        20

<210> SEQ ID NO 81
<211> LENGTH: 23
<212> TYPE: DNA
<213> ORGANISM: Artificial Sequence
<220> FEATURE:
<223> OTHER INFORMATION: Labeled forward primer for Ya5-MLS18, a human
      genetic marker that is useful for genetic detection for forensic
      or bio-ancestry studies. The "n" is to be replaced with an
      adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 81
nacttcaagg tatttgcatc atg                                    23

<210> SEQ ID NO 82
<211> LENGTH: 28
<212> TYPE: DNA
<213> ORGANISM: Artificial Sequence
<220> FEATURE:
<223> OTHER INFORMATION: Reverse primer for empty sequence for
      Ya5-MLS18, a human genetic marker that is useful for genetic
      detection for forensic or bio-ancestry studies.

<400> SEQUENCE: 82
ggcatcgtat ctattcatgt gatttta                                28

<210> SEQ ID NO 83
<211> LENGTH: 20
<212> TYPE: DNA
<213> ORGANISM: Artificial Sequence
<220> FEATURE:
<223> OTHER INFORMATION: Reverse primer for filled sequence for
      Ya5-MLS18, a human genetic marker that is useful for genetic
      detection for forensic or bio-ancestry studies.

<400> SEQUENCE: 83
ccggcctatt catgtgattt                                        20

-continued

```
<210> SEQ ID NO 84
<211> LENGTH: 25
<212> TYPE: DNA
<213> ORGANISM: Artificial Sequence
<220> FEATURE:
<223> OTHER INFORMATION: Labeled forward primer for CH4-12-7012 L1HS39,
      a human genetic marker that is useful for genetic detection for
      forensic or bio-ancestry studies.  The "n" is to be replaced with
      a guanine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 84
ngaaaggtac aagatgtaat gagga                                          25

<210> SEQ ID NO 85
<211> LENGTH: 25
<212> TYPE: DNA
<213> ORGANISM: Artificial Sequence
<220> FEATURE:
<223> OTHER INFORMATION: Forward primer for CH4-12-7012 L1HS39, a human
      genetic marker that is useful for genetic detection for forensic
      or bio-ancestry studies.

<400> SEQUENCE: 85
ggaaaggtac aagatgtaat gagga                                          25

<210> SEQ ID NO 86
<211> LENGTH: 21
<212> TYPE: DNA
<213> ORGANISM: Artificial Sequence
<220> FEATURE:
<223> OTHER INFORMATION: Reverse primer for empty sequence for CHR20-
      79712, a human genetic marker that is useful for genetic detection
      for forensic or bio-ancestry studies.  The "n" is to be replaced
      with a thymine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 86
ntgcccacac cttgatcttg a                                              21

<210> SEQ ID NO 87
<211> LENGTH: 21
<212> TYPE: DNA
<213> ORGANISM: Artificial Sequence
<220> FEATURE:
<223> OTHER INFORMATION: Reverse primer for empty sequence for CH4-12-
      7012 L1HS39, a human genetic marker that is useful for genetic
      detection for forensic or bio-ancestry studies.

<400> SEQUENCE: 87
ttgcccacac cttgatcttg a                                              21

<210> SEQ ID NO 88
<211> LENGTH: 22
<212> TYPE: DNA
<213> ORGANISM: Artificial Sequence
<220> FEATURE:
<223> OTHER INFORMATION: Reverse primer for filled sequence for CH4-12-
      7012 L1HS39, a human genetic marker that is useful for genetic
      detection for forensic or bio-ancestry studies.  The "n" is to be
      replaced with a cytosine labeled with JOE dye.
<220> FEATURE:
<221> NAME/KEY: misc_feature
<222> LOCATION: (1)..(1)
<223> OTHER INFORMATION: n is a, c, g, or t
```

```
<400> SEQUENCE: 88
nggaggaaaa tggccaagac aa                                              22

<210> SEQ ID NO 89
<211> LENGTH: 22
<212> TYPE: DNA
<213> ORGANISM: Artificial Sequence
<220> FEATURE:
<223> OTHER INFORMATION: Reverse primer for filled sequence for CH4-12-
      7012 L1HS39, a human genetic marker that is useful for genetic
      detection for forensic or bio-ancestry studies.

<400> SEQUENCE: 89
cggaggaaaa tggccaagac aa                                              22

<210> SEQ ID NO 90
<211> LENGTH: 25
<212> TYPE: DNA
<213> ORGANISM: Artificial Sequence
<220> FEATURE:
<223> OTHER INFORMATION: Labeled forward primer for Ya5ac2305, a human
      genetic marker that is useful for genetic detection for forensic
      or bio-ancestry studies.  The "n" is to be replaced with a thymine
      labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 90
nttaaaatac aatccaacac cattt                                           25

<210> SEQ ID NO 91
<211> LENGTH: 25
<212> TYPE: DNA
<213> ORGANISM: Artificial Sequence
<220> FEATURE:
<223> OTHER INFORMATION: Forward primer for Ya5ac2305, a human genetic
      marker that is useful for genetic detection for forensic or bio-
      ancestry studies.

<400> SEQUENCE: 91
tttaaaatac aatccaacac cattt                                           25

<210> SEQ ID NO 92
<211> LENGTH: 24
<212> TYPE: DNA
<213> ORGANISM: Artificial Sequence
<220> FEATURE:
<223> OTHER INFORMATION: Reverse primer for empty sequence for
      Ya5ac2305, a human genetic marker that is useful for genetic
      detection for forensic or bio-ancestry studies.

<400> SEQUENCE: 92
ggcatccttt gattacaact ctta                                            24

<210> SEQ ID NO 93
<211> LENGTH: 18
<212> TYPE: DNA
<213> ORGANISM: Artificial Sequence
<220> FEATURE:
<223> OTHER INFORMATION: Reverse primer for filled sequence for
      Ya5ac2305, a human genetic marker that is useful for genetic
      detection for forensic or bio-ancestry studies.

<400> SEQUENCE: 93
ggccccaatt acaactct                                                   18
```

<210> SEQ ID NO 94
<211> LENGTH: 22
<212> TYPE: DNA
<213> ORGANISM: Artificial Sequence
<220> FEATURE:
<223> OTHER INFORMATION: Labeled forward primer for Ya5ac2305, a human genetic marker that is useful for genetic detection for forensic or bio-ancestry studies. The "n" is to be replaced with a thymine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 94
nggtgacact ccaatttctt ct                                          22

<210> SEQ ID NO 95
<211> LENGTH: 22
<212> TYPE: DNA
<213> ORGANISM: Artificial Sequence
<220> FEATURE:
<223> OTHER INFORMATION: Forward primer for Ya5ac2305, a human genetic marker that is useful for genetic detection for forensic or bio-ancestry studies.

<400> SEQUENCE: 95
tggtgacact ccaatttctt ct                                          22

<210> SEQ ID NO 96
<211> LENGTH: 25
<212> TYPE: DNA
<213> ORGANISM: Artificial Sequence
<220> FEATURE:
<223> OTHER INFORMATION: Reverse primer for filled sequence for Ya5ac2305, a human genetic marker that is useful for genetic detection for forensic or bio-ancestry studies.

<400> SEQUENCE: 96
gccccaatta caactcttaa ggaaa                                       25

<210> SEQ ID NO 97
<211> LENGTH: 24
<212> TYPE: DNA
<213> ORGANISM: Artificial Sequence
<220> FEATURE:
<223> OTHER INFORMATION: Labeled forward primer for Ya5ac2265, a human genetic marker that is useful for genetic detection for forensic or bio-ancestry studies. The "n" is to be replaced with an adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 97
ngaagagtga atgcacattt atga                                        24

<210> SEQ ID NO 98
<211> LENGTH: 24
<212> TYPE: DNA
<213> ORGANISM: Artificial Sequence
<220> FEATURE:
<223> OTHER INFORMATION: Forward primer for Ya5ac2265, a human genetic marker that is useful for genetic detection for forensic or bio-ancestry studies.

<400> SEQUENCE: 98
agaagagtga atgcacattt atga                                        24

```
<210> SEQ ID NO 99
<211> LENGTH: 23
<212> TYPE: DNA
<213> ORGANISM: Artificial Sequence
<220> FEATURE:
<223> OTHER INFORMATION: Reverse primer for empty sequence for
      Ya5ac2265, a human genetic marker that is useful for genetic
      detection for forensic or bio-ancestry studies.

<400> SEQUENCE: 99
ggagtcatga attcagtttc tta                                          23

<210> SEQ ID NO 100
<211> LENGTH: 18
<212> TYPE: DNA
<213> ORGANISM: Artificial Sequence
<220> FEATURE:
<223> OTHER INFORMATION: Reverse primer for filled sequence for
      Ya5ac2265, a human genetic marker that is useful for genetic
      detection for forensic or bio-ancestry studies.

<400> SEQUENCE: 100
gcccggccca gtttctta                                                18

<210> SEQ ID NO 101
<211> LENGTH: 24
<212> TYPE: DNA
<213> ORGANISM: Artificial Sequence
<220> FEATURE:
<223> OTHER INFORMATION: Labeled forward primer for Ya5NBC241, a human
      genetic marker that is useful for genetic detection for forensic
      or bio-ancestry studies.  The "n" is to be replaced with a thymine
      labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 101
nttagttccc cacaattaac atga                                         24

<210> SEQ ID NO 102
<211> LENGTH: 24
<212> TYPE: DNA
<213> ORGANISM: Artificial Sequence
<220> FEATURE:
<223> OTHER INFORMATION: Forward primer for Ya5NBC241, a human genetic
      marker that is useful for genetic detection for forensic or bio-
      ancestry studies.

<400> SEQUENCE: 102
tttagttccc cacaattaac atga                                         24

<210> SEQ ID NO 103
<211> LENGTH: 21
<212> TYPE: DNA
<213> ORGANISM: Artificial Sequence
<220> FEATURE:
<223> OTHER INFORMATION: Reverse primer for empty sequence for
      Ya5NBC241, a human genetic marker that is useful for genetic
      detection for forensic or bio-ancestry studies.

<400> SEQUENCE: 103
gctttccccc agaagatcca t                                            21

<210> SEQ ID NO 104
<211> LENGTH: 19
<212> TYPE: DNA
<213> ORGANISM: Artificial Sequence
```

```
<220> FEATURE:
<223> OTHER INFORMATION: Reverse primer for filled sequence for
      Ya5NBC241, a human genetic marker that is useful for genetic
      detection for forensic or bio-ancestry studies.

<400> SEQUENCE: 104
gccggccaag atccattct                                                    19

<210> SEQ ID NO 105
<211> LENGTH: 20
<212> TYPE: DNA
<213> ORGANISM: Artificial Sequence
<220> FEATURE:
<223> OTHER INFORMATION: Labeled forward primer for Yb8NBC13, a human
      genetic marker that is useful for genetic detection for forensic
      or bio-ancestry studies.  The "n" is to be replaced with a
      cytosine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 105
ntggcaaatg ctacccaagt                                                   20

<210> SEQ ID NO 106
<211> LENGTH: 20
<212> TYPE: DNA
<213> ORGANISM: Artificial Sequence
<220> FEATURE:
<223> OTHER INFORMATION: Forward primer for Yb8NBC13, a human genetic
      marker that is useful for genetic detection for forensic or bio-
      ancestry studies.

<400> SEQUENCE: 106
ctggcaaatg ctacccaagt                                                   20

<210> SEQ ID NO 107
<211> LENGTH: 23
<212> TYPE: DNA
<213> ORGANISM: Artificial Sequence
<220> FEATURE:
<223> OTHER INFORMATION: Reverse primer for empty sequence for Yb8NBC13,
      a human genetic marker that is useful for genetic detection for
      forensic or bio-ancestry studies.

<400> SEQUENCE: 107
gcatcttcct cttcacatct tat                                               23

<210> SEQ ID NO 108
<211> LENGTH: 17
<212> TYPE: DNA
<213> ORGANISM: Artificial Sequence
<220> FEATURE:
<223> OTHER INFORMATION: Reverse primer for filled sequence for
      Yb8NBC13, a human genetic marker that is useful for genetic
      detection for forensic or bio-ancestry studies.

<400> SEQUENCE: 108
ggcccctctt cacatct                                                      17

<210> SEQ ID NO 109
<211> LENGTH: 20
<212> TYPE: DNA
<213> ORGANISM: Artificial Sequence
```

```
<220> FEATURE:
<223> OTHER INFORMATION: Labeled forward primer for Yb8NBC13, a human
      genetic marker that is useful for genetic detection for forensic
      or bio-ancestry studies. The "n" is to be replaced with a
      cytosine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 109
ntggcaaatg ctacccaagt                                              20

<210> SEQ ID NO 110
<211> LENGTH: 23
<212> TYPE: DNA
<213> ORGANISM: Artificial Sequence
<220> FEATURE:
<223> OTHER INFORMATION: Reverse primer for empty sequence for Yb8NBC13,
      a human genetic marker that is useful for genetic detection for
      forensic or bio-ancestry studies.

<400> SEQUENCE: 110
gctgaagcat cttcctcttc aca                                          23

<210> SEQ ID NO 111
<211> LENGTH: 21
<212> TYPE: DNA
<213> ORGANISM: Artificial Sequence
<220> FEATURE:
<223> OTHER INFORMATION: Reverse primer for filled sequence for
      Yb8NBC13, a human genetic marker that is useful for genetic
      detection for forensic or bio-ancestry studies.

<400> SEQUENCE: 111
gcggcccctc ttcacatctt a                                            21

<210> SEQ ID NO 112
<211> LENGTH: 21
<212> TYPE: DNA
<213> ORGANISM: Artificial Sequence
<220> FEATURE:
<223> OTHER INFORMATION: Labeled forward primer for Yb8NBC13, a human
      genetic marker that is useful for genetic detection for forensic
      or bio-ancestry studies. The "n" is to be replaced with a thymine
      labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 112
nctggcaaat gctacccaag t                                            21

<210> SEQ ID NO 113
<211> LENGTH: 21
<212> TYPE: DNA
<213> ORGANISM: Artificial Sequence
<220> FEATURE:
<223> OTHER INFORMATION: Forward primer for Yb8NBC13, a human genetic
      marker that is useful for genetic detection for forensic or bio-
      ancestry studies.

<400> SEQUENCE: 113
tctggcaaat gctacccaag t                                            21
```

<210> SEQ ID NO 114
<211> LENGTH: 24
<212> TYPE: DNA
<213> ORGANISM: Artificial Sequence
<220> FEATURE:
<223> OTHER INFORMATION: Reverse primer for empty sequence for Yb8NBC13,
      a human genetic marker that is useful for genetic detection for
      forensic or bio-ancestry studies.

<400> SEQUENCE: 114
ggcatcttcc tcttcacatc ttat                                          24

<210> SEQ ID NO 115
<211> LENGTH: 21
<212> TYPE: DNA
<213> ORGANISM: Artificial Sequence
<220> FEATURE:
<223> OTHER INFORMATION: Reverse primer for filled sequence for
      Yb8NBC13, a human genetic marker that is useful for genetic
      detection for forensic or bio-ancestry studies.

<400> SEQUENCE: 115
ggcccctctt cacatcttat c                                             21

<210> SEQ ID NO 116
<211> LENGTH: 20
<212> TYPE: DNA
<213> ORGANISM: Artificial Sequence
<220> FEATURE:
<223> OTHER INFORMATION: Labeled forward primer for CHR20-79712, a
      humangenetic marker that is useful for genetic detection for
      forensic or bio-ancestry studies.  The "n" is to be replaced with
      a cytosine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 116
ntggacctct ccatccctat                                               20

<210> SEQ ID NO 117
<211> LENGTH: 20
<212> TYPE: DNA
<213> ORGANISM: Artificial Sequence
<220> FEATURE:
<223> OTHER INFORMATION: Forward primer for CHR20-79712, a human genetic
      marker that is useful for genetic detection for forensic or bio-
      ancestry studies.

<400> SEQUENCE: 117
ctggacctct ccatccctat                                               20

<210> SEQ ID NO 118
<211> LENGTH: 23
<212> TYPE: DNA
<213> ORGANISM: Artificial Sequence
<220> FEATURE:
<223> OTHER INFORMATION: Reverse primer for empty sequence for CHR20-
      79712, a human genetic marker that is useful for genetic detection
      for forensic or bio-ancestry studies.

<400> SEQUENCE: 118
agtttgcacg taagacagaa ttt                                           23

<210> SEQ ID NO 119
<211> LENGTH: 18
<212> TYPE: DNA
<213> ORGANISM: Artificial Sequence

```
<220> FEATURE:
<223> OTHER INFORMATION: Reverse primer for filled sequence for CHR20-
      79712, a human genetic marker that is useful for genetic detection
      for forensic or bio-ancestry studies.

<400> SEQUENCE: 119
ccggccaaga cagaattt                                                    18

<210> SEQ ID NO 120
<211> LENGTH: 20
<212> TYPE: DNA
<213> ORGANISM: Artificial Sequence
<220> FEATURE:
<223> OTHER INFORMATION: Labeled forward primer for CHR20-79712, a human
      genetic marker that is useful for genetic detection for forensic
      or bio-ancestry studies.  The "n" is to be replaced with an
      adenine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 120
ntttgcacag tgctccacac                                                  20

<210> SEQ ID NO 121
<211> LENGTH: 20
<212> TYPE: DNA
<213> ORGANISM: Artificial Sequence
<220> FEATURE:
<223> OTHER INFORMATION: Forward primer for CHR20-79712, a human genetic
      marker that is useful for genetic detection for forensic or bio-
      ancestry studies.

<400> SEQUENCE: 121
atttgcacag tgctccacac                                                  20

<210> SEQ ID NO 122
<211> LENGTH: 23
<212> TYPE: DNA
<213> ORGANISM: Artificial Sequence
<220> FEATURE:
<223> OTHER INFORMATION: Reverse primer for empty sequence for CHR20-
      79712, a human genetic marker that is useful for genetic detection
      for forensic or bio-ancestry studies.

<400> SEQUENCE: 122
gttgcacgta agacagaatt tga                                              23

<210> SEQ ID NO 123
<211> LENGTH: 20
<212> TYPE: DNA
<213> ORGANISM: Artificial Sequence
<220> FEATURE:
<223> OTHER INFORMATION: Reverse primer for filled sequence for CHR20-
      79712, a human genetic marker that is useful for genetic detection
      for forensic or bio-ancestry studies.

<400> SEQUENCE: 123
gcggccaaga cagaatttga                                                  20

<210> SEQ ID NO 124
<211> LENGTH: 25
<212> TYPE: DNA
<213> ORGANISM: Artificial Sequence
<220> FEATURE:
<223> OTHER INFORMATION: Reverse primer for empty sequence for CHR20-
      79712, a human genetic marker that is useful for genetic detection
      for forensic or bio-ancestry studies.
```

-continued

<400> SEQUENCE: 124
gttttgcacg taagacagaa tttga    25

<210> SEQ ID NO 125
<211> LENGTH: 18
<212> TYPE: DNA
<213> ORGANISM: Artificial Sequence
<220> FEATURE:
<223> OTHER INFORMATION: Reverse primer for filled sequence for CHR20-
      79712, a human genetic marker that is useful for genetic detection
      for forensic or bio-ancestry studies.

<400> SEQUENCE: 125
gcggccaaga cagaattt    18

<210> SEQ ID NO 126
<211> LENGTH: 20
<212> TYPE: DNA
<213> ORGANISM: Artificial Sequence
<220> FEATURE:
<223> OTHER INFORMATION: Labeled forward primer for Yb8AC1796, a human
      genetic marker that is useful for genetic detection for forensic
      or bio-ancestry studies. The "n" is to be replaced with a thymine
      labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 126
ngccagacag caaacaaata    20

<210> SEQ ID NO 127
<211> LENGTH: 20
<212> TYPE: DNA
<213> ORGANISM: Artificial Sequence
<220> FEATURE:
<223> OTHER INFORMATION: Forward primer for Yb8AC1796, a human genetic
      marker that is useful for genetic detection for forensic or bio-
      ancestry studies.

<400> SEQUENCE: 127
tgccagacag caaacaaata    20

<210> SEQ ID NO 128
<211> LENGTH: 24
<212> TYPE: DNA
<213> ORGANISM: Artificial Sequence
<220> FEATURE:
<223> OTHER INFORMATION: Reverse primer for empty sequence for
      Yb8AC1796, a human genetic marker that is useful for genetic
      detection for forensic or bio-ancestry studies.

<400> SEQUENCE: 128
gcaaggtcac aggtaggctt ttta    24

<210> SEQ ID NO 129
<211> LENGTH: 20
<212> TYPE: DNA
<213> ORGANISM: Artificial Sequence
<220> FEATURE:
<223> OTHER INFORMATION: Reverse primer for filled sequence for
      Yb8AC1796, a human genetic marker that is useful for genetic
      detection for forensic or bio-ancestry studies.

<400> SEQUENCE: 129
ggccacaggt aggcttttta    20

```
<210> SEQ ID NO 130
<211> LENGTH: 23
<212> TYPE: DNA
<213> ORGANISM: Artificial Sequence
<220> FEATURE:
<223> OTHER INFORMATION: Labeled forward primer for Yb8NBC106, a human
      genetic marker that is useful for genetic detection for forensic
      or bio-ancestry studies.  The "n" is to be replaced with a
      cytosine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 130
natcaaactc cagagttcct aag                                               23

<210> SEQ ID NO 131
<211> LENGTH: 23
<212> TYPE: DNA
<213> ORGANISM: Artificial Sequence
<220> FEATURE:
<223> OTHER INFORMATION: Forward primer for Yb8NBC106, a human genetic
      marker that is useful for genetic detection for forensic or bio-
      ancestry studies.

<400> SEQUENCE: 131
catcaaactc cagagttcct aag                                               23

<210> SEQ ID NO 132
<211> LENGTH: 22
<212> TYPE: DNA
<213> ORGANISM: Artificial Sequence
<220> FEATURE:
<223> OTHER INFORMATION: Reverse primer for empty sequence for
      Yb8NBC106, a human genetic marker that is useful for genetic
      detection for forensic or bio-ancestry studies.

<400> SEQUENCE: 132
gattgatgag gactcaggtt ga                                                22

<210> SEQ ID NO 133
<211> LENGTH: 20
<212> TYPE: DNA
<213> ORGANISM: Artificial Sequence
<220> FEATURE:
<223> OTHER INFORMATION: Reverse primer for filled sequence for
      Yb8NBC106, a human genetic marker that is useful for genetic
      detection for forensic or bio-ancestry studies.

<400> SEQUENCE: 133
ggattacagg cgtgaggatt                                                   20

<210> SEQ ID NO 134
<211> LENGTH: 25
<212> TYPE: DNA
<213> ORGANISM: Artificial Sequence
<220> FEATURE:
<223> OTHER INFORMATION: Labeled forward primer for Ya5-MLS09, a human
      genetic marker that is useful for genetic detection for forensic
      or bio-ancestry studies.  The "n" is to be replaced with an
      adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 134
ngcagatttc aggtcattat tgttt                                             25
```

```
<210> SEQ ID NO 135
<211> LENGTH: 25
<212> TYPE: DNA
<213> ORGANISM: Artificial Sequence
<220> FEATURE:
<223> OTHER INFORMATION: Forward primer for Ya5-MLS09, a human genetic
      marker that is useful for genetic detection for forensic or bio-
      ancestry studies.

<400> SEQUENCE: 135
agcagatttc aggtcattat tgttt                                           25

<210> SEQ ID NO 136
<211> LENGTH: 27
<212> TYPE: DNA
<213> ORGANISM: Artificial Sequence
<220> FEATURE:
<223> OTHER INFORMATION: Reverse primer for empty sequence for Ya5-
      MLS09, a human genetic marker that is useful for genetic detection
      for forensic or bio-ancestry studies.

<400> SEQUENCE: 136
tttctctcag agctatctca attttaa                                         27

<210> SEQ ID NO 137
<211> LENGTH: 19
<212> TYPE: DNA
<213> ORGANISM: Artificial Sequence
<220> FEATURE:
<223> OTHER INFORMATION: Reverse primer for filled sequence for Ya5-
      MLS09, a human genetic marker that is useful for genetic detection
      for forensic or bio-ancestry studies.

<400> SEQUENCE: 137
cggcctgcta tctcaattt                                                  19

<210> SEQ ID NO 138
<211> LENGTH: 29
<212> TYPE: DNA
<213> ORGANISM: Artificial Sequence
<220> FEATURE:
<223> OTHER INFORMATION: Reverse primer for empty sequence for Ya5-
      MLS09, a human genetic marker that is useful for genetic detection
      for forensic or bio-ancestry studies.

<400> SEQUENCE: 138
gtttctctca gaagctatct caattttaa                                       29

<210> SEQ ID NO 139
<211> LENGTH: 20
<212> TYPE: DNA
<213> ORGANISM: Artificial Sequence
<220> FEATURE:
<223> OTHER INFORMATION: Reverse primer for filled sequence for Ya5-
      MLS09, a human genetic marker that is useful for genetic detection
      for forensic or bio-ancestry studies.

<400> SEQUENCE: 139
gcggcctgct atctcaattt                                                 20

<210> SEQ ID NO 140
<211> LENGTH: 26
<212> TYPE: DNA
<213> ORGANISM: Artificial Sequence
<220> FEATURE:
<223> OTHER INFORMATION: Labeled forward primer for Ch22-Ya5533, a human
      genetic marker that is useful for genetic detection for forensic
      or bio-ancestry studies.  The "n" is to be replaced with an
      adenine labeled with 6-FAM dye.
```

```
<220> FEATURE:
<221> NAME/KEY: misc_feature
<222> LOCATION: (1)..(1)
<223> OTHER INFORMATION: n is a, c, g, or t

<400> SEQUENCE: 140
ngagaaaaac aaacatgtaa actgct                                         26

<210> SEQ ID NO 141
<211> LENGTH: 26
<212> TYPE: DNA
<213> ORGANISM: Artificial Sequence
<220> FEATURE:
<223> OTHER INFORMATION: Forward primer for Ch22-Ya5533, a human genetic
      marker that is useful for genetic detection for forensic or bio-
      ancestry studies.

<400> SEQUENCE: 141
agagaaaaac aaacatgtaa actgct                                         26

<210> SEQ ID NO 142
<211> LENGTH: 25
<212> TYPE: DNA
<213> ORGANISM: Artificial Sequence
<220> FEATURE:
<223> OTHER INFORMATION: Reverse primer for empty sequence for Ch22-
      Ya5533, a human genetic marker that is useful for genetic
      detection for forensic or bio-ancestry studies.

<400> SEQUENCE: 142
cggtcttgta aatcttaatt tgttg                                          25

<210> SEQ ID NO 143
<211> LENGTH: 25
<212> TYPE: DNA
<213> ORGANISM: Artificial Sequence
<220> FEATURE:
<223> OTHER INFORMATION: Reverse primer for filled sequence for Ch22-
      Ya5533, a human genetic marker that is useful for genetic
      detection for forensic or bio-ancestry studies.

<400> SEQUENCE: 143
aaagtgctgg gtaaatctta atttg                                          25

<210> SEQ ID NO 144
<211> LENGTH: 20
<212> TYPE: DNA
<213> ORGANISM: Artificial Sequence
<220> FEATURE:
<223> OTHER INFORMATION: Labeled forward primer for AC4027, a human
      genetic marker that is useful for genetic detection for forensic
      or bio-ancestry studies.  The "n" is to be replaced with an
      adenine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 144
naggtctaag cgcagtggaa                                                20

<210> SEQ ID NO 145
<211> LENGTH: 20
<212> TYPE: DNA
<213> ORGANISM: Artificial Sequence
<220> FEATURE:
<223> OTHER INFORMATION: Forward primer for AC4027, a human genetic
      marker that is useful for genetic detection for forensic or bio-
      ancestry studies.
```

<400> SEQUENCE: 145
aaggtctaag cgcagtggaa                                              20

<210> SEQ ID NO 146
<211> LENGTH: 27
<212> TYPE: DNA
<213> ORGANISM: Artificial Sequence
<220> FEATURE:
<223> OTHER INFORMATION: Reverse primer for empty sequence for AC4027, a
      human genetic marker that is useful for genetic detection for
      forensic or bio-ancestry studies.

<400> SEQUENCE: 146
tgtgttttgt acagagttct taattgc                                      27

<210> SEQ ID NO 147
<211> LENGTH: 18
<212> TYPE: DNA
<213> ORGANISM: Artificial Sequence
<220> FEATURE:
<223> OTHER INFORMATION: Reverse primer for filled sequence for AC4027,
      a human genetic marker that is useful for genetic detection for
      forensic or bio-ancestry studies.

<400> SEQUENCE: 147
ccggcccaga gttcttaa                                                18

<210> SEQ ID NO 148
<211> LENGTH: 20
<212> TYPE: DNA
<213> ORGANISM: Artificial Sequence
<220> FEATURE:
<223> OTHER INFORMATION: Labeled forward primer for AC4027, a human
      genetic marker that is useful for genetic detection for forensic
      or bio-ancestry studies.  The "n" is to be replaced with an
      adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 148
naggtctaag cgcagtggaa                                              20

<210> SEQ ID NO 149
<211> LENGTH: 26
<212> TYPE: DNA
<213> ORGANISM: Artificial Sequence
<220> FEATURE:
<223> OTHER INFORMATION: Reverse primer for empty sequence for AC4027, a
      human genetic marker that is useful for genetic detection for
      forensic or bio-ancestry studies.

<400> SEQUENCE: 149
gtgttttgta cagagttctt aattgc                                       26

<210> SEQ ID NO 150
<211> LENGTH: 20
<212> TYPE: DNA
<213> ORGANISM: Artificial Sequence
<220> FEATURE:
<223> OTHER INFORMATION: Reverse primer for filled sequence for AC4027,
      a human genetic marker that is useful for genetic detection for
      forensic or bio-ancestry studies.

<400> SEQUENCE: 150
ggcccagagt tcttaattgc                                              20

```
<210> SEQ ID NO 151
<211> LENGTH: 23
<212> TYPE: DNA
<213> ORGANISM: Artificial Sequence
<220> FEATURE:
<223> OTHER INFORMATION: Labeled forward primer for Amelogenin, a human
      genetic marker that is useful for genetic detection for forensic
      or bio-ancestry studies.  The "n" is to be replaced with a
      cytosine labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 151
ncctttgaag tggtaccaga gca                                              23

<210> SEQ ID NO 152
<211> LENGTH: 23
<212> TYPE: DNA
<213> ORGANISM: Artificial Sequence
<220> FEATURE:
<223> OTHER INFORMATION: Forward primer for Amelogenin, a human genetic
      marker that is useful for genetic detection for forensic or bio-
      ancestry studies.

<400> SEQUENCE: 152
ccctttgaag tggtaccaga gca                                              23

<210> SEQ ID NO 153
<211> LENGTH: 25
<212> TYPE: DNA
<213> ORGANISM: Artificial Sequence
<220> FEATURE:
<223> OTHER INFORMATION: Reverse primer for empty sequence for
      Amelogenin, a human genetic marker that is useful for genetic
      detection for forensic or bio-ancestry studies.

<400> SEQUENCE: 153
gcatgcctaa tattttcagg gaata                                            25

<210> SEQ ID NO 154
<211> LENGTH: 19
<212> TYPE: DNA
<213> ORGANISM: Artificial Sequence
<220> FEATURE:
<223> OTHER INFORMATION: Labeled forward primer for Amelogenin, a human
      genetic marker that is useful for genetic detection for forensic
      or bio-ancestry studies.  The "n" is to be replaced with a
      cytosine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 154
ncctttgaag tggtaccag                                                   19

<210> SEQ ID NO 155
<211> LENGTH: 19
<212> TYPE: DNA
<213> ORGANISM: Artificial Sequence
<220> FEATURE:
<223> OTHER INFORMATION: Forward primer for Amelogenin, a human genetic
      marker that is useful for genetic detection for forensic or bio-
      ancestry studies.

<400> SEQUENCE: 155
ccctttgaag tggtaccag                                                   19
```

```
<210> SEQ ID NO 156
<211> LENGTH: 22
<212> TYPE: DNA
<213> ORGANISM: Artificial Sequence
<220> FEATURE:
<223> OTHER INFORMATION: Labeled forward primer for Yc1RG148, a human
      genetic marker that is useful for genetic detection for forensic
      or bio-ancestry studies.  The "n" is to be replaced with an
      adenine labeled with JOE dye.
<220> FEATURE:
<221> NAME/KEY: misc_feature
<222> LOCATION: (1)..(1)
<223> OTHER INFORMATION: n is a, c, g, or t

<400> SEQUENCE: 156
nacacgttct gaaacatcca tc                                             22

<210> SEQ ID NO 157
<211> LENGTH: 22
<212> TYPE: DNA
<213> ORGANISM: Artificial Sequence
<220> FEATURE:
<223> OTHER INFORMATION: Forward primer for Yc1RG148, a human genetic
      marker that is useful for genetic detection for forensic or bio-
      ancestry studies.

<400> SEQUENCE: 157
aacacgttct gaaacatcca tc                                             22

<210> SEQ ID NO 158
<211> LENGTH: 26
<212> TYPE: DNA
<213> ORGANISM: Artificial Sequence
<220> FEATURE:
<223> OTHER INFORMATION: Reverse primer for empty sequence for Yc1RG148,
      a human genetic marker that is useful for genetic detection for
      forensic or bio-ancestry studies.

<400> SEQUENCE: 158
tttcatattt atttttgctt gtttgt                                         26

<210> SEQ ID NO 159
<211> LENGTH: 18
<212> TYPE: DNA
<213> ORGANISM: Artificial Sequence
<220> FEATURE:
<223> OTHER INFORMATION: Reverse primer for filled sequence for
      Yc1RG148, a human genetic marker that is useful for genetic
      detection for forensic or bio-ancestry studies.

<400> SEQUENCE: 159
ccggcctgct tgtttgtt                                                  18

<210> SEQ ID NO 160
<211> LENGTH: 20
<212> TYPE: DNA
<213> ORGANISM: Artificial Sequence
<220> FEATURE:
<223> OTHER INFORMATION: Labeled forward primer for SVA306, a human
      genetic marker that is useful for genetic detection for forensic
      or bio-ancestry studies.  The "n" is to be replaced with a thymine
      labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 160
nggaggcctc tgctattttc                                                20
```

```
<210> SEQ ID NO 161
<211> LENGTH: 20
<212> TYPE: DNA
<213> ORGANISM: Artificial Sequence
<220> FEATURE:
<223> OTHER INFORMATION: Forward primer for SVA306, a human genetic
      marker that is useful for genetic detection for forensic or bio-
      ancestry studies.

<400> SEQUENCE: 161
tggaggcctc tgctattttc                                                   20

<210> SEQ ID NO 162
<211> LENGTH: 27
<212> TYPE: DNA
<213> ORGANISM: Artificial Sequence
<220> FEATURE:
<223> OTHER INFORMATION: Reverse primer for empty sequence for SVA306, a
      human genetic marker that is useful for genetic detection for
      forensic or bio-ancestry studies.

<400> SEQUENCE: 162
gaagggttca ttaaagaatt ttcatag                                           27

<210> SEQ ID NO 163
<211> LENGTH: 20
<212> TYPE: DNA
<213> ORGANISM: Artificial Sequence
<220> FEATURE:
<223> OTHER INFORMATION: Reverse primer for filled sequence for SVA306,
      a human genetic marker that is useful for genetic detection for
      forensic or bio-ancestry studies.

<400> SEQUENCE: 163
gagagggaga gggacaagaa                                                   20

<210> SEQ ID NO 164
<211> LENGTH: 22
<212> TYPE: DNA
<213> ORGANISM: Artificial Sequence
<220> FEATURE:
<223> OTHER INFORMATION: Labeled forward primer for SVA323, a human
      genetic marker that is useful for genetic detection for forensic
      or bio-ancestry studies.  The "n" is to be replaced with a thymine
      labeled with TMR dye.
<220> FEATURE:
<221> NAME/KEY: misc_feature
<222> LOCATION: (1)..(1)
<223> OTHER INFORMATION: n is a, c, g, or t

<400> SEQUENCE: 164
ngtgcttcat ttgagaaagc tg                                                22

<210> SEQ ID NO 165
<211> LENGTH: 22
<212> TYPE: DNA
<213> ORGANISM: Artificial Sequence
<220> FEATURE:
<223> OTHER INFORMATION: Forward primer for SVA323, a human genetic
      marker that is useful for genetic detection for forensic or bio-
      ancestry studies.

<400> SEQUENCE: 165
tgtgcttcat ttgagaaagc tg                                                22

<210> SEQ ID NO 166
<211> LENGTH: 21
<212> TYPE: DNA
<213> ORGANISM: Artificial Sequence
```

```
<220> FEATURE:
<223> OTHER INFORMATION: Reverse primer for empty sequence for SVA323, a
      human genetic marker that is useful for genetic detection for
      forensic or bio-ancestry studies.

<400> SEQUENCE: 166
gctggccgga agtcttaatg c                                              21

<210> SEQ ID NO 167
<211> LENGTH: 26
<212> TYPE: DNA
<213> ORGANISM: Artificial Sequence
<220> FEATURE:
<223> OTHER INFORMATION: Reverse primer for filled sequence for SVA323,
      a human genetic marker that is useful for genetic detection for
      forensic or bio-ancestry studies.

<400> SEQUENCE: 167
gttgaaggat agaagtctta atgcag                                         26

<210> SEQ ID NO 168
<211> LENGTH: 20
<212> TYPE: DNA
<213> ORGANISM: Artificial Sequence
<220> FEATURE:
<223> OTHER INFORMATION: Labeled forward primer for Ya5-MLS26, a human
      genetic marker that is useful for genetic detection for forensic
      or bio-ancestry studies.  The "n" is to be replaced with an
      adenine labeled with 6-FAM dye.
<220> FEATURE:
<221> NAME/KEY: misc_feature
<222> LOCATION: (1)..(1)
<223> OTHER INFORMATION: n is a, c, g, or t

<400> SEQUENCE: 168
ngggaagcca aaagattgga                                                20

<210> SEQ ID NO 169
<211> LENGTH: 20
<212> TYPE: DNA
<213> ORGANISM: Artificial Sequence
<220> FEATURE:
<223> OTHER INFORMATION: Forward primer for Ya5-MLS26, a human genetic
      marker that is useful for genetic detection for forensic or bio-
      ancestry studies.

<400> SEQUENCE: 169
agggaagcca aaagattgga                                                20

<210> SEQ ID NO 170
<211> LENGTH: 25
<212> TYPE: DNA
<213> ORGANISM: Artificial Sequence
<220> FEATURE:
<223> OTHER INFORMATION: Reverse primer for empty sequence for Ya5-
      MLS26, a human genetic marker that is useful for genetic detection
      for forensic or bio-ancestry studies.

<400> SEQUENCE: 170
ttgtgcctct tacattttct tttta                                          25

<210> SEQ ID NO 171
<211> LENGTH: 19
<212> TYPE: DNA
<213> ORGANISM: Artificial Sequence
<220> FEATURE:
<223> OTHER INFORMATION: Reverse primer for filled sequence for Ya5-
      MLS26, a human genetic marker that is useful for genetic detection
      for forensic or bio-ancestry studies.
```

<400> SEQUENCE: 171
ccggcctaca ttttctttt                                                     19

<210> SEQ ID NO 172
<211> LENGTH: 22
<212> TYPE: DNA
<213> ORGANISM: Artificial Sequence
<220> FEATURE:
<223> OTHER INFORMATION: Labeled forward primer for Yb9NBC10, a human
      genetic marker that is useful for genetic detection for forensic
      or bio-ancestry studies.  The "n" is to be replaced with a thymine
      labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 172
ntgccacttt catttctatt gc                                                 22

<210> SEQ ID NO 173
<211> LENGTH: 22
<212> TYPE: DNA
<213> ORGANISM: Artificial Sequence
<220> FEATURE:
<223> OTHER INFORMATION: Forward primer for Yb9NBC10, a human genetic
      marker that is useful for genetic detection for forensic or bio-
      ancestry studies.

<400> SEQUENCE: 173
ttgccacttt catttctatt gc                                                 22

<210> SEQ ID NO 174
<211> LENGTH: 22
<212> TYPE: DNA
<213> ORGANISM: Artificial Sequence
<220> FEATURE:
<223> OTHER INFORMATION: Reverse primer for empty sequence for Yb9NBC10,
      a human genetic marker that is useful for genetic detection for
      forensic or bio-ancestry studies.

<400> SEQUENCE: 174
cattcaaatg gtctttttcc tt                                                 22

<210> SEQ ID NO 175
<211> LENGTH: 20
<212> TYPE: DNA
<213> ORGANISM: Artificial Sequence
<220> FEATURE:
<223> OTHER INFORMATION: Reverse primer for filled sequence for
      Yb9NBC10, a human genetic marker that is useful for genetic
      detection for forensic or bio-ancestry studies.

<400> SEQUENCE: 175 cggcccttttt tcctttctta                                                   20

<210> SEQ ID NO 176
<211> LENGTH: 22
<212> TYPE: DNA
<213> ORGANISM: Artificial Sequence
<220> FEATURE:
<223> OTHER INFORMATION: Labeled forward primer for Ya5NBC216, a human
      genetic marker that is useful for genetic detection for forensic
      or bio-ancestry studies.  The "n" is to be replaced with a thymine
      labeled with 6-FAM dye.
<220> FEATURE:
<221> NAME/KEY: misc_feature
<222> LOCATION: (1)..(1)
<223> OTHER INFORMATION: n is a, c, g, or t

```
<400> SEQUENCE: 176
ngaatgaaga aacttggcac tc                                          22

<210> SEQ ID NO 177
<211> LENGTH: 22
<212> TYPE: DNA
<213> ORGANISM: Artificial Sequence
<220> FEATURE:
<223> OTHER INFORMATION: Forward primer for Ya5NBC216, a human genetic
      marker that is useful for genetic detection for forensic or bio-
      ancestry studies.

<400> SEQUENCE: 177
tgaatgaaga aacttggcac tc                                          22

<210> SEQ ID NO 178
<211> LENGTH: 23
<212> TYPE: DNA
<213> ORGANISM: Artificial Sequence
<220> FEATURE:
<223> OTHER INFORMATION: Reverse primer for empty sequence for
      Ya5NBC216, a human genetic marker that is useful for genetic
      detection for forensic or bio-ancestry studies.

<400> SEQUENCE: 178
ggtatgctgg tactctgtgt ctg                                         23

<210> SEQ ID NO 179
<211> LENGTH: 19
<212> TYPE: DNA
<213> ORGANISM: Artificial Sequence
<220> FEATURE:
<223> OTHER INFORMATION: Reverse primer for filled sequence for
      Ya5NBC216, a human genetic marker that is useful for genetic
      detection for forensic or bio-ancestry studies.

<400> SEQUENCE: 179
gcccggccgt ctgtatgtt                                              19

<210> SEQ ID NO 180
<211> LENGTH: 20
<212> TYPE: DNA
<213> ORGANISM: Artificial Sequence
<220> FEATURE:
<223> OTHER INFORMATION: Labeled forward primer for Ya5ACA1766, a human
      genetic marker that is useful for genetic detection for forensic
      or bio-ancestry studies.  The "n" is to be replaced with a thymine
      labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 180
nccttgagca caaagaccaa                                             20

<210> SEQ ID NO 181
<211> LENGTH: 20
<212> TYPE: DNA
<213> ORGANISM: Artificial Sequence
<220> FEATURE:
<223> OTHER INFORMATION: Forward primer for Ya5ACA1766, a human genetic
      marker that is useful for genetic detection for forensic or bio-
      ancestry studies.

<400> SEQUENCE: 181
tccttgagca caaagaccaa                                             20
```

-continued

<210> SEQ ID NO 182
<211> LENGTH: 25
<212> TYPE: DNA
<213> ORGANISM: Artificial Sequence
<220> FEATURE:
<223> OTHER INFORMATION: Reverse primer for empty sequence for
     Ya5ACA1766, a human genetic marker that is useful for genetic
     detection for forensic or bio-ancestry studies.

<400> SEQUENCE: 182
ggtactctgg aagacactgt cctaa                                        25

<210> SEQ ID NO 183
<211> LENGTH: 18
<212> TYPE: DNA
<213> ORGANISM: Artificial Sequence
<220> FEATURE:
<223> OTHER INFORMATION: Reverse primer for filled sequence for
     Ya5ACA1766, a human genetic marker that is useful for genetic
     detection for forensic or bio-ancestry studies.

<400> SEQUENCE: 183
cggccgacac tgtcctaa                                                18

<210> SEQ ID NO 184
<211> LENGTH: 19
<212> TYPE: DNA
<213> ORGANISM: Artificial Sequence
<220> FEATURE:
<223> OTHER INFORMATION: Reverse primer for filled sequence for
     Ya5ACA1766, a human genetic marker that is useful for genetic
     detection for forensic or bio-ancestry studies.

<400> SEQUENCE: 184
gcggccgaca ctgtcctaa                                               19

<210> SEQ ID NO 185
<211> LENGTH: 23
<212> TYPE: DNA
<213> ORGANISM: Artificial Sequence
<220> FEATURE:
<223> OTHER INFORMATION: Labeled forward primer for Yb8NBC148, a human
     genetic marker that is useful for genetic detection for forensic
     or bio-ancestry studies.  The "n" is to be replaced with a
     cytosine labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 185
ncttggtgat cttatccact tgt                                          23

<210> SEQ ID NO 186
<211> LENGTH: 23
<212> TYPE: DNA
<213> ORGANISM: Artificial Sequence
<220> FEATURE:
<223> OTHER INFORMATION: Forward primer for Yb8NBC148, a human genetic
     marker that is useful for genetic detection for forensic or bio-
     ancestry studies.

<400> SEQUENCE: 186
ccttggtgat cttatccact tgt                                          23

<210> SEQ ID NO 187
<211> LENGTH: 19
<212> TYPE: DNA
<213> ORGANISM: Artificial Sequence

```
<220> FEATURE:
<223> OTHER INFORMATION: Reverse primer for empty sequence for
      Yb8NBC148, a human genetic marker that is useful for genetic
      detection for forensic or bio-ancestry studies.

<400> SEQUENCE: 187
gacggcagtc aagcagtgt                                                  19

<210> SEQ ID NO 188
<211> LENGTH: 18
<212> TYPE: DNA
<213> ORGANISM: Artificial Sequence
<220> FEATURE:
<223> OTHER INFORMATION: Reverse primer for filled sequence for
      Yb8NBC148, a human genetic marker that is useful for genetic
      detection for forensic or bio-ancestry studies.

<400> SEQUENCE: 188
cggcccaagc agtgtttt                                                   18

<210> SEQ ID NO 189
<211> LENGTH: 22
<212> TYPE: DNA
<213> ORGANISM: Artificial Sequence
<220> FEATURE:
<223> OTHER INFORMATION: Labeled forward primer for Ya5NBC102, a human
      genetic marker that is useful for genetic detection for forensic
      or bio-ancestry studies.  The "n" is to be replaced with a thymine
      labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 189
nagctcacct ctgcttgtaa gg                                              22

<210> SEQ ID NO 190
<211> LENGTH: 22
<212> TYPE: DNA
<213> ORGANISM: Artificial Sequence
<220> FEATURE:
<223> OTHER INFORMATION: Forward primer for Ya5NBC102, a human genetic
      marker that is useful for genetic detection for forensic or bio-
      ancestry studies.

<400> SEQUENCE: 190
tagctcacct ctgcttgtaa gg                                              22

<210> SEQ ID NO 191
<211> LENGTH: 24
<212> TYPE: DNA
<213> ORGANISM: Artificial Sequence
<220> FEATURE:
<223> OTHER INFORMATION: Reverse primer for empty sequence for
      Ya5NBC102, a human genetic marker that is useful for genetic
      detection for forensic or bio-ancestry studies.

<400> SEQUENCE: 191
gacctgctgc ctatacagtc actt                                            24

<210> SEQ ID NO 192
<211> LENGTH: 23
<212> TYPE: DNA
<213> ORGANISM: Artificial Sequence
<220> FEATURE:
<223> OTHER INFORMATION: Reverse primer for filled sequence for
      Ya5NBC102, a human genetic marker that is useful for genetic
      detection for forensic or bio-ancestry studies.
```

-continued

<400> SEQUENCE: 192
ggattacagg cgtgatacag tca                                            23

<210> SEQ ID NO 193
<211> LENGTH: 26
<212> TYPE: DNA
<213> ORGANISM: Artificial Sequence
<220> FEATURE:
<223> OTHER INFORMATION: Labeled forward primer for SB19.12, a human
      genetic marker that is useful for genetic detection for forensic
      or bio-ancestry studies. The "n" is to be replaced with a guanine
      labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 193
nagactagaa tgatgaagaa acctga                                         26

<210> SEQ ID NO 194
<211> LENGTH: 26
<212> TYPE: DNA
<213> ORGANISM: Artificial Sequence
<220> FEATURE:
<223> OTHER INFORMATION: Forward primer for SB19.12, a human genetic
      marker that is useful for genetic detection for forensic or bio-
      ancestry studies.

<400> SEQUENCE: 194
gagactagaa tgatgaagaa acctga                                         26

<210> SEQ ID NO 195
<211> LENGTH: 20
<212> TYPE: DNA
<213> ORGANISM: Artificial Sequence
<220> FEATURE:
<223> OTHER INFORMATION: Reverse primer for empty sequence for SB19.12,
      a human genetic marker that is useful for genetic detection for
      forensic or bio-ancestry studies.

<400> SEQUENCE: 195
gctcactgca accctctgta                                                20

<210> SEQ ID NO 196
<211> LENGTH: 18
<212> TYPE: DNA
<213> ORGANISM: Artificial Sequence
<220> FEATURE:
<223> OTHER INFORMATION: Reverse primer for filled sequence for SB19.12,
      a human genetic marker that is useful for genetic detection for
      forensic or bio-ancestry studies.

<400> SEQUENCE: 196
gcccggccct ctgtattt                                                  18

<210> SEQ ID NO 197
<211> LENGTH: 21
<212> TYPE: DNA
<213> ORGANISM: Artificial Sequence
<220> FEATURE:
<223> OTHER INFORMATION: Labeled forward primer for Yb8NBC120, a human
      genetic marker that is useful for genetic detection for forensic
      or bio-ancestry studies. The "n" is to be replaced with a guanine
      labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 197
naaagtggca attgattttg g    21

<210> SEQ ID NO 198
<211> LENGTH: 21
<212> TYPE: DNA
<213> ORGANISM: Artificial Sequence
<220> FEATURE:
<223> OTHER INFORMATION: Forward primer for Yb8NBC120, a human genetic
      marker that is useful for genetic detection for forensic or bio-
      ancestry studies.

<400> SEQUENCE: 198
gaaagtggca attgattttg g    21

<210> SEQ ID NO 199
<211> LENGTH: 27
<212> TYPE: DNA
<213> ORGANISM: Artificial Sequence
<220> FEATURE:
<223> OTHER INFORMATION: Reverse primer for empty sequence for
      Yb8NBC120, a human genetic marker that is useful for genetic
      detection for forensic or bio-ancestry studies.

<400> SEQUENCE: 199
ttttacctct ctatccttgc ttttata    27

<210> SEQ ID NO 200
<211> LENGTH: 19
<212> TYPE: DNA
<213> ORGANISM: Artificial Sequence
<220> FEATURE:
<223> OTHER INFORMATION: Reverse primer for filled sequence for
      Yb8NBC120, a human genetic marker that is useful for genetic
      detection for forensic or bio-ancestry studies.

<400> SEQUENCE: 200
cggccttatc cttgctttt    19

<210> SEQ ID NO 201
<211> LENGTH: 21
<212> TYPE: DNA
<213> ORGANISM: Artificial Sequence
<220> FEATURE:
<223> OTHER INFORMATION: Labeled forward primer for CH1-2250, a human
      genetic marker that is useful for genetic detection for forensic
      or bio-ancestry studies.  The "n" is to be replaced with a thymine
      labeled with ROX dye.
<220> FEATURE:
<221> NAME/KEY: misc_feature
<222> LOCATION: (1)..(1)
<223> OTHER INFORMATION: n is a, c, g, or t

<400> SEQUENCE: 201
nggacctgtg cagttcaaac c    21

<210> SEQ ID NO 202
<211> LENGTH: 23
<212> TYPE: DNA
<213> ORGANISM: Artificial Sequence
<220> FEATURE:
<223> OTHER INFORMATION: Reverse primer for empty sequence for CH1-2250,
      a human genetic marker that is useful for genetic detection for
      forensic or bio-ancestry studies.

<400> SEQUENCE: 202
gcccaaaggt ttgatttcaa gtt    23

<210> SEQ ID NO 203
<211> LENGTH: 21
<212> TYPE: DNA
<213> ORGANISM: Artificial Sequence
<220> FEATURE:
<223> OTHER INFORMATION: Reverse primer for filled sequence for CH1-
      2250, a human genetic marker that is useful for genetic detection
      for forensic or bio-ancestry studies.

<400> SEQUENCE: 203
gccggccttg atttcaagtt t                                          21

<210> SEQ ID NO 204
<211> LENGTH: 21
<212> TYPE: DNA
<213> ORGANISM: Artificial Sequence
<220> FEATURE:
<223> OTHER INFORMATION: Labeled forward primer for Yb8AC1197, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 204
ngctgccctt aatctttacc a                                          21

<210> SEQ ID NO 205
<211> LENGTH: 21
<212> TYPE: DNA
<213> ORGANISM: Artificial Sequence
<220> FEATURE:
<223> OTHER INFORMATION: Forward primer for Yb8AC1197, a human genetic
      marker that is useful for genetic detection for forensic or bio-
      ancestry studies.

<400> SEQUENCE: 205
tgctgccctt aatctttacc a                                          21

<210> SEQ ID NO 206
<211> LENGTH: 26
<212> TYPE: DNA
<213> ORGANISM: Artificial Sequence
<220> FEATURE:
<223> OTHER INFORMATION: Reverse primer for empty sequence for CHR20-
      79712, a human genetic marker that is useful for genetic detection
      for forensic or bio-ancestry studies.

<400> SEQUENCE: 206
gagactttca tttctaagat gtctgg                                     26

<210> SEQ ID NO 207
<211> LENGTH: 19
<212> TYPE: DNA
<213> ORGANISM: Artificial Sequence
<220> FEATURE:
<223> OTHER INFORMATION: Reverse primer for filled sequence for
      Yb8AC1197, a human genetic marker that is useful for genetic
      detection for forensic or bio-ancestry studies.

<400> SEQUENCE: 207
cccggccttc atttctaag                                             19

<210> SEQ ID NO 208
<211> LENGTH: 20
<212> TYPE: DNA
<213> ORGANISM: Artificial Sequence

```
<220> FEATURE:
<223> OTHER INFORMATION: Labeled forward primer for Yb8AC1439, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 208
ngctgagctc catgctattc                                                   20

<210> SEQ ID NO 209
<211> LENGTH: 20
<212> TYPE: DNA
<213> ORGANISM: Artificial Sequence
<220> FEATURE:
<223> OTHER INFORMATION: Forward primer for Yb8AC1439, a human genetic
      marker that is useful for genetic detection for forensic or bio-
      ancestry studies.

<400> SEQUENCE: 209
tgctgagctc catgctattc                                                   20

<210> SEQ ID NO 210
<211> LENGTH: 20
<212> TYPE: DNA
<213> ORGANISM: Artificial Sequence
<220> FEATURE:
<223> OTHER INFORMATION: Reverse primer for empty sequence for
      Yb8AC1439, a human genetic marker that is useful for genetic
      detection for forensic or bio-ancestry studies.

<400> SEQUENCE: 210
gctcaccagc tcttgacgta                                                   20

<210> SEQ ID NO 211
<211> LENGTH: 20
<212> TYPE: DNA
<213> ORGANISM: Artificial Sequence
<220> FEATURE:
<223> OTHER INFORMATION: Reverse primer for filled sequence for
      Yb8AC1439, a human genetic marker that is useful for genetic
      detection for forensic or bio-ancestry studies.

<400> SEQUENCE: 211
agacggggta ccagctcttg                                                   20

<210> SEQ ID NO 212
<211> LENGTH: 20
<212> TYPE: DNA
<213> ORGANISM: Artificial Sequence
<220> FEATURE:
<223> OTHER INFORMATION: Labeled forward primer for Yb8NBC69, a human
      genetic marker that is useful for genetic detection for forensic
      or bio-ancestry studies.  The "n" is to be replaced with an
      adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 212
naatggtgct gggatagctg                                                   20
```

<210> SEQ ID NO 213
<211> LENGTH: 20
<212> TYPE: DNA
<213> ORGANISM: Artificial Sequence
<220> FEATURE:
<223> OTHER INFORMATION: Forward primer for Yb8NBC69, a human genetic
      marker that is useful for genetic detection for forensic or bio-
      ancestry studies.

<400> SEQUENCE: 213
aaatggtgct gggatagctg                                            20

<210> SEQ ID NO 214
<211> LENGTH: 26
<212> TYPE: DNA
<213> ORGANISM: Artificial Sequence
<220> FEATURE:
<223> OTHER INFORMATION: Reverse primer for empty sequence for
      Yb8NBC69, a human genetic marker that is useful for genetic
      detection for forensic or bio-ancestry studies.

<400> SEQUENCE: 214
ataagaattc cagaagaaaa cctagg                                     26

<210> SEQ ID NO 215
<211> LENGTH: 18
<212> TYPE: DNA
<213> ORGANISM: Artificial Sequence
<220> FEATURE:
<223> OTHER INFORMATION: Reverse primer for filled sequence for
      Yb8NBC69, a human genetic marker that is useful for genetic
      detection for forensic or bio-ancestry studies.

<400> SEQUENCE: 215
ataagaattc cggccggg                                              18

<210> SEQ ID NO 216
<211> LENGTH: 20
<212> TYPE: DNA
<213> ORGANISM: Artificial Sequence
<220> FEATURE:
<223> OTHER INFORMATION: Labeled forward primer for Yb8NBC126, a human
      genetic marker that is useful for genetic detection for forensic
      or bio-ancestry studies.  The "n" is to be replaced with an
      adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 216
ngctcctgga aagggaaag                                             20

<210> SEQ ID NO 217
<211> LENGTH: 20
<212> TYPE: DNA
<213> ORGANISM: Artificial Sequence
<220> FEATURE:
<223> OTHER INFORMATION: Forward primer for Yb8NBC126, a human genetic
      marker that is useful for genetic detection for forensic or bio-
      ancestry studies.

<400> SEQUENCE: 217
agctcctgga aagggaaag                                             20

<210> SEQ ID NO 218
<211> LENGTH: 20
<212> TYPE: DNA
<213> ORGANISM: Artificial Sequence

```
<220> FEATURE:
<223> OTHER INFORMATION: Reverse primer for empty sequence for
      Yb8NBC126, a human genetic marker that is useful for genetic
      detection for forensic or bio-ancestry studies.

<400> SEQUENCE: 218
atgatgattg gggcacctta                                                  20

<210> SEQ ID NO 219
<211> LENGTH: 19
<212> TYPE: DNA
<213> ORGANISM: Artificial Sequence
<220> FEATURE:
<223> OTHER INFORMATION: Reverse primer for filled sequence for
      Yb8NBC126, a human genetic marker that is useful for genetic
      detection for forensic or bio-ancestry studies.

<400> SEQUENCE: 219
atccgattgg ggcacctta                                                   19

<210> SEQ ID NO 220
<211> LENGTH: 26
<212> TYPE: DNA
<213> ORGANISM: Artificial Sequence
<220> FEATURE:
<223> OTHER INFORMATION: Labeled forward primer for Yb8NBC622, a human
      genetic marker that is useful for genetic detection for forensic
      or bio-ancestry studies.  The "n" is to be replaced with a guanine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 220
ngaatacaat gtaactgggg atatgc                                           26

<210> SEQ ID NO 221
<211> LENGTH: 26
<212> TYPE: DNA
<213> ORGANISM: Artificial Sequence
<220> FEATURE:
<223> OTHER INFORMATION: Forward primer for Yb8NBC622, a human genetic
      marker that is useful for genetic detection for forensic or bio-
      ancestry studies.

<400> SEQUENCE: 221
ggaatacaat gtaactgggg atatgc                                           26

<210> SEQ ID NO 222
<211> LENGTH: 22
<212> TYPE: DNA
<213> ORGANISM: Artificial Sequence
<220> FEATURE:
<223> OTHER INFORMATION: Reverse primer for empty sequence for
      Yb8NBC622, a human genetic marker that is useful for genetic
      detection for forensic or bio-ancestry studies.

<400> SEQUENCE: 222
tgtgcagggg aattccttct aa                                               22

<210> SEQ ID NO 223
<211> LENGTH: 18
<212> TYPE: DNA
<213> ORGANISM: Artificial Sequence
<220> FEATURE:
<223> OTHER INFORMATION: Reverse primer for filled sequence for
      Yb8NBC622, a human genetic marker that is useful for genetic
      detection for forensic or bio-ancestry studies.
```

-continued

<400> SEQUENCE: 223
gcgcaatctc ggctcctt                                                    18

<210> SEQ ID NO 224
<211> LENGTH: 21
<212> TYPE: DNA
<213> ORGANISM: Artificial Sequence
<220> FEATURE:
<223> OTHER INFORMATION: Labeled forward primer for Ya5ACA1153, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 224
ncgtggaggt acagtggata a                                                21

<210> SEQ ID NO 225
<211> LENGTH: 21
<212> TYPE: DNA
<213> ORGANISM: Artificial Sequence
<220> FEATURE:
<223> OTHER INFORMATION: Forward primer for Ya5ACA1153, a human genetic
      marker that is useful for genetic detection for forensic or bio-
      ancestry studies.

<400> SEQUENCE: 225
tcgtggaggt acagtggata a                                                21

<210> SEQ ID NO 226
<211> LENGTH: 26
<212> TYPE: DNA
<213> ORGANISM: Artificial Sequence
<220> FEATURE:
<223> OTHER INFORMATION: Reverse primer for empty sequence for
      Ya5ACA1153, a human genetic marker that is useful for genetic
      detection for forensic or bio-ancestry studies.

<400> SEQUENCE: 226
tgtccttctg tgtcttctta aatatc                                           26

<210> SEQ ID NO 227
<211> LENGTH: 18
<212> TYPE: DNA
<213> ORGANISM: Artificial Sequence
<220> FEATURE:
<223> OTHER INFORMATION: Reverse primer for filled sequence for
      Ya5ACA1153, a human genetic marker that is useful for genetic
      detection for forensic or bio-ancestry studies.

<400> SEQUENCE: 227
ccggccctgt gtcttctt                                                    18

<210> SEQ ID NO 228
<211> LENGTH: 21
<212> TYPE: DNA
<213> ORGANISM: Artificial Sequence
<220> FEATURE:
<223> OTHER INFORMATION: Labeled forward primer for Yb8NBC18, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t -continued

<400> SEQUENCE: 228
ngcatacgtg tgtcttcatg t                                              21

<210> SEQ ID NO 229
<211> LENGTH: 21
<212> TYPE: DNA
<213> ORGANISM: Artificial Sequence
<220> FEATURE:
<223> OTHER INFORMATION: Forward primer for Yb8NBC18, a human genetic
      marker that is useful for genetic detection for forensic or bio-
      ancestry studies.

<400> SEQUENCE: 229
tgcatacgtg tgtcttcatg t                                              21

<210> SEQ ID NO 230
<211> LENGTH: 22
<212> TYPE: DNA
<213> ORGANISM: Artificial Sequence
<220> FEATURE:
<223> OTHER INFORMATION: Reverse primer for empty sequence for Yb8NBC18,
      a human genetic marker that is useful for genetic detection for
      forensic or bio-ancestry studies.

<400> SEQUENCE: 230
aggaatcgcg tctcctatct ga                                             22

<210> SEQ ID NO 231
<211> LENGTH: 18
<212> TYPE: DNA
<213> ORGANISM: Artificial Sequence
<220> FEATURE:
<223> OTHER INFORMATION: Reverse primer for filled sequence for
      Yb8NBC18, a human genetic marker that is useful for genetic
      detection for forensic or bio-ancestry studies.

<400> SEQUENCE: 231
cctcccaaag tgctgctg                                                  18

<210> SEQ ID NO 232
<211> LENGTH: 21
<212> TYPE: DNA
<213> ORGANISM: Artificial Sequence
<220> FEATURE:
<223> OTHER INFORMATION: Labeled forward primer for Yb8NBC67, a human
      genetic marker that is useful for genetic detection for forensic
      or bio-ancestry studies.  The "n" is to be replaced with an
      adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 232
ngagcgagat gaacaaagga a                                              21

<210> SEQ ID NO 233
<211> LENGTH: 21
<212> TYPE: DNA
<213> ORGANISM: Artificial Sequence
<220> FEATURE:
<223> OTHER INFORMATION: Forward primer for Yb8NBC67, a human genetic
      marker that is useful for genetic detection for forensic or bio-
      ancestry studies.

<400> SEQUENCE: 233
agagcgagat gaacaaagga a                                              21

```
<210> SEQ ID NO 234
<211> LENGTH: 23
<212> TYPE: DNA
<213> ORGANISM: Artificial Sequence
<220> FEATURE:
<223> OTHER INFORMATION: Reverse primer for empty sequence for Yb8NBC67,
      a human genetic marker that is useful for genetic detection for
      forensic or bio-ancestry studies.

<400> SEQUENCE: 234
tgttcatagc agcctattct agc                                              23

<210> SEQ ID NO 235
<211> LENGTH: 21
<212> TYPE: DNA
<213> ORGANISM: Artificial Sequence
<220> FEATURE:
<223> OTHER INFORMATION: Reverse primer for filled sequence for
      Yb8NBC67, a human genetic marker that is useful for genetic
      detection for forensic or bio-ancestry studies.

<400> SEQUENCE: 235
cgggttcacg ccattctaag c                                                21

<210> SEQ ID NO 236
<211> LENGTH: 24
<212> TYPE: DNA
<213> ORGANISM: Artificial Sequence
<220> FEATURE:
<223> OTHER INFORMATION: Labeled forward primer for Yb8NBC237, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 236
ngctgaggat agagctatag caga                                             24

<210> SEQ ID NO 237
<211> LENGTH: 24
<212> TYPE: DNA
<213> ORGANISM: Artificial Sequence
<220> FEATURE:
<223> OTHER INFORMATION: Forward primer for Yb8NBC237, a human genetic
      marker that is useful for genetic detection for forensic or bio-
      ancestry studies.

<400> SEQUENCE: 237
tgctgaggat agagctatag caga                                             24

<210> SEQ ID NO 238
<211> LENGTH: 23
<212> TYPE: DNA
<213> ORGANISM: Artificial Sequence
<220> FEATURE:
<223> OTHER INFORMATION: Reverse primer for empty sequence for
      Yb8NBC237, a human genetic marker that is useful for genetic
      detection for forensic or bio-ancestry studies.

<400> SEQUENCE: 238
caaagcatgt caactgttac gta                                              23

<210> SEQ ID NO 239
<211> LENGTH: 17
<212> TYPE: DNA
<213> ORGANISM: Artificial Sequence
```

<220> FEATURE:
<223> OTHER INFORMATION: Reverse primer for filled sequence for
      Yb8NBC237, a human genetic marker that is useful for genetic
      detection for forensic or bio-ancestry studies.

<400> SEQUENCE: 239
cccggccgtt acggttt                                                  17

<210> SEQ ID NO 240
<211> LENGTH: 21
<212> TYPE: DNA
<213> ORGANISM: Artificial Sequence
<220> FEATURE:
<223> OTHER INFORMATION: Labeled forward primer for Yc1NBC60, a human
      genetic marker that is useful for genetic detection for forensic
      or bio-ancestry studies. The "n" is to be replaced with an
      adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 240
ngcaaacaag gaaggagaga a                                             21

<210> SEQ ID NO 241
<211> LENGTH: 21
<212> TYPE: DNA
<213> ORGANISM: Artificial Sequence
<220> FEATURE:
<223> OTHER INFORMATION: Forward primer for Yc1NBC60, a human genetic
      marker that is useful for genetic detection for forensic or bio-
      ancestry studies.

<400> SEQUENCE: 241
agcaaacaag gaaggagaga a                                             21

<210> SEQ ID NO 242
<211> LENGTH: 24
<212> TYPE: DNA
<213> ORGANISM: Artificial Sequence
<220> FEATURE:
<223> OTHER INFORMATION: Reverse primer for empty sequence for Yc1NBC60,
      a human genetic marker that is useful for genetic detection for
      forensic or bio-ancestry studies.

<400> SEQUENCE: 242
aggttaaacc atcttctttc taca                                          24

<210> SEQ ID NO 243
<211> LENGTH: 19
<212> TYPE: DNA
<213> ORGANISM: Artificial Sequence
<220> FEATURE:
<223> OTHER INFORMATION: Reverse primer for filled sequence for
      Yc1NBC60, a human genetic marker that is useful for genetic
      detection for forensic or bio-ancestry studies.

<400> SEQUENCE: 243
cccggcctct ttcttacaa                                                19

<210> SEQ ID NO 244
<211> LENGTH: 17
<212> TYPE: DNA
<213> ORGANISM: Artificial Sequence

```
<220> FEATURE:
<223> OTHER INFORMATION: Labeled forward primer for Ya5NBC157, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 244
ncactaccaa ccctctg                                                          17

<210> SEQ ID NO 245
<211> LENGTH: 17
<212> TYPE: DNA
<213> ORGANISM: Artificial Sequence
<220> FEATURE:
<223> OTHER INFORMATION: Forward primer for Ya5NBC157, a human genetic
      marker that is useful for genetic detection for forensic or bio-
      ancestry studies.

<400> SEQUENCE: 245
tcactaccaa ccctctg                                                          17

<210> SEQ ID NO 246
<211> LENGTH: 16
<212> TYPE: DNA
<213> ORGANISM: Artificial Sequence
<220> FEATURE:
<223> OTHER INFORMATION: Reverse primer for empty sequence for
      Ya5NBC157, a human genetic marker that is useful for genetic
      detection for forensic or bio-ancestry studies.

<400> SEQUENCE: 246
tggagttggg tttgct                                                           16

<210> SEQ ID NO 247
<211> LENGTH: 16
<212> TYPE: DNA
<213> ORGANISM: Artificial Sequence
<220> FEATURE:
<223> OTHER INFORMATION: Reverse primer for filled sequence for
      Ya5NBC157, a human genetic marker that is useful for genetic
      detection for forensic or bio-ancestry studies.

<400> SEQUENCE: 247
cggcctgggt ttgctt                                                           16

<210> SEQ ID NO 248
<211> LENGTH: 27
<212> TYPE: DNA
<213> ORGANISM: Artificial Sequence
<220> FEATURE:
<223> OTHER INFORMATION: Labeled forward primer for Yb7AD155, a human
      genetic marker that is useful for genetic detection for forensic
      or bio-ancestry studies.  The "n" is to be replaced with a
      cytosine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 248
nagcattaca tacaatagtt aggagca                                               27
```

-continued

<210> SEQ ID NO 249
<211> LENGTH: 27
<212> TYPE: DNA
<213> ORGANISM: Artificial Sequence
<220> FEATURE:
<223> OTHER INFORMATION: Forward primer for HS4.75, a human genetic
      marker that is useful for genetic detection for forensic or bio-
      ancestry studies.

<400> SEQUENCE: 249
cagcattaca tacaatagtt aggagca                                      27

<210> SEQ ID NO 250
<211> LENGTH: 22
<212> TYPE: DNA
<213> ORGANISM: Artificial Sequence
<220> FEATURE:
<223> OTHER INFORMATION: Reverse primer for empty sequence for HS4.75, a
      human genetic marker that is useful for genetic detection for
      forensic or bio-ancestry studies.

<400> SEQUENCE: 250
atgataagat ctcattcttt tt                                           22

<210> SEQ ID NO 251
<211> LENGTH: 20
<212> TYPE: DNA
<213> ORGANISM: Artificial Sequence
<220> FEATURE:
<223> OTHER INFORMATION: Reverse primer for filled sequence for HS4.75,
      a human genetic marker that is useful for genetic detection for
      forensic or bio-ancestry studies.

<400> SEQUENCE: 251
ccggccgatc tcattctttt                                              20

<210> SEQ ID NO 252
<211> LENGTH: 21
<212> TYPE: DNA
<213> ORGANISM: Artificial Sequence
<220> FEATURE:
<223> OTHER INFORMATION: Labeled forward primer for pAlu1-90961213, a
      human genetic marker that is useful for genetic detection for
      forensic or bio-ancestry studies.  The "n" is to be replaced with
      a thymine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 252
ncctaacaag ggactttgca g                                            21

<210> SEQ ID NO 253
<211> LENGTH: 21
<212> TYPE: DNA
<213> ORGANISM: Artificial Sequence
<220> FEATURE:
<223> OTHER INFORMATION: Forward primer for pAlu1-90961213, a human
      genetic marker that is useful for genetic detection for forensic
      or bio-ancestry studies.

<400> SEQUENCE: 253
tcctaacaag ggactttgca g                                            21

<210> SEQ ID NO 254
<211> LENGTH: 23
<212> TYPE: DNA
<213> ORGANISM: Artificial Sequence
<220> FEATURE:
<223> OTHER INFORMATION: Reverse primer for empty sequence for pAlu1-
     90961213, a human genetic marker that is useful for genetic
     detection for forensic or bio-ancestry studies.

<400> SEQUENCE: 254
agatgggaaa gattctccac ttt                                              23

<210> SEQ ID NO 255
<211> LENGTH: 18
<212> TYPE: DNA
<213> ORGANISM: Artificial Sequence
<220> FEATURE:
<223> OTHER INFORMATION: Reverse primer for filled sequence for pAlu1-
     90961213, a human genetic marker that is useful for genetic
     detection for forensic or bio-ancestry studies.

<400> SEQUENCE: 255
cggcctccca aagaagat                                                    18

<210> SEQ ID NO 256
<211> LENGTH: 19
<212> TYPE: DNA
<213> ORGANISM: Artificial Sequence
<220> FEATURE:
<223> OTHER INFORMATION: Labeled forward primer for Ya5ACA912, a human
     genetic marker that is useful for genetic detection for forensic
     or bio-ancestry studies.  The "n" is to be replaced with an
     adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 256
ncagaggcca ccctgtagg                                                   19

<210> SEQ ID NO 257
<211> LENGTH: 19
<212> TYPE: DNA
<213> ORGANISM: Artificial Sequence
<220> FEATURE:
<223> OTHER INFORMATION: Forward primer for Ya5ACA912, a human genetic
     marker that is useful for genetic detection for forensic or bio-
     ancestry studies.

<400> SEQUENCE: 257
acagaggcca ccctgtagg                                                   19

<210> SEQ ID NO 258
<211> LENGTH: 22
<212> TYPE: DNA
<213> ORGANISM: Artificial Sequence
<220> FEATURE:
<223> OTHER INFORMATION: Reverse primer for empty sequence for
     Ya5ACA912, a human genetic marker that is useful for genetic
     detection for forensic or bio-ancestry studies.

<400> SEQUENCE: 258
tgagactggg tgactgtgtt tt                                               22

<210> SEQ ID NO 259
<211> LENGTH: 18
<212> TYPE: DNA
<213> ORGANISM: Artificial Sequence
<220> FEATURE:
<223> OTHER INFORMATION: Reverse primer for filled sequence for
     Ya5ACA912, a human genetic marker that is useful for genetic
     detection for forensic or bio-ancestry studies.

<400> SEQUENCE: 259
acctggcctg ggtgactg                                                        18

<210> SEQ ID NO 260
<211> LENGTH: 22
<212> TYPE: DNA
<213> ORGANISM: Artificial Sequence
<220> FEATURE:
<223> OTHER INFORMATION: Labeled forward primer for Yc1RG148, a human
      genetic marker that is useful for genetic detection for forensic
      or bio-ancestry studies. The "n" is to be replaced with a
      cytosine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 260
nacgttctga aacatccatc tc                                                   22

<210> SEQ ID NO 261
<211> LENGTH: 22
<212> TYPE: DNA
<213> ORGANISM: Artificial Sequence
<220> FEATURE:
<223> OTHER INFORMATION: Forward primer for Yc1RG148, a human genetic
      marker that is useful for genetic detection for forensic or bio-
      ancestry studies.

<400> SEQUENCE: 261
cacgttctga aacatccatc tc                                                   22

<210> SEQ ID NO 262
<211> LENGTH: 26
<212> TYPE: DNA
<213> ORGANISM: Artificial Sequence
<220> FEATURE:
<223> OTHER INFORMATION: Reverse primer for empty sequence for Yc1RG148,
      a human genetic marker that is useful for genetic detection for
      forensic or bio-ancestry studies.

<400> SEQUENCE: 262
tccagtttca tatttatttt tgcttg                                               26

<210> SEQ ID NO 263
<211> LENGTH: 20
<212> TYPE: DNA
<213> ORGANISM: Artificial Sequence
<220> FEATURE:
<223> OTHER INFORMATION: Reverse primer for filled sequence for
      Yc1RG148, a human genetic marker that is useful for genetic
      detection for forensic or bio-ancestry studies.

<400> SEQUENCE: 263
cggcctgctt gtttgtttta                                                      20

<210> SEQ ID NO 264
<211> LENGTH: 21
<212> TYPE: DNA
<213> ORGANISM: Artificial Sequence
<220> FEATURE:
<223> OTHER INFORMATION: Labeled forward primer for Ya5-NBC171, a human
      genetic marker that is useful for genetic detection for forensic
      or bio-ancestry studies. The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

```
<400> SEQUENCE: 264
nccctgctaa cataacatcc a                                              21

<210> SEQ ID NO 265
<211> LENGTH: 21
<212> TYPE: DNA
<213> ORGANISM: Artificial Sequence
<220> FEATURE:
<223> OTHER INFORMATION: Forward primer for Ya5-NBC171, a human genetic
      marker that is useful for genetic detection for forensic or bio-
      ancestry studies.

<400> SEQUENCE: 265
tccctgctaa cataacatcc a                                              21

<210> SEQ ID NO 266
<211> LENGTH: 20
<212> TYPE: DNA
<213> ORGANISM: Artificial Sequence
<220> FEATURE:
<223> OTHER INFORMATION: Reverse primer for empty sequence for Ya5-
      NBC171, a human genetic marker that is useful for genetic
      detection for forensic or bio-ancestry studies.

<400> SEQUENCE: 266
cgcacccagc tcaaaatgta                                                20

<210> SEQ ID NO 267
<211> LENGTH: 19
<212> TYPE: DNA
<213> ORGANISM: Artificial Sequence
<220> FEATURE:
<223> OTHER INFORMATION: Reverse primer for filled sequence for Ya5-
      NBC171, a human genetic marker that is useful for genetic
      detection for forensic or bio-ancestry studies.

<400> SEQUENCE: 267
acccggcctc aaaatgtat                                                 19

<210> SEQ ID NO 268
<211> LENGTH: 17
<212> TYPE: DNA
<213> ORGANISM: Artificial Sequence
<220> FEATURE:
<223> OTHER INFORMATION: Labeled forward primer for Ya5NBC212, a human
      genetic marker that is useful for genetic detection for forensic
      or bio-ancestry studies.  The "n" is to be replaced with a
      cytosine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 268
natttggcgc aagtggt                                                   17

<210> SEQ ID NO 269
<211> LENGTH: 17
<212> TYPE: DNA
<213> ORGANISM: Artificial Sequence
<220> FEATURE:
<223> OTHER INFORMATION: Forward primer for Ya5NBC212, a human genetic
      marker that is useful for genetic detection for forensic or bio-
      ancestry studies.

<400> SEQUENCE: 269
catttggcgc aagtggt                                                   17
```

```
<210> SEQ ID NO 270
<211> LENGTH: 23
<212> TYPE: DNA
<213> ORGANISM: Artificial Sequence
<220> FEATURE:
<223> OTHER INFORMATION: Reverse primer for empty sequence for
      Ya5NBC212, a human genetic marker that is useful for genetic
      detection for forensic or bio-ancestry studies.

<400> SEQUENCE: 270
catgtattgc atgttgcttt tgt                                             23

<210> SEQ ID NO 271
<211> LENGTH: 15
<212> TYPE: DNA
<213> ORGANISM: Artificial Sequence
<220> FEATURE:
<223> OTHER INFORMATION: Reverse primer for filled sequence for
      Ya5NBC212, a human genetic marker that is useful for genetic
      detection for forensic or bio-ancestry studies.

<400> SEQUENCE: 271
cgcccggcct gtatt                                                      15

<210> SEQ ID NO 272
<211> LENGTH: 24
<212> TYPE: DNA
<213> ORGANISM: Artificial Sequence
<220> FEATURE:
<223> OTHER INFORMATION: Labeled forward primer for Ya5NBC54, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 272
ncattgtatc atctgctgta cctg                                            24

<210> SEQ ID NO 273
<211> LENGTH: 24
<212> TYPE: DNA
<213> ORGANISM: Artificial Sequence
<220> FEATURE:
<223> OTHER INFORMATION: Forward primer for Ya5NBC54, a human genetic
      marker that is useful for genetic detection for forensic or bio-
      ancestry studies.

<400> SEQUENCE: 273
tcattgtatc atctgctgta cctg                                            24

<210> SEQ ID NO 274
<211> LENGTH: 21
<212> TYPE: DNA
<213> ORGANISM: Artificial Sequence
<220> FEATURE:
<223> OTHER INFORMATION: Reverse primer for empty sequence for Ya5NBC54,
      a human genetic marker that is useful for genetic detection for
      forensic or bio-ancestry studies.

<400> SEQUENCE: 274
tttttgcttt agatttttgt t                                               21

<210> SEQ ID NO 275
<211> LENGTH: 16
<212> TYPE: DNA
<213> ORGANISM: Artificial Sequence
```

```
<220> FEATURE:
<223> OTHER INFORMATION: Reverse primer for filled sequence for
      Ya5NBC54, a human genetic marker that is useful for genetic
      detection for forensic or bio-ancestry studies.

<400> SEQUENCE: 275
cgcgcccggc ctagat                                                     16

<210> SEQ ID NO 276
<211> LENGTH: 22
<212> TYPE: DNA
<213> ORGANISM: Artificial Sequence
<220> FEATURE:
<223> OTHER INFORMATION: Labeled forward primer for Ya5NBC335, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 276 nggggtacttt ggccttagag aa                                             22

<210> SEQ ID NO 277
<211> LENGTH: 22
<212> TYPE: DNA
<213> ORGANISM: Artificial Sequence
<220> FEATURE:
<223> OTHER INFORMATION: Forward primer for Ya5NBC335, a human genetic
      marker that is useful for genetic detection for forensic or bio-
      ancestry studies.

<400> SEQUENCE: 277
tgggtacttt ggccttagag aa                                              22

<210> SEQ ID NO 278
<211> LENGTH: 23
<212> TYPE: DNA
<213> ORGANISM: Artificial Sequence
<220> FEATURE:
<223> OTHER INFORMATION: Reverse primer for empty sequence for
      Ya5NBC335, a human genetic marker that is useful for genetic
      detection for forensic or bio-ancestry studies.

<400> SEQUENCE: 278
tgtgaatgac atttttatcc tgt                                             23

<210> SEQ ID NO 279
<211> LENGTH: 20
<212> TYPE: DNA
<213> ORGANISM: Artificial Sequence
<220> FEATURE:
<223> OTHER INFORMATION: Reverse primer for filled sequence for
      Ya5NBC335, a human genetic marker that is useful for genetic
      detection for forensic or bio-ancestry studies.

<400> SEQUENCE: 279
tttagccggg atggtatcct                                                 20

<210> SEQ ID NO 280
<211> LENGTH: 25
<212> TYPE: DNA
<213> ORGANISM: Artificial Sequence
```

```
<220> FEATURE:
<223> OTHER INFORMATION: Labeled forward primer for Ya5-MLS37, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 280
nttgcccagg tatttgttat acatt                                             25

<210> SEQ ID NO 281
<211> LENGTH: 25
<212> TYPE: DNA
<213> ORGANISM: Artificial Sequence
<220> FEATURE:
<223> OTHER INFORMATION: Forward primer for Ya5-MLS37, a human genetic
      marker that is useful for genetic detection for forensic or bio-
      ancestry studies.

<400> SEQUENCE: 281
tttgcccagg tatttgttat acatt                                             25

<210> SEQ ID NO 282
<211> LENGTH: 27
<212> TYPE: DNA
<213> ORGANISM: Artificial Sequence
<220> FEATURE:
<223> OTHER INFORMATION: Reverse primer for empty sequence for Ya5-
      MLS37, a human genetic marker that is useful for genetic detection
      for forensic or bio-ancestry studies.

<400> SEQUENCE: 282
ttcagttaat tgggtatttt taaacca                                           27

<210> SEQ ID NO 283
<211> LENGTH: 20
<212> TYPE: DNA
<213> ORGANISM: Artificial Sequence
<220> FEATURE:
<223> OTHER INFORMATION: Reverse primer for filled sequence for Ya5-
      MLS37, a human genetic marker that is useful for genetic detection
      for forensic or bio-ancestry studies.

<400> SEQUENCE: 283
ccggccttaa ttgggtattt                                                   20

<210> SEQ ID NO 284
<211> LENGTH: 24
<212> TYPE: DNA
<213> ORGANISM: Artificial Sequence
<220> FEATURE:
<223> OTHER INFORMATION: Labeled forward primer for Ya5ACA1549, a human
      genetic marker that is useful for genetic detection for forensic
      or bio-ancestry studies.  The "n" is to be replaced with an
      adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 284
nctccacaaa taggttctac ttca                                              24
```

```
<210> SEQ ID NO 285
<211> LENGTH: 24
<212> TYPE: DNA
<213> ORGANISM: Artificial Sequence
<220> FEATURE:
<223> OTHER INFORMATION: Forward primer for Ya5ACA1549, a human genetic
      marker that is useful for genetic detection for forensic or bio-
      ancestry studies.

<400> SEQUENCE: 285
actccacaaa taggttctac ttca                                          24

<210> SEQ ID NO 286
<211> LENGTH: 25
<212> TYPE: DNA
<213> ORGANISM: Artificial Sequence
<220> FEATURE:
<223> OTHER INFORMATION: Reverse primer for empty sequence for
      Ya5ACA1549, a human genetic marker that is useful for genetic
      detection for forensic or bio-ancestry studies.

<400> SEQUENCE: 286
tttggtattt tttcttttca tttac                                         25

<210> SEQ ID NO 287
<211> LENGTH: 17
<212> TYPE: DNA
<213> ORGANISM: Artificial Sequence
<220> FEATURE:
<223> OTHER INFORMATION: Reverse primer for filled sequence for
      Ya5ACA1549, a human genetic marker that is useful for genetic
      detection for forensic or bio-ancestry studies.

<400> SEQUENCE: 287
cccggccttt tcttttc                                                  17

<210> SEQ ID NO 288
<211> LENGTH: 20
<212> TYPE: DNA
<213> ORGANISM: Artificial Sequence
<220> FEATURE:
<223> OTHER INFORMATION: Labeled forward primer for Ya5-MLS04, a human
      genetic marker that is useful for genetic detection for forensic
      or bio-ancestry studies.  The "n" is to be replaced with an
      adenine tagged with a label.
<220> FEATURE:
<221> NAME/KEY: misc_feature
<222> LOCATION: (1)..(1)
<223> OTHER INFORMATION: n is a, c, g, or t

<400> SEQUENCE: 288
nggaatccct ttcccaaaaa                                               20

<210> SEQ ID NO 289
<211> LENGTH: 20
<212> TYPE: DNA
<213> ORGANISM: Artificial Sequence
<220> FEATURE:
<223> OTHER INFORMATION: Forward primer for Ya5-MLS04, a human genetic
      marker that is useful for genetic detection for forensic or bio-
      ancestry studies.

<400> SEQUENCE: 289
aggaatccct ttcccaaaaa                                               20

<210> SEQ ID NO 290
<211> LENGTH: 24
<212> TYPE: DNA
<213> ORGANISM: Artificial Sequence
```

```
<220> FEATURE:
<223> OTHER INFORMATION: Reverse primer for empty sequence for Ya5-
      MLS04, a human genetic marker that is useful for genetic detection
      for forensic or bio-ancestry studies.

<400> SEQUENCE: 290
ttttgtgata atagacttta cttt                                          24

<210> SEQ ID NO 291
<211> LENGTH: 18
<212> TYPE: DNA
<213> ORGANISM: Artificial Sequence
<220> FEATURE:
<223> OTHER INFORMATION: Reverse primer for filled sequence for Ya5-
      MLS04, a human genetic marker that is useful for genetic detection
      for forensic or bio-ancestry studies.

<400> SEQUENCE: 291
cccggccaat agacttta                                                 18

<210> SEQ ID NO 292
<211> LENGTH: 20
<212> TYPE: DNA
<213> ORGANISM: Artificial Sequence
<220> FEATURE:
<223> OTHER INFORMATION: Labeled forward primer for Yb8NBC225, a human
      genetic marker that is useful for genetic detection for forensic
      or bio-ancestry studies.  The "n" is to be replaced with a thymine
      tagged with a label.
<220> FEATURE:
<221> NAME/KEY: misc_feature
<222> LOCATION: (1)..(1)
<223> OTHER INFORMATION: n is a, c, g, or t

<400> SEQUENCE: 292
ngagtccagc ccattttagc                                               20

<210> SEQ ID NO 293
<211> LENGTH: 20
<212> TYPE: DNA
<213> ORGANISM: Artificial Sequence
<220> FEATURE:
<223> OTHER INFORMATION: Forward primer for Yb8NBC225, a human genetic
      marker that is useful for genetic detection for forensic or bio-
      ancestry studies.

<400> SEQUENCE: 293
tgagtccagc ccattttagc                                               20

<210> SEQ ID NO 294
<211> LENGTH: 23
<212> TYPE: DNA
<213> ORGANISM: Artificial Sequence
<220> FEATURE:
<223> OTHER INFORMATION: Reverse primer for empty sequence for
      Yb8NBC225, a human genetic marker that is useful for genetic
      detection for forensic or bio-ancestry studies.

<400> SEQUENCE: 294
aattagtgtg aagcatataa aaa                                           23

<210> SEQ ID NO 295
<211> LENGTH: 20
<212> TYPE: DNA
<213> ORGANISM: Artificial Sequence
<220> FEATURE:
<223> OTHER INFORMATION: Reverse primer for filled sequence for
      Yb8NBC225, a human genetic marker that is useful for genetic
      detection for forensic or bio-ancestry studies.
```

```
<400> SEQUENCE: 295
tgcacccggc ataaaaatac                                              20

<210> SEQ ID NO 296
<211> LENGTH: 749
<212> TYPE: DNA
<213> ORGANISM: Artificial Sequence
<220> FEATURE:
<223> OTHER INFORMATION: Reverse primer for empty sequence for Ya5-
      MLS48, a human genetic marker that is useful for genetic detection
      for forensic or bio-ancestry studies.

<400> SEQUENCE: 296
actacaatcg gtataatctt ctaatttgtc tcattataaa gtattctatt tctataggac    60
aggttaataa tccagaaaaa tgaaactaag atgatcaaaa cctgtagtta atactttaaa   120
atacaatcca acaccattta atcttctgag ttggtgacac tccaatttct tctctctaac   180
gtttccttaa gagttgtaat tggggccggg cgcggtggct cacgcctgta atcccagcac   240
tttgggaggc cgaggcgggc ggatcatgag gtcaggagat cgagaccatc ccggctaaaa   300
cggtgaaacc ccgtctctac taaaaataca aaaaattagc cgggcgtagt ggcgggcgcc   360
tgtagtccca gctacttggg aggctgaggc aggagaatgg cgtgaacccg ggaggcggag   420
cttacagtga gccgagatcc cgccactgca ctccagcctg ggcgacagag cgagactccg   480
tctcaaaaaa aaaaaaaaaa aaaaaaaaaa aagagttgta atcaaaggat gcctgggtaa   540
gagctgggtt tggttttggt acttaggtct tttggtaatt ccattttagc accactgaat   600
tatcattagt gctttaaaga gctgccttttt gtggatagaa tgaattatta tacatattca   660 tcattttgt cttcctactg atacatttaa ggagtggaga tacaatattt tcatccaata   720
ggtcacaatg catataattg ctgacattt                                    749

<210> SEQ ID NO 297
<211> LENGTH: 427
<212> TYPE: DNA
<213> ORGANISM: Artificial Sequence
<220> FEATURE:
<223> OTHER INFORMATION: Reverse primer for empty sequence for Ya5-
      MLS48, a human genetic marker that is useful for genetic detection
      for forensic or bio-ancestry studies.

<400> SEQUENCE: 297
caaactatcg gtataatctt ctaatttgtc tcattataaa gtattctatt tctataggac    60
aggttaataa tccagaaaaa tgaaactaag atgatcaaaa cctgtagtta atactttaaa   120
atacaatcca acaccattta atcttctgag ttggtgacac tccaatttct tctctctaac   180
gtttccttaa gagttgtaat caaaggatgc ctgggtaaga gctgggtttg gttttggtac   240
ttaggtcttt tggtaattcc attttagcac cactgaatta tcattagtgc tttaaagagc   300
tgccttttgt ggatagaatg aattattata catattcatc attttgtct tcctactgat   360 acatttaagg agtggagata caatattttc atccaatagg tcacaatgca tataattgct   420
gacattt                                                            427

<210> SEQ ID NO 298
<211> LENGTH: 21
<212> TYPE: DNA
<213> ORGANISM: Artificial Sequence
<220> FEATURE:
<223> OTHER INFORMATION: Forward primer for CH1-2250, a human genetic
      marker that is useful for genetic detection for forensic or bio-
      ancestry studies.
```

-continued

```
<400> SEQUENCE: 298
tggacctgtg cagttcaaac c                                              21
```

METHOD FOR GENETIC DETECTION USING INTERSPERSED GENETIC ELEMENTS: A MULTIPLEXED DNA ANALYSIS SYSTEM

CLAIM OF PRIORITY

This application makes reference to, incorporates the same herein, and claims all benefits accruing under 35 U.S.C. § 119 from an application for METHOD FOR GENETIC DETECTION USING INTERSPERSED GENETIC ELEMENTS: A MULTIPLEXED DNA ANALYSIS SYSTEM, earlier filed in the United States Patent and Trademark Office on 24 Oct. 2014 and there duly assigned Ser. No. 62/068,337. The present application also makes reference to, incorporates the same herein, claims all benefits accruing under 35 U.S.C. § 120 from, and is a Continuation-in-Part of a U.S. Patent Application having duly assigned Ser. No. 14/054,680, now U.S. Pat. No. 10,004,561, which was filed in the United States Patent and Trademark Office on 15 Oct. 2013, bears the aforementioned name, and claims priority to a U.S. Provisional Patent Application having duly assigned Ser. No. 61/714,088, which was filed in the United States Patent and Trademark Office on 15 Oct. 2012, bears the aforementioned name, is hereby incorporated by reference, and for which all benefits accruing under 35 U.S.C. § 119 are claimed.

SEQUENCE LISTING

Sequences are being submitted concurrently with this substitute specification via EFS-Web as an ASCII text file named P59855-CIP-Seqlist_ST25.txt, created on 5 Jan. 2016, the file having a size of 110,000 bytes. All sequences in the latter ASCII text file are disclosed in the specification filed on 26 Oct. 2015. No new matter is added.

BACKGROUND OF THE INVENTION

Field of the Invention

The present invention relates generally to human identification and bio-ancestry testing, and, more particularly, to improvements that enhance the sensitivity of detection during analysis of human DNA samples for human identity testing or for bio-ancestry studies.

Description of Related Art

Short tandem repeat (STR) loci are the primary genetic markers used in human identity testing. These markers are highly polymorphic and afford a high degree of sensitivity of detection such that relatively low quantities (1 ng-250 pg) of template DNA can be analyzed (Andersen, J. F., et al., *Further validation of a multiplex STR system for use in routine forensic identity testing*, Forensic Science International, 78(1): 47-64 (1996); Brinkmann, B., et al., *Mutation rate in human microsatellites: influence of the structure and length of the tandem repeat*, The American Journal of Human Genetics, 62(6): 1408-1415 (1998); Collins, P. J., et al., *Developmental validation of a single-tube Amplification of the 13 CODIS STR Loci, D2S1338, D19S433, and amelogenin: The AmpFSTR® Identifiler® PCR Amplification Kit*, Journal of Forensic Sciences, 49(6): 1265-1277 (2004); LaFountain, M. J., et al., *TWGDAM Validation of the AmpFeSTR Profiler Plus and AmpFeSTR COfiler STR Multiplex Systems Using Capillary Electrophoresis*, Journal of Forensic Sciences, 46(5): 1191-1198 (2001); Micka, K. A., et al., *Validation of multiplex polymorphic STR amplification sets developed for personal identification applications*, Journal of Forensic Sciences, 41: 582-590 (1996); Moretti, T., et al., *Validation of short tandem repeats (STRs) for forensic usage: performance testing of fluorescent multiplex STR systems and analysis of authentic and simulated forensic samples*, Journal of Forensic Sciences, 46(3): 647 (2001)).

Retrotransposable elements (REs), including long interspersed nuclear elements (LINEs), short interspersed nuclear elements (SINEs) and SVA elements, are another group of markers that can be useful for human identity testing. SINEs are a class of REs that are typically less than 500 nucleotides long; while LINEs are typically greater than 500 nucleotides long (A. F. A. Smit, *The origin of interspersed repeats in the human genome*, Current Opinion in Genetics Development, 6(6): 743-748 (1996); Batzer, M. A., et al., *Alu repeats and human genomic diversity*, Nature Reviews Genetics, 3(5): 370-379 (2002); Batzer, M. A., et al., *African origin of human-specific polymorphic Alu insertions*, Proceedings of the National Academy of Sciences, 91(25): 12288 (1994); Feng, Q., et al., *Human L1 retrotransposon encodes a conserved endonuclease required for retrotransposition*, Cell, 87(5): 905-916 (1996); Houck, C. M., et al., *A ubiquitous family of repeated DNA sequences in the human genome*, Journal of Molecular Biology, 132(3): 289-306 (1979); Kazazian, H. H., et al., *The impact of L1 retrotransposons on the human genome*, Nature Genetics, 19(1): 19-24 (1998); Ostertag, E. M., et al., *Biology of mammalian L1 retrotransposons*, Annual Review of Genetics, 35(1): 501-538 (2001)). LINE full-length elements are ~6 kb in length, contain an internal promoter for polymerase II and two open reading frames (ORFs) and end in a polyA-tail. SINEs include Alu elements, primate specific SINEs that have reached a copy number in excess of one million in the human genome. SINEs were originally defined by their interspersed nature and length (75-500 bp), but have been further characterized by their RNA polymerase III transcription. The third type of RE is the composite retrotransposon known as an SVA (SINE/VNTR/Alu) element (Wang, H., et al., *SVA Elements: A Hominid-specific Retroposon Family*, J. Mol. Biol. 354: 994-1007 (2005)). SVAs are composite elements named after their main components, SINE, a variable number of tandem repeats (VNTR), and Alu. As a consequence of the VNTR region, full-length SVA elements can vary greatly in size. These markers have potential application to identity testing, kinship analyses, and evolutionary studies (see Smit; Batzer, et al. (2002); Batzer, et al. (1994); Feng, et al.; Houck, et al.; Kazazian et al.; and Ostertag, et al., references, cited supra). Insertion and null allele (INNUL) markers may include SINEs, LINEs and SVAs.

The structure of REs is described in FIG. 1. The Alu family of interspersed repeats is the most successful of the mobile genetic elements within primate genomes, having amplified to a copy number of greater than 500,000 per haploid genome. Alu elements mobilize via an RNA polymerase III-derived intermediate in a process defined as retroposition. Alu repeats are approximately 300 bp in length and are ancestrally derived from the 7SL RNA gene. Each Alu element is dimeric in structure and is flanked by short intact direct repeats. These direct repeat sequences are formed when an Alu element inserts within staggered nicks in the genome. In addition, each Alu element has an oligo dA-rich region in the middle and at the 3' end (FIG. 1). The amplification of Alu repeats to such large copy numbers has occurred over a period of 65 million years and the process is still active in the present day genome (A. F. A. Smit, *The origin of interspersed repeats in the human genome*, Current Opinion in Genetics Development, 6(6): 743-748 (1996);

Zangenberg, et al., cited supra; Budowle, B., *SNP typing strategies*, Forensic Science International, 146: S139 (2004)).

Alu sequences within the human genome can be divided into subfamilies of related members based upon the presence of diagnostic mutations shared in common by subfamily members. These subfamilies are of different evolutionary ages with the younger ones (Ya5, Ya8 and Yb8) being primarily restricted to the human genome (Houck, C. M., et al., *A ubiquitous family of repeated DNA sequences in the human genome*, Journal of Molecular Biology, 132(3): 289-306 (1979); Kazazian, H. H., et al., *The impact of L1 retrotransposons on the human genome*, Nature Genetics, 19(1): 19-24 (1998)). These subfamilies arose in a hierarchical manner over evolutionary time with the younger subfamily members retaining the diagnostic mutations of the older subfamily that preceded it.

The Ya5/8 and the Yb8 subfamilies are independent derivatives of the Y subfamily of Alu repeats. The young subfamilies are present in relatively small copy numbers within the genome compared to the bulk of the Alt repeats, which primarily belong to the PS and AS subfamilies. For instance, the copy number of the Y subfamily has been given as >200,000; Ya5 subfamily, 2640 members; Ya8 subfamily, 70 members and the Yb8 subfamily, approximately 1852 members (A. M. Roy-Engel, et al., *Alu insertion polymorphisms for the study of human genomic diversity*. Genetics 159: 279-290 (September, 2001), Table 3 on page 289).

The youngest subfamilies of Alu elements, Ya5, Ya8 and Yb8 first arose in the primate genomes approximately 5 million years ago (Batzer, M. A., et al., *African origin of human-specific polymorphic Alu insertions*, Proceedings of the National Academy of Sciences, 91(25): 12288 (1994); Feng, Q., et al., *Human L1 retrotransposon encodes a conserved endonuclease required for retrotransposition*, Cell, 87(5): 905-916 (1996)). Amplification of Alu elements within humans is still an ongoing process. As human population groups migrated and colonized different parts of the world, all new Alu insertions in individuals belonging to the newer populations were absent in the original population, and vice versa. In other words, several elements that belong to the young subfamilies are dimorphic for their presence/absence within different human population groups (Syvanen, A. C., et al., *Identification of individuals by analysis of biallelic DNA markers, using PCR and solid-phase minisequencing*, American Journal of Human Genetics, 52(1): 46-59 (1993); LaRue, B. L., et al., *A validation study of the Qiagen Investigator DIPplex® kit; an INDEL-based assay for human identification*, International Journal of Legal Medicine, 2012, 1-8).

Realizing the potential of these dimorphic Alu elements as genetic markers, investigators have identified the dimorphic Alu repeats from a larger background of fixed Alu elements. Using the Alu insertion PCR assay described in FIG. 2, each Alu element was tested against a panel of several human genomic DNA samples as templates for the levels of polymorphism. Each and every dimorphic Alu repeat has been thoroughly characterized for its respective allele frequency in as many as 50 different worldwide population groups (Syvanen, A. C., et al., *Identification of individuals by analysis of biallelic DNA markers, using PCR and solid-phase minisequencing*, American Journal of Human Genetics, 52(1): 46-59 (1993); LaRue, B. L., et al., referenced supra; Shriver, M. D., et al., *Ethnic-affiliation estimation by use of population-specific DNA markers*. American Journal of Human Genetics, 60(4): 957 (1997)).

Ustyugova, S. V., et al. (*Cell line fingerprinting using retroelement insertion polymorphism*. BioTechniques, 38(4): 561-565 (2005)), demonstrated that REs could be used for cell line identification. Novick, et al. (*Polymorphic human specific Alu insertions as markers for human identification*, Electrophoresis, 16(1): 1596-1601 (1995)), and Mamedov, et al. (*A new set of markers for human identification based on 32 polymorphic Alu insertions*, European Journal of Human Genetics, 18(7): 808-814 (2010)), recently described a set of Alu's (a type of SINE) for paternity testing. Both of these studies intimated that the systems could be applied to forensic analyses. The REs have low mutation rates which makes them appealing for kinship analyses compared with the less stable STRs. In addition, they do not yield stutter artifacts, due to slippage during the PCR, which can reduce some interpretation issues associated with STRs in forensic mixture profiles (Andersen, J. F., et al., *Further validation of a multiplex STR system for use in routine forensic identity testing*, Forensic Science International, 78(1): 47-64 (1996); Brinkmann, B., et al., *Mutation rate in human microsatellites: influence of the structure and length of the tandem repeat*, The American Journal of Human Genetics, 62(6): 1408-1415 (1998); Moretti, T., et al., *Validation of short tandem repeats (STRs) for forensic usage: performance testing of fluorescent multiplex STR systems and analysis of authentic and simulated forensic samples*, Journal of Forensic Sciences, 46(3): 647 (2001)).

Forensic samples often are compromised in quality and quantity. Degraded samples may contain fragments of DNA that are less than 250 bp in length, and the quantities may be limited to subnanogram levels of recoverable DNA (Burger, J., et al., *DNA preservation: A microsatellite DNA study on ancient skeletal remains*, Electrophoresis, 20(8): 1722-1728 (1999); Fondevila, M., et al., *Challenging DNA: assessment of a range of genotyping approaches for highly degraded forensic samples*, Forensic Science International: Genetics Supplement Series, 1(1): 26-28 (2008); Golenberg, E. M., et al., *Effect of Highly Fragmented DNA on PCR*, Nucleic Acids Research, 24(24): 5026-5033 (1996); R. Hughes-Stamm, S., et al., *Assessment of DNA degradation and the genotyping success of highly degraded samples*, International Journal of Legal Medicine, 125(3): 341-348 (2011)). REs can range in size from hundreds (SINEs) to several thousand (LINEs) bp in length (see Smit; Batzer, et al. (2002); Batzer, et al. (1994); Feng, et al.; Houck, et al.; Kazazian et al.; and Ostertag, et al., references, cited supra). Previous attempts to use Alu sequences for identity testing capitalized on the size difference between insertion and null alleles by amplifying the entire region with the same forward and reverse primers (Novick, G. E., et al., *Polymorphic human specific Alu insertions as markers for human identification*, Electrophoresis, 16(1): 1596-1601 (1995)). The insertion allele would be 200-400 bp larger than the null allele, and could be detected electrophoretically based on size differences. While useful for paternity testing and some population studies where DNA quality is not compromised, the large size difference between amplicons of the null and insertion alleles will impact amplification efficiency during the PCR and is a limitation for forensic samples. The limitation is differential amplification favoring the smaller amplicon (i.e., the null allele) and possibly dropping out of the insertion element, which is exacerbated if the sample is highly degraded.

The use of SINEs such as Alu repeats in determining human identity has been studied and reported (see Mamedov, et al., and Novick, et al., cited supra). Until now, however, due to the inherent size difference associated with INNULs, the use of REs has not been useful in a practical sense. Although REs make up over 40% of the human genome (Lander, E. S., et al., *Initial sequencing and analysis of the human genome*, Nature, 409(6822): 860-921 (2001)) and present myriad potential targets for human identity testing, these INNULS (i.e., insertion and null alleles, instead of INDELs because one of the allele forms is not the result of a deletion) have received limited attention for use in forensic human identity testing (Zangenberg, et al., *Multiplex PCR: Optimization Guidelines*, in PCR Applications: Protocols for Functional Genomics, Academic Press, San Diego, Calif., 1999, p. 73-94).

Advantageously, a convenient way to design synthetic primers for PCR amplification of relatively short, repeating sequences, known as the mini-primer design, has been previously described in U.S. Pat. No. 7,794,983 B2, to Sinha, et al., which is hereby incorporated by reference. Using the mini-primer design, interspersed genetic elements containing characteristic direct repeat sequences (direct repeats) may be amplified and quantitated.

The above information disclosed in this Background section is only for enhancement of understanding of the background of the invention, and, therefore, it may contain information that does not form the prior art that is already known to a person of ordinary skill in the art.

SUMMARY OF THE INVENTION

Accordingly, one object of the present invention is to provide, using the mini-primer design, synthetic primers for Interspersed Element Insertion polymorphisms that would facilitate the production of small PCR products having as few as 50 to 150 base pairs (bp) when human genomic DNA is amplified.

This short sequence PCR amplification process takes advantage of the fact that all retrotransposon insertions have a characteristic sequence at the beginning and the end of insertion referred as Target Site Duplication (TSD). Another object of the present invention is to design synthetic primers to include part or full TSD sequences to provide specific insertion or no-insertion alleles in multiplex systems.

Another object of the present invention is to design, optimize and validate a multiplex amplification system (single amplification for multiple targets) containing LINEs, SINEs and SVAs for forensic applications.

Another object of the present invention is to design, optimize and validate a multiplex amplification system (single amplification for multiple targets) containing LINEs, SINEs and SVAs for bio-ancestry applications.

Another object of the present invention is to use the power of discrimination and analytical performance of the short sequence PCR amplification process to select markers as being suitable for either forensic or bio-ancestry applications.

Another object of the present invention is to develop a practical method for using LINEs and SVAs as potential markers in a DNA amplification system for human identification.

Another object of the present invention is to develop a multiplex amplification system that makes use of retrotransposable element (RE) markers and is useful in forensic cases in which the DNA samples have been substantially degraded.

Another object of the present invention is to provide a kit for multiplexed DNA analysis, the kit comprising a DNA standard, the DNA standard comprising DNA at a known DNA concentration, the DNA standard being useful as a positive amplification control during a polymerase chain reaction (PCR) analysis; a Master Mix to support a PCR analysis, the Master Mix comprising a plurality of deoxynucleotides (dNTPs), magnesium chloride and a buffer; a DNA polymerase; a mixture of primers corresponding to a group of chromosomal INNUL markers selected for multiplexing, the mixture of primers including for each selected chromosomal marker a primer set including a forward primer, a reverse primer corresponding to a null allele and a reverse primer corresponding to a filled allele, at least one primer of each primer set including an observable label; and instructions for using the kit in conjunction with one or more instruments comprised by a PCR DNA analysis system, the PCR system providing an amplicon corresponding to each primer, the amplicons corresponding to each primer set being distinguishable from amplicons corresponding to each other primer set by means of a unique combination of amplicon size and observable label.

Another object of the present invention is to provide a kit for multiplexed DNA analysis, the kit being used in conjunction with a PCR system that may provide a DNA genetic profile, the kit further comprising a software template, the software template being capable of generating a forensic-related or bioancestry-related conclusion from the DNA genetic profile.

These and other objects may be attained by utilizing the mini-primer strategy with INNUL markers, which include SINEs, LINEs, and SVAs and can be effectively used as markers for human identification and bio-ancestry studies regardless of the size of the inserted element. The size of the amplicons for INNULs and the difference between allelic states can be reduced substantially such that these markers have utility for analyzing high and low quality human DNA samples. In addition, the present invention demonstrates a sensitivity of detection that can be sufficient to enable human identity and bio-ancestry studies on forensic and anthropological samples. Depending on the markers selected and the distribution of the alleles in global populations, INNULs can be selected for human identity testing or for bio-ancestry studies.

The optimization of INNUL markers into a single-tube, multi-locus reaction furthers these goals. The inclusion of these markers in a multiplexed reaction produces an INNUL-based human identity test set that is a powerful tool for use in forensic settings without the need for further investment in new instrumentation. The multiplexed system is able to amplify multiple target sequences at the same time with no non-specific amplification products and also exhibits the sensitivity to amplify DNA concentration as low as 100 pg or less. With a size range of 56-125 base pairs, this novel multiplexed system contains the smallest size amplicons that are both amenable for use with extensively degraded DNA samples and available to the forensic community. Thus, the INNUL multiplex system of the present invention provides a statistically discriminating tool that is useful for forensic applications where the sample is limited in quantity as well as quality.

One embodiment of the present invention includes a method for genetic detection comprising providing a sample to be analyzed; selecting a plurality of Retrotransposable element (RE) markers, each selected RE marker being an INNUL marker that is associated with both a filled allele representing a filled genomic site and an empty allele representing an empty genomic site, each INNUL marker comprising a nucleic acid sequence, the nucleic acid sequence being found at a location within the genome of a target species; providing a primer set corresponding to each selected INNUL marker, each primer set consisting of a forward primer and two reverse primers, the two reverse primers consisting of a primer corresponding to a filled site of the INNUL marker and a primer corresponding to an empty site of the INNUL marker, at least one primer in each primer set comprising an observable label, the three primers within each primer set being designed to generate an amplicon corresponding to the filled site of the INNUL marker and an amplicon corresponding to the empty site of the INNUL marker, the two amplicons differing from each other in size by about 2 to about 10 base pairs; combining the primer sets with the sample to form a reaction mixture; amplifying the markers using the primer sets to form a mixture of amplicon products; separating the amplicon products from the remainder of the reaction mixture and from each other on the basis of size; and detecting and quantitating each labeled amplification product, each marker being distinguished from each other marker by a unique combination of size and observable label.

In certain embodiments of the present invention, each forward primer used in the above method may have a structure comprising an observable label. In certain embodiments, at least one reverse primer of each primer set used in the above method may have a structure comprising an observable label. In certain embodiments, the observable labels may be a plurality of fluorescent organic dye moieties, but useful observable labels are not limited thereto.

In certain embodiments of the present invention, each forward primer used in the above method may have a structure comprising a fluorescent organic dye. In certain embodiments, at least one reverse primer of each primer set used in the above method may have a structure comprising a fluorescent organic dye.

In certain embodiments of the present invention, the observable labels may be selected from 6 carboxyfluorescein (sold as 6-FAM; also denoted "FAM" for the present purpose), 6-carboxy-4',5'-dichloro-2',7'-dimethoxyfluorescein (sold as JOE), 6-carboxytetramethylrhodamine (sold as TAMRA) and a label comprising at least one of 5-carboxy-X-rhodamine and 6-carboxy-X-rhodamine (sold as ROX).

In certain embodiments of the present invention, the reaction products may be separated from the remainder of the PCR reaction mixture and from each other using a separator that carries out electrophoresis.

In certain embodiments of the present invention, each amplification product may be labeled with a distinct observable label.

In certain embodiments of the present invention, an observable label may be associated with each primer set, the observable label being selected from a plurality of distinct observable labels which may be distributed among the selected INNUL markers, so that each selected INNUL marker may be distinguished from each other selected INNUL marker by a unique combination of PCR amplicon size and observable label.

In certain embodiments of the present invention, the observable labels comprise a plurality of fluorescent organic dye moieties, at least one primer of each primer set comprising a fluorescent dye moiety, each primer set corresponding to a selected INNUL marker.

In certain embodiments of the inventive method for genetic detection of the present invention, the separating step comprises electrophoresis.

In certain embodiments of the inventive method for genetic detection of the present invention, the amplifying step may include the use of a real-time polymerase chain reaction (PCR) system. In certain embodiments, the amplifying step may include the use of a quantitative real-time polymerase chain reaction (QPCR) system.

In certain embodiments of the present invention, each primer set may correspond to a set of PCR amplicons comprising a PCR amplicon corresponding to a filled allele and a PCR amplicon corresponding to an empty allele, and each PCR amplicon may have a size of from about 46 base pairs to about 200 base pairs. Alternatively, in each set of PCR amplicons, each PCR amplicon may have a size of from about 60 base pairs to about 200 base pairs.

In certain embodiments of the present invention, the selected INNUL markers may be selected from SINEs, LINEs and SVAs.

In certain embodiments of the present invention, the selected INNUL markers may be selected from Alus and LINEs.

In some embodiments of the present invention, the set of INNUL markers used may be selected for human identity testing purposes on the basis of the distribution of the alleles in global populations.

In some embodiments of the present invention, the set of INNUL markers used may be selected for bio-ancestry studies on the basis of the distribution of the alleles in global populations.

In some embodiments of the method for genetic detection of the present invention, the sample to be analyzed may be a DNA sample, and the method may further comprise performing a population study and determining that the combined group of selected retrotransposable element (RE) markers provides for a power of discrimination among individuals of a target species of at least 1 in 1000.

In some embodiments of the method for genetic detection of the present invention, the sample to be analyzed may be a human DNA sample, and the method may further provide a paternity determination, the combination of the selected group of retrotransposable element (RE) markers may provide for a probability of discrimination of at least 0.999, and the probability may be determined by parentage analysis of 100 or fewer cases containing samples from mother, child and alleged father.

In some embodiments of the method for genetic detection of the present invention, the sample to be analyzed may be a human DNA sample, and the method may further provide a paternity determination, the combination of the selected group of retrotransposable element (RE) markers may provide for a probability of discrimination of at least 0.99999, and the probability may be determined by parentage analysis of 100 or fewer cases containing samples from mother, child and alleged father.

In certain embodiments of the present invention, useful forensic or bio-ancestry-related determinations may be obtained for samples comprising as little as 100 pg of DNA. In other embodiments, useful forensic or bio-ancestry-related determinations may be obtained for samples comprising no more than 5 ng of DNA.

In certain embodiments of the present invention, each selected INN UL marker comprises a Target Site Duplication (TSD) sequence, also referred to as a direct repeat sequence, and each reverse primer comprises a nucleic acid sequence that includes all or part of the TSD sequence.

In certain embodiments of the present invention, the genetic detection method may include INNUL markers selected from CHR20-79712, Ya5-MLS48, Yb8NBC13, Ya5ACA1736, Yb8NBC106, Y5ac2305, HS4.69, AC4027, CH1-6217, Yb8AC1796, Yac52265, MLS9, TARBP1, SVA306, Amelogenin, SVA323, Ya5NBC51, Yb8AC1141, Yb7AD155 and Ya5-MLS18. In one embodiment, a multiplex system for genetic detection may comprise the amplification of filled and empty amplicons corresponding to each of fifteen of these INNUL markers plus Amelogenin.

In certain embodiments of the present invention, the genetic detection method may include INNUL markers selected from CHR20-79712, Ya5-MLS48, Ya5ACA1736, Yb8NBC106, Yb8AC1141, Ya5-MLS18, Yb8NBC13, Ya5ac2265, Ya5-MLS09, TARBP1, Ya5NBC241, HS4.69 (NC000005.10), Ya5NBC51, Ya5ACA1766 and CH1-2250 plus Amelogenin. However, the genetic detection method of the present invention is not limited thereto. In some embodiments, a multiplex system for genetic detection may comprise the simultaneous amplification of filled and empty amplicons corresponding to each of these fifteen INNUL markers plus Amelogenin.

In certain embodiments of the present invention, the genetic detection method may include INNUL markers selected from Ya5-MLS09, TARBP1, Yc1RG148, Ya5-MLS26, Yb8AC1141, Ya5NBC51, Yb9NBC10, HS4.69 (NC000005.10), AC004027, Ya5NBC216, Ya5ACA1766, Ya5ac2265, Ya5ac2305, Yb8NBC148, Yb8NBC13, Ya5NBC102, Sb19.12, CHR20-79712, Yb8NBC106 and Yb8NBC120 plus Amelogenin. However, the genetic detection method of the present invention is not limited thereto. In some embodiments, a multiplex system for genetic detection may comprise the simultaneous amplification of filled and empty amplicons corresponding to each of these twenty INNUL markers plus Amelogenin.

In certain embodiments of the present invention, the reaction products may be separated from the remainder of the PCR reaction mixture and from each other using electrophoresis.

In certain embodiments of the present invention, each INNUL marker may comprise a filled allele and an empty allele, and the size difference between PCR amplicons generated by each filled allele and the corresponding empty allele may be in the range of from about 2 to about 8 base pairs. In certain other embodiments, the size difference between PCR amplicons generated by each filled allele and the corresponding empty allele may be in the range of from about 2 to about 10 base pairs.

In some embodiments of the present invention, the useful conclusion obtained from the multiplexed DNA analysis system is a forensic-related conclusion.

In some embodiments of the present invention, the useful conclusion obtained from the multiplexed DNA analysis system is a bioancestry-related conclusion.

Embodiments of the present invention may include a multiplexed DNA analysis system comprising a sample of DNA, a set of thirty or fewer INNUL markers, each INNUL marker comprising a filled allele and an empty allele, a set of three primers corresponding to each INNUL marker, each set of primers including a forward primer and two reverse primers, the forward primer including a detectable label, one reverse primer corresponding to the filled allele and the other reverse primer corresponding to the empty allele, a polymerase chain reaction (PCR) amplification system that produces two PCR amplicons corresponding to each primer set, the amplicons being produced by amplifications initiated by each set of three primers and differing from each other in size by about 2 to about 10 base pairs, an separator for separating PCR amplicons from reactants and from each other, an intermediate stage detecting and quantitating PCR amplicons using the detectable labels, each INNUL marker being distinguished from each other INNUL marker by a unique combination of amplicon size and detectable label, and a second stage generating a useful forensic-related or bioancestry-related conclusion from the quantitative PCR results.

In certain embodiments of the present invention, the multiplexed DNA analysis system may include INNUL markers selected from CHR20-79712, Ya5-MLS48, Ya5ACA1736, Yb8NBC106, Yb8AC1141, Ya5-MLS18, Yb8NBC13, Ya5ac2265, Ya5-MLS09, TARBP1, Ya5NBC241, HS4.69 (NC000005.10), Ya5NBC51, Ya5ACA1766 and CH1-2250 plus Amelogenin. However, the multiplexed DNA analysis system of the present invention is not limited thereto. In some embodiments, a multiplex system for genetic detection may comprise the simultaneous amplification of filled and empty amplicons corresponding to each of these fifteen INNUL markers plus Amelogenin.

In certain embodiments of the present invention, the multiplexed DNA analysis system may include INNUL markers selected from Ya5-MLS09, TARBP1, Yc1RG148, Ya5-MLS26, Yb8AC1141, Ya5NBC51, Yb9NBC10, HS4.69 (NC000005.10), AC004027, Ya5NBC216, Ya5ACA1766, Ya5ac2265, Ya5ac2305, Yb8NBC148, Yb8NBC13, Ya5NBC02, Sb19.12, CHR20-79712, Yb8NBC106 and Yb8NBC120 plus Amelogenin. However, the multiplexed DNA analysis system of the present invention is not limited thereto. In some embodiments, a multiplexed DNA analysis system may comprise the simultaneous amplification of filled and empty amplicons corresponding to each of these twenty INNUL markers plus Amelogenin.

In certain embodiments of the present invention, the means for separating PCR amplicons from reactants and from each other within the multiplexed DNA analysis system may be electrophoresis.

In certain embodiments of the present invention, the sample of DNA may comprise no more than 100 pg of DNA. In other embodiments, the sample of DNA may comprise no more than 5 ng of DNA.

In certain embodiments of the present invention, the PCR amplification system may be a real-time PCR system or a quantitative real-time PCR system.

In certain embodiments of the present invention, the multiplexed DNA analysis system may be based on amplification of a set of 20 INNUL allele markers plus Amelogenin.

In certain embodiments of the present invention, the multiplexed DNA analysis system may be based on amplification of a set of 15 INNUL allele markers plus Amelogenin.

In certain embodiments of the present invention, the multiplexed DNA analysis system may include forward primers that are labeled with fluorescent organic dyes. In some embodiments, the fluorescent organic dyes may be selected from the group of four dyes consisting of 6-carboxyfluorescein (sold as 6-FAM), 6-carboxy-4',5'-dichloro-2',7'-dimethoxyfluorescein (sold as JOE), 6-carboxytetramethylrhodamine (sold as TAMRA) and 6-carboxy-X-rhodamine (sold as ROX). In some embodiments, the multiplexed DNA analysis system may make use of a combination of four or five fluorescent organic dyes as detectable labels.

In some embodiments of the multiplexed DNA analysis system of the present invention, the sample of DNA may be a sample of human DNA, and the second stage generating a useful conclusion may be the use of allele insertion frequency population data to make a determination of paternity or other human familial relationship.

In some embodiments of the multiplexed DNA analysis system of the present invention, the means for deriving a useful conclusion may be the use of allele insertion frequency population data to make a determination of race from a sample of human DNA.

In some embodiments of the multiplexed DNA analysis system of the present invention, the sizes of the amplicons may range from about 60 base pairs to about 200 base pairs.

In certain embodiments of the present invention, the amplicon products of the above methods and systems may be characterized by Next Generation Sequence analysis (NGS) methods.

In certain embodiments of the present invention, the amplicon products of the above methods and systems may be characterized by rapid DNA analysis platforms.

BRIEF DESCRIPTION OF THE FIGURES

The patent or application file contains at least one drawing executed in color. Copies of this patent or patent application publication with color drawing(s) will be provided by the Office upon request and payment of the necessary fee.

A more complete appreciation of the invention, and many of the attendant advantages thereof, will be readily apparent as the same becomes better understood by reference to the following detailed description when considered in conjunction with the accompanying figures, wherein.

The Alu sequence is represented by the shaded line. The chromosomal locus harboring the Alu element is represented by the thick dark line, and the flanking unique sequence derived PCR primers are denoted by the arrows.

The PCR assay results in the production of approximately a 100 bp or a 400 bp DNA fragment or both as outlined in the figure. Individuals that are homozygous for the Alu insertion will amplify only 400 bp fragment (#1), while those that are homozygous for the absence of Alu insertion at this locus will amplify only a 100 bp fragment (#3). Individuals heterozygous for the Alu insertion will amplify both the 400 bp and 100 bp fragments (#2).

FIG. 3A illustrates a primer design for the filled site of retrotransposable element (RE) marker Ya5ac2305. The primer sequences for mini-primer design are underlined. The traditional "core primer" design sequences, as reported earlier, are in bold and italics.

FIG. 3B illustrates the corresponding empty site of retrotransposable element (RE) marker Ya5ac2305 in the primer design of FIG. 3A. Primer sequences for the mini-primer design are underlined.

The forward primer is identical in both sites. The uniqueness for each site lies within the reverse primer sequences. In the Filled Site reaction (FIG. 3A), the reverse primer contains the direct repeat sequence (in red), flanking genomic sequence and some of the 5' Alu insert sequence (blue letters). The Empty Site reaction (FIG. 3B) reverse primer contains the whole direct repeat plus flanking genomic sequence.

Figure 1A:
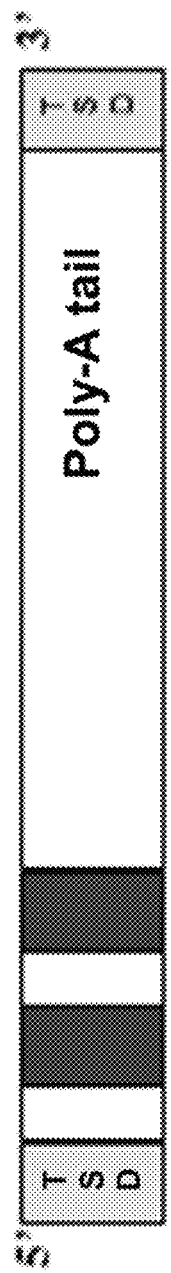
FIG. 1A illustrates the structure of Alu retrotransposable elements. The full-length Alu retrotransposon is not drawn to scale. As represented, Alu REs have at the beginning and end a target site duplication (TSD) consisting of identical DNA sequences. The mini primer design strategy exploits these TSDs for amplification and detection of insertion or null alleles.
Figure 1B:
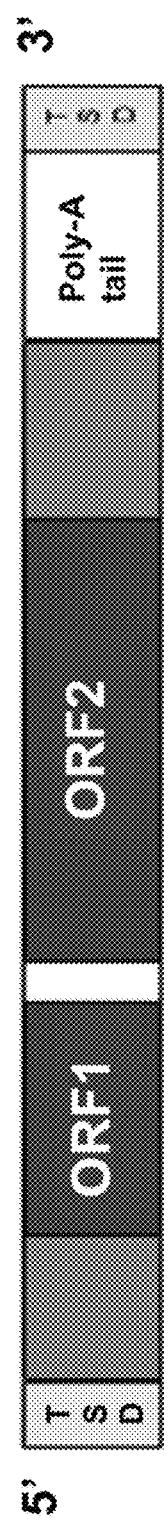
FIG. 1B illustrates the structure of a long interspersed nuclear element (LINE1). The full-length LINE1 retrotransposon is not drawn to scale. As represented, LINE1 REs have at the beginning and end a target site duplication (TSD) consisting of identical DNA sequences.
Figure 1C:
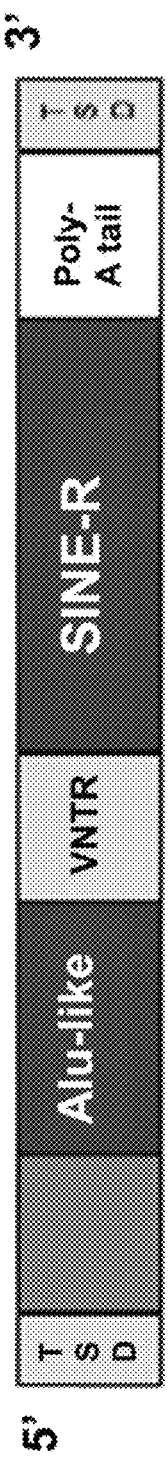
FIG. 1C illustrates the structure of a SVA (SINE/VNTR/Alu) element. The full-length LINE1 retrotransposon is not drawn to scale. As represented, LINE1 REs have at the beginning and end a target site duplication (TSD) consisting of identical DNA sequences.
Figure 2A:
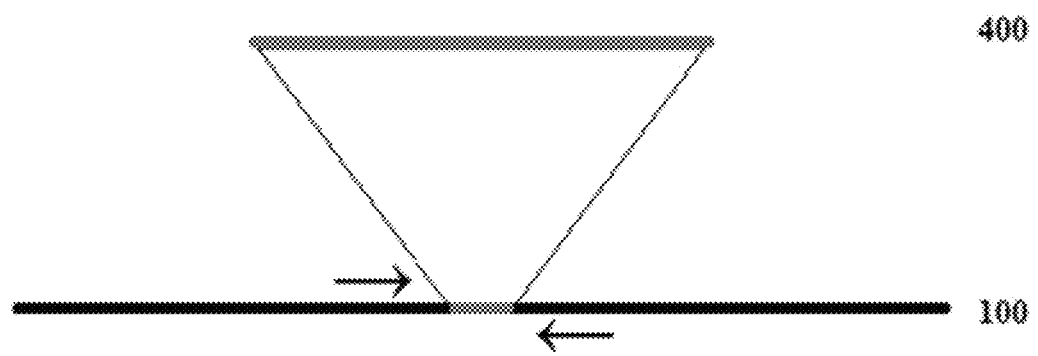
FIG. 2A illustrates the schematic of the Alu element insertion PCR assay of the prior art.
Figure 2B:
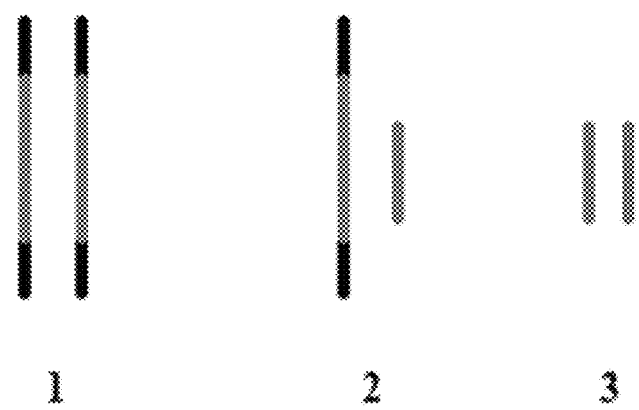
FIG. 2B is a schematic showing relative amplicon lengths obtained with the Alu element insertion PCR assay of the prior art for each genotype—homozygous filled, heterozygote and homozygous empty.
Figure 4:
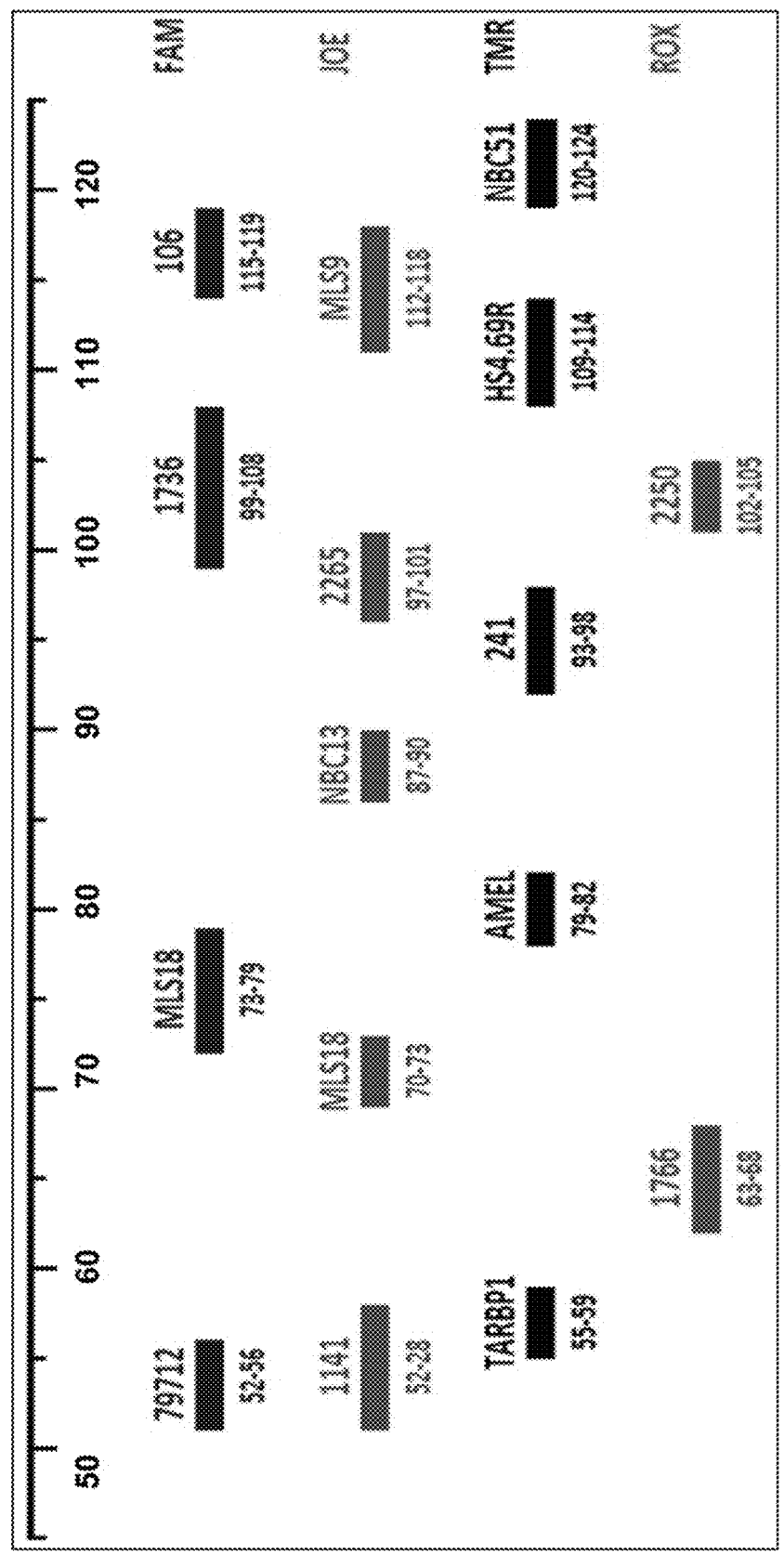

FIG. 4 illustrates a multiplex design showing 15 markers plus amelogenin, dyes, and amplicon sizes for each locus.

Figure 5:
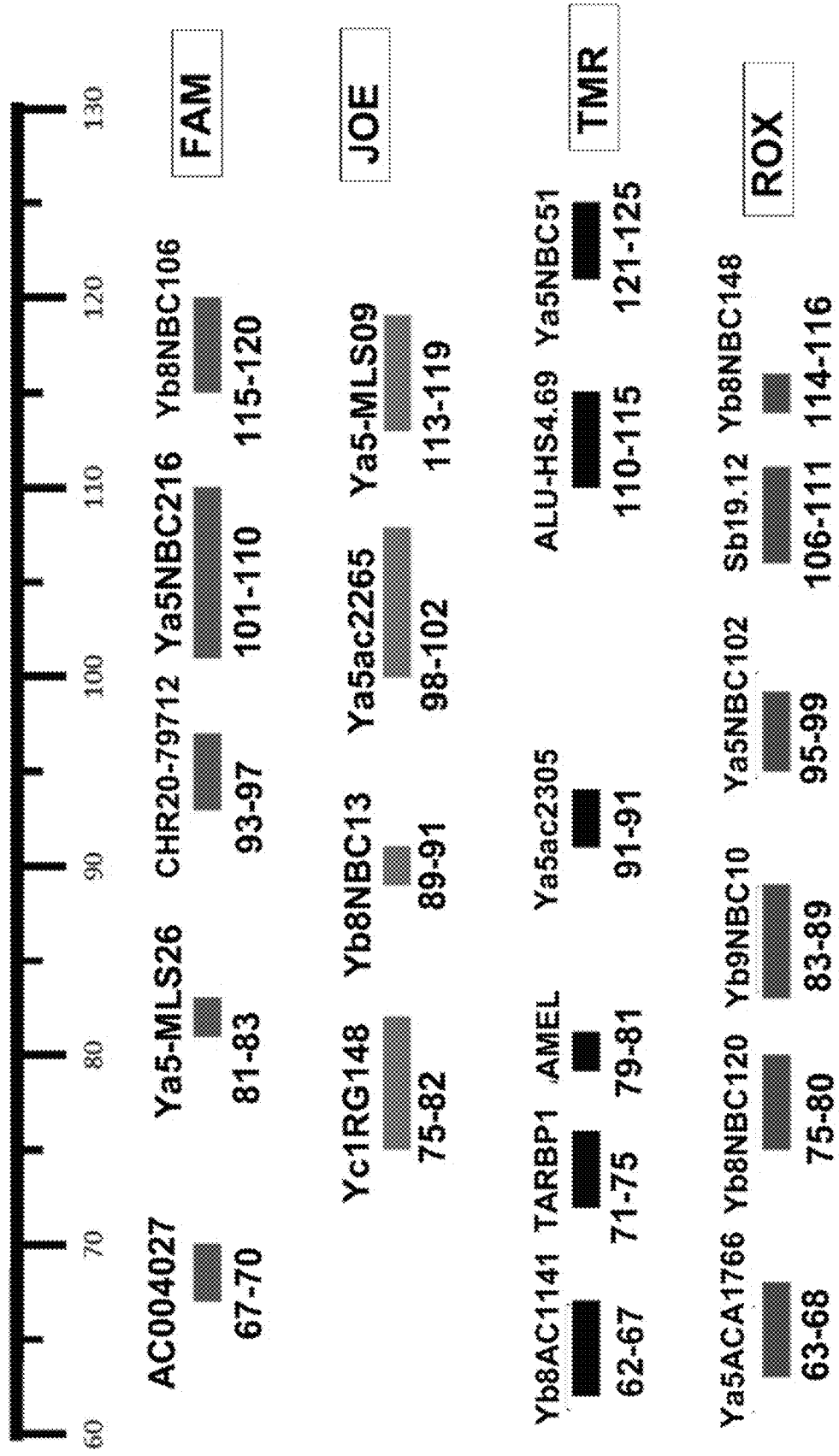

FIG. 5 illustrates a multiplex design showing 20 markers plus amelogenin, dyes, and amplicon sizes for each locus.

Figure 6A:
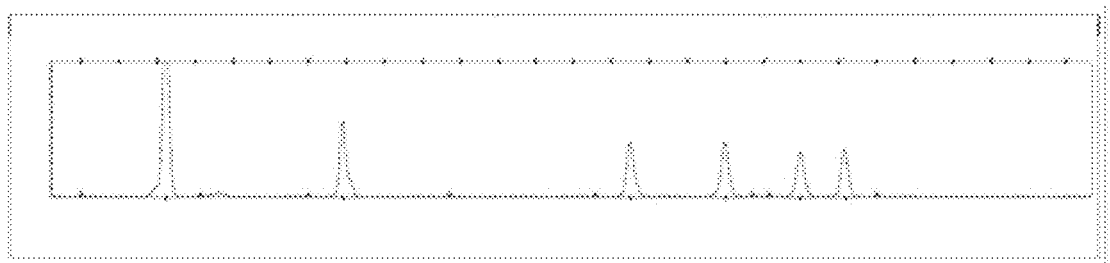

FIG. 6A illustrates peaks visualized with the 6-FAM (blue) fluorophore in an electropherogram representing InnoTyper™, which includes 15 retrotransposable element (RE) markers and Amelogenin multiplexed using five fluorophores: 6-FAM (blue), JOE (green), TMR (TAMRA, black but represents yellow), ROX (red), and CC5 (orange) as the size standard. Results were obtained using an ABI Prism® 3130 Genetic Analyzer (Applied Biosystems). The fluorophores may be represented as 6-carboxyfluorescein (sold as 6-FAM) 1, 6-carboxy-4',5'-dichloro-2',7'-dimethoxyfluorescein (sold as JOE) 2, 6-carboxytetramethylrhodamine (sold as TAMRA) 3, or 6-carboxy-X-rhodamine (sold as ROX) 4. ROX may be a mixture of the 6-carboxy-isomer 4 and the 5-carboxy-isomer 5. The "X" groups are "linker" groups that connect an oligonucleotide to a dye label. As is well known in the art, various amide or other groups may be used as linkers.

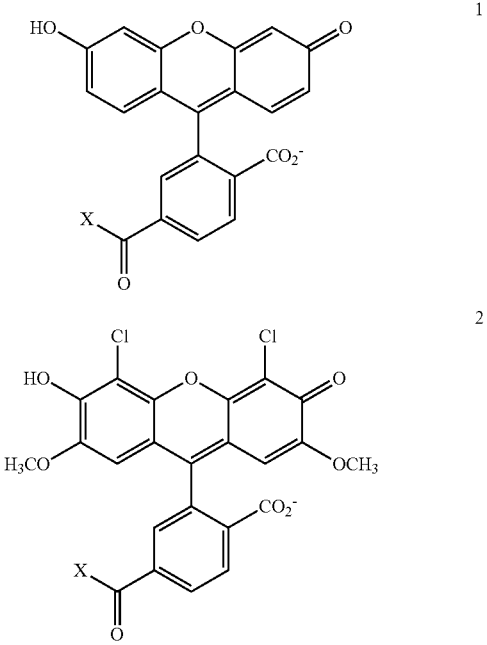

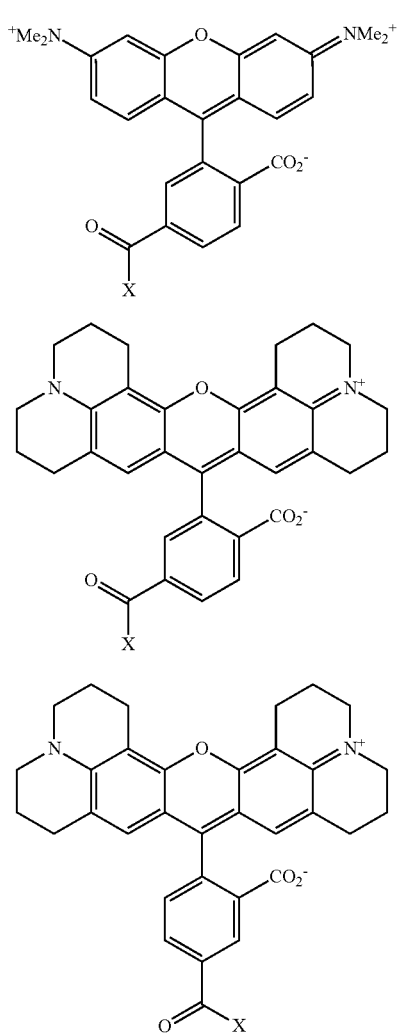

Figure 6B:
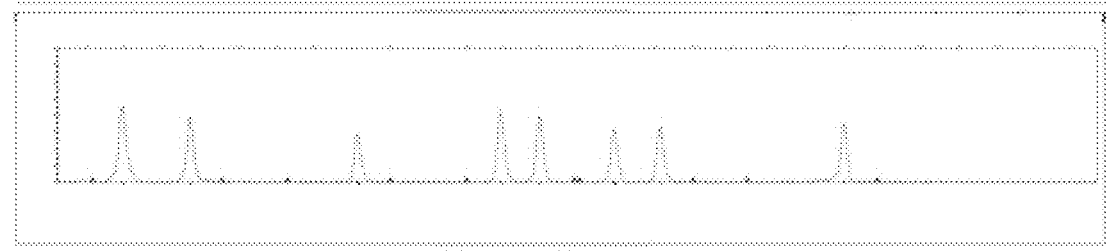

FIG. 6B illustrates peaks visualized with the JOE (green) fluorophore in an electropherogram representing Inno-Typer™.

Figure 6C:
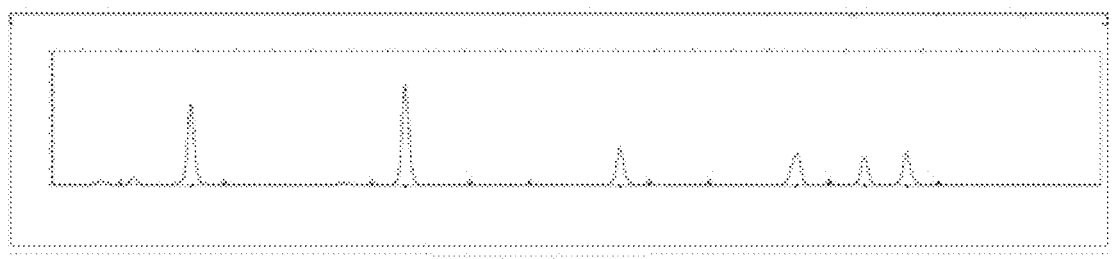

FIG. 6C illustrates peaks visualized with the TAMRA (black but represents yellow) fluorophore in an electropherogram representing InnoTyper™.

Figure 6D:
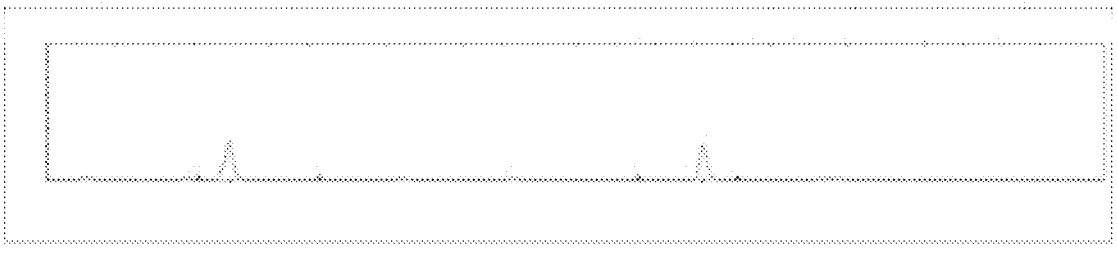

FIG. 6D illustrates peaks visualized with the ROX (red) fluorophore in an electropherogram representing Inno-Typer™.

Figure 6E:
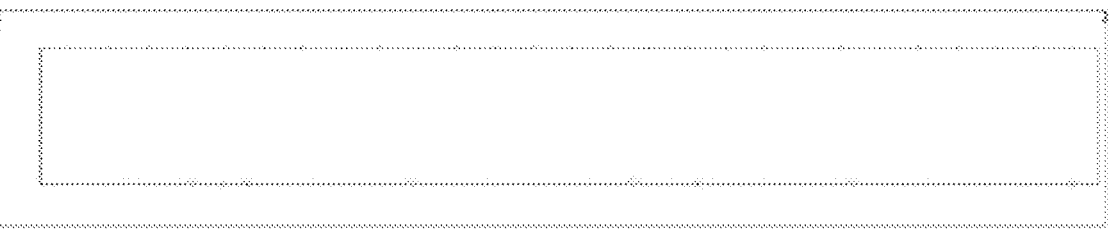

FIG. 6E illustrates peaks visualized with the CC5 (orange) fluorophore, used as a size standard, in an electropherogram representing InnoTyper™.

Figure 7A:
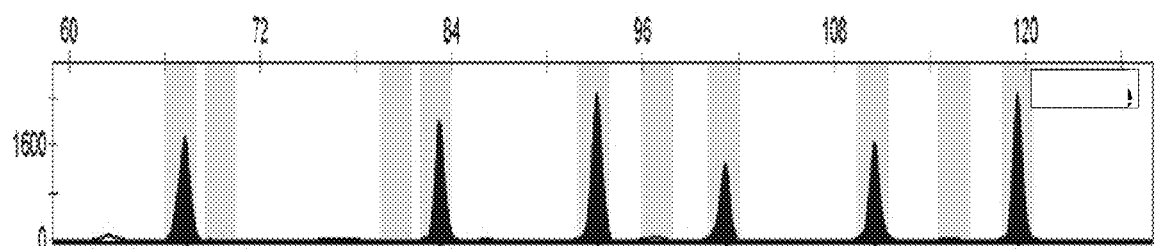

FIG. 7A illustrates peaks visualized with the 6-FAM (blue) fluorophore in an electropherogram representing InnoTyper 21™, which includes 20 retrotransposable element (RE) markers and Amelogenin multiplexed using four fluorophores: 6-FAM (blue), JOE (green), TMR (TAMRA, black but represents yellow) and ROX (red). Results were obtained using a 3130 Genetic Analyzer.

Figure 7B:
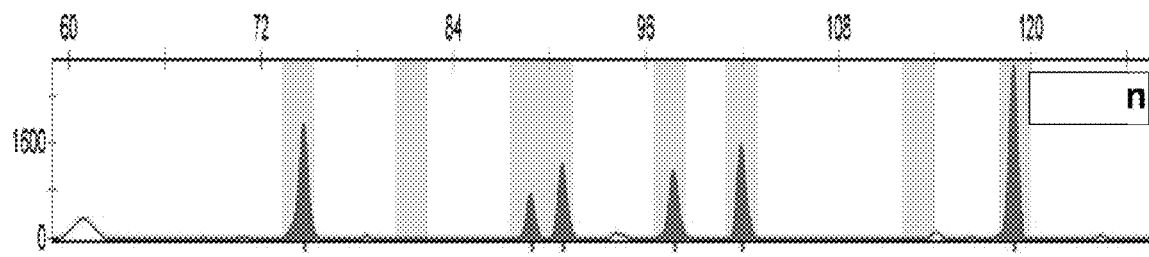

FIG. 7B illustrates peaks visualized with the JOE (green) fluorophore in an electropherogram representing InnoTyper 21™.

Figure 7C:
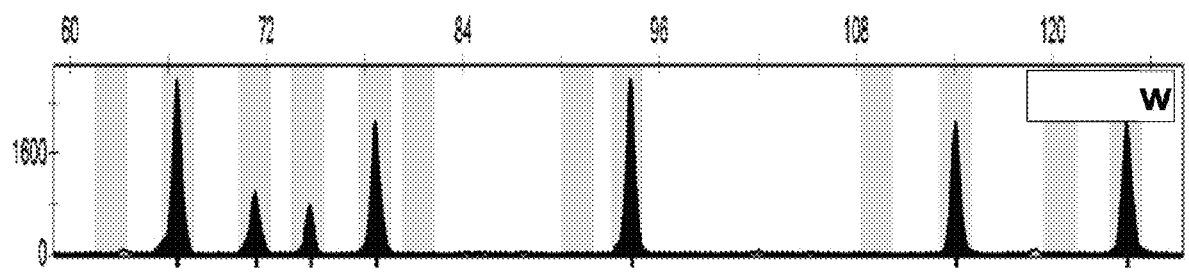

FIG. 7C illustrates peaks visualized with the TAMRA (black but represents yellow) fluorophore in an electropherogram representing InnoTyper 21™.

Figure 7D:
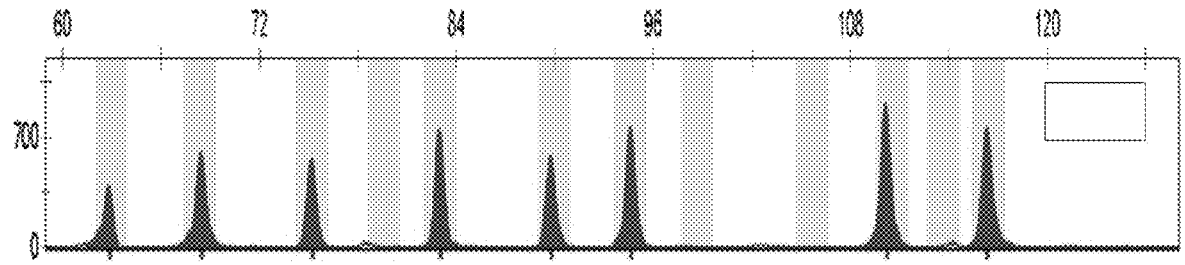

FIG. 7D illustrates peaks visualized with the ROX (red) fluorophore in an electropherogram representing InnoTyper 21™.

Figure 8:
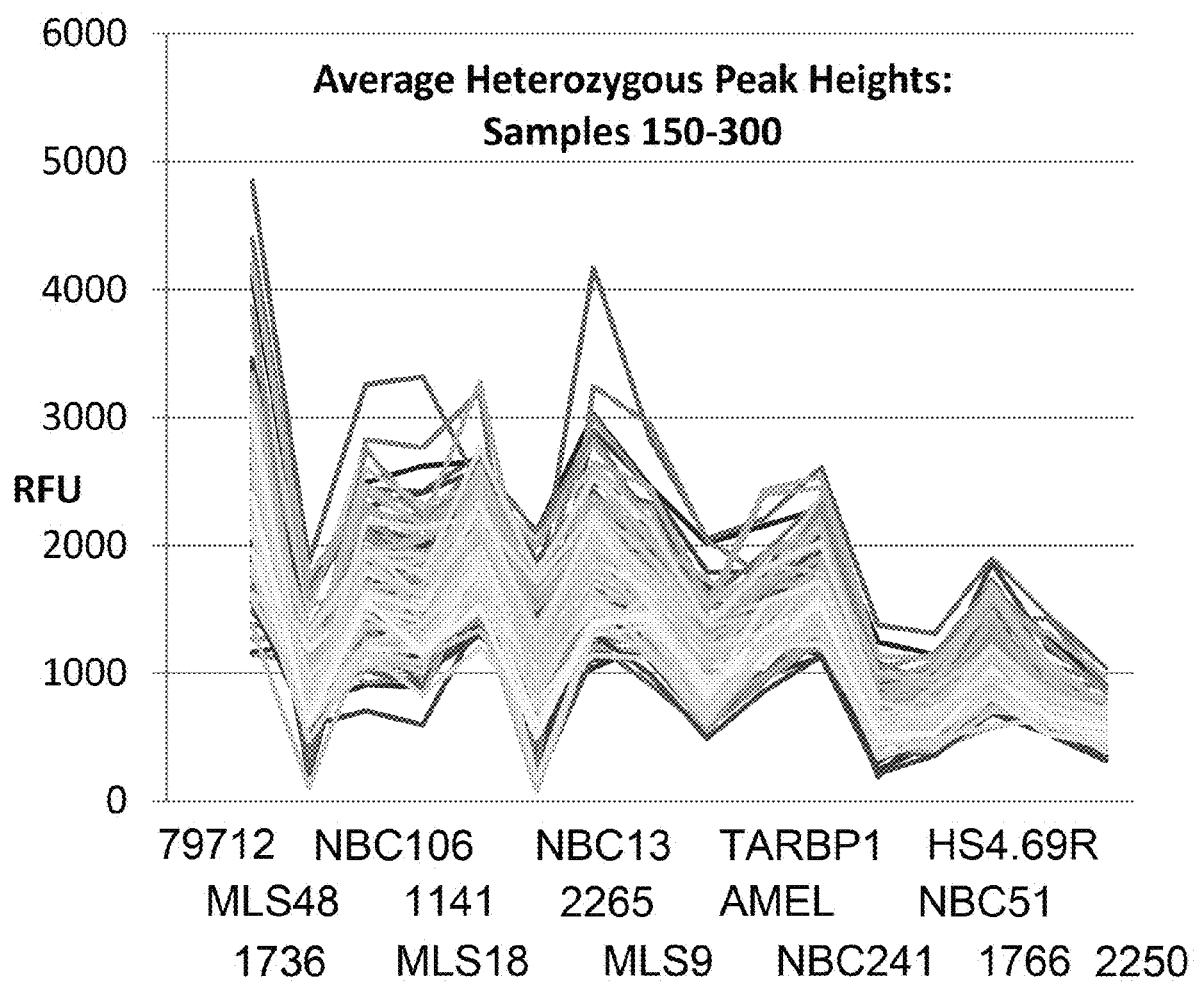

FIG. 8 illustrates average heterozygous peak heights for 150 database samples. RFU vs. Marker.

Figure 9:
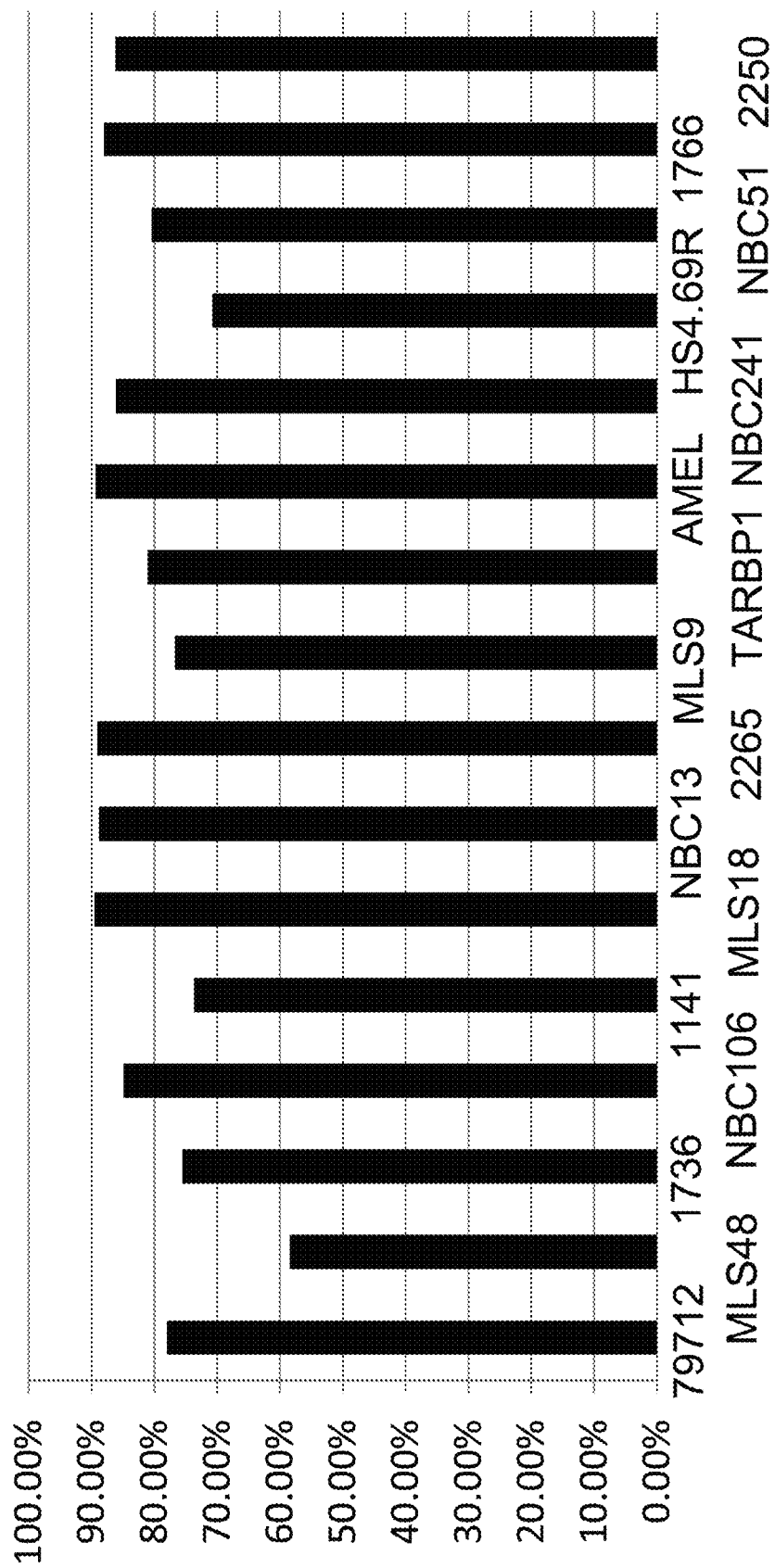

FIG. 9 illustrates a heterozygosity of database samples.

Figure 10:
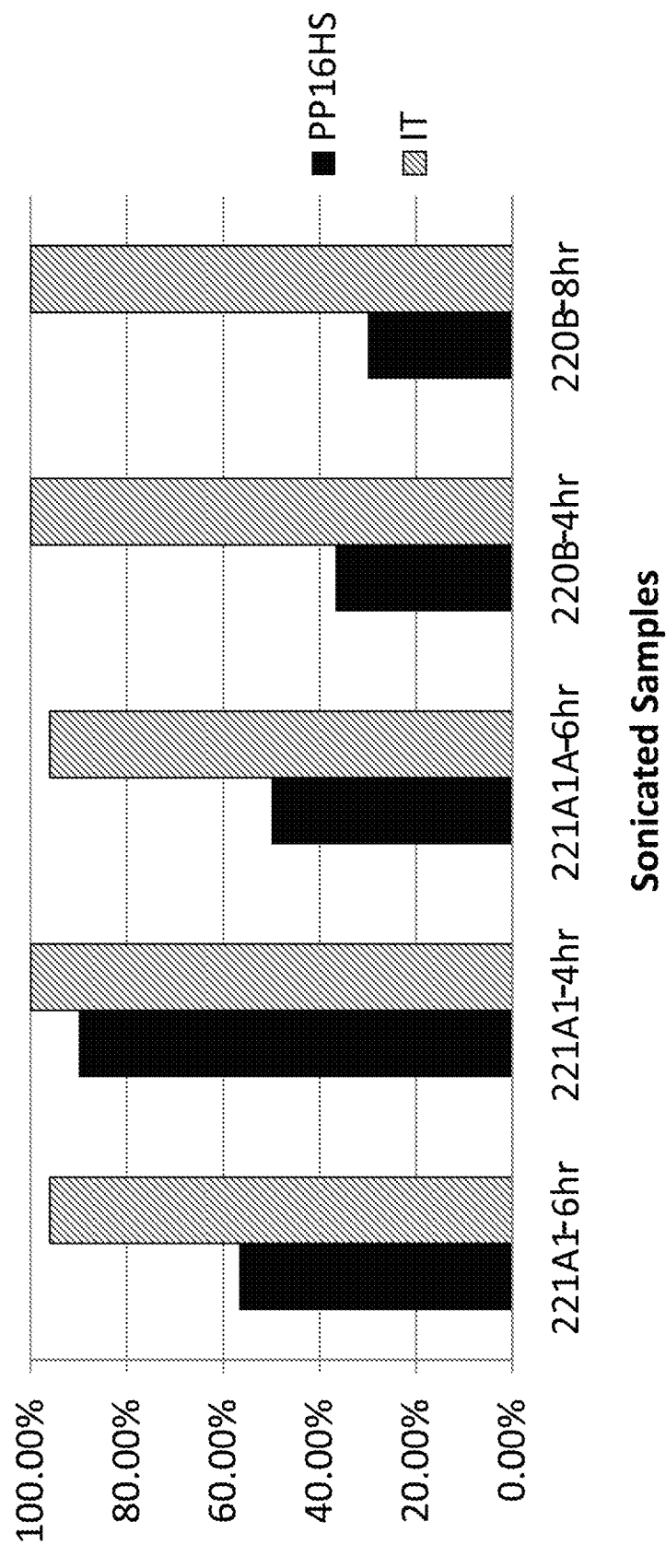

FIG. 10 illustrates the PowerPlex® 16HS (PP16HS) vs. InnoTyper™ (IT). Results confirmed that InnoTyper™ was two times more sensitive in number of alleles detected.

Figure 11:
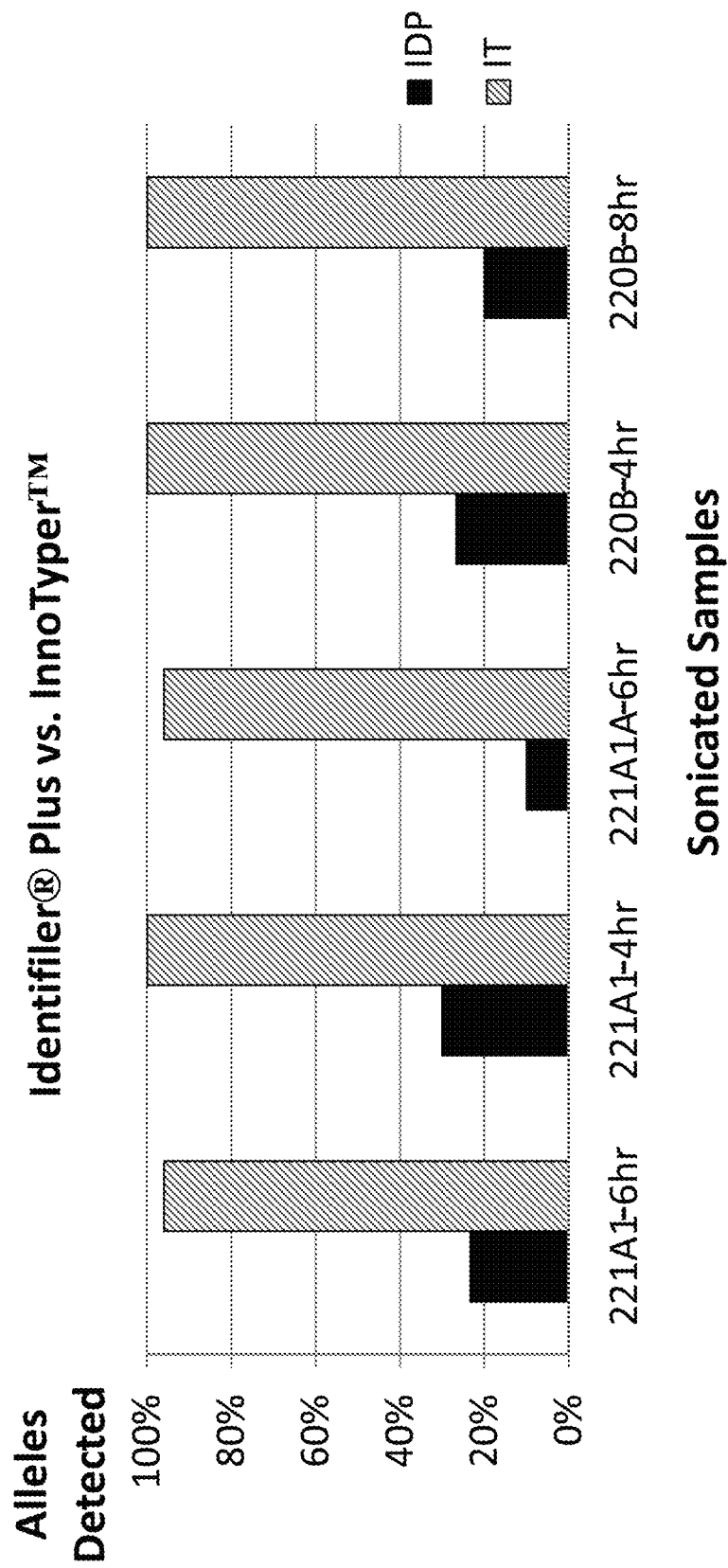

FIG. 11 illustrates the Identifiler® Plus (IDP) vs. Inno-Typer™ (IT). Results confirmed that InnoTyper™ was four times more sensitive in number of alleles detected.

Figure 12:
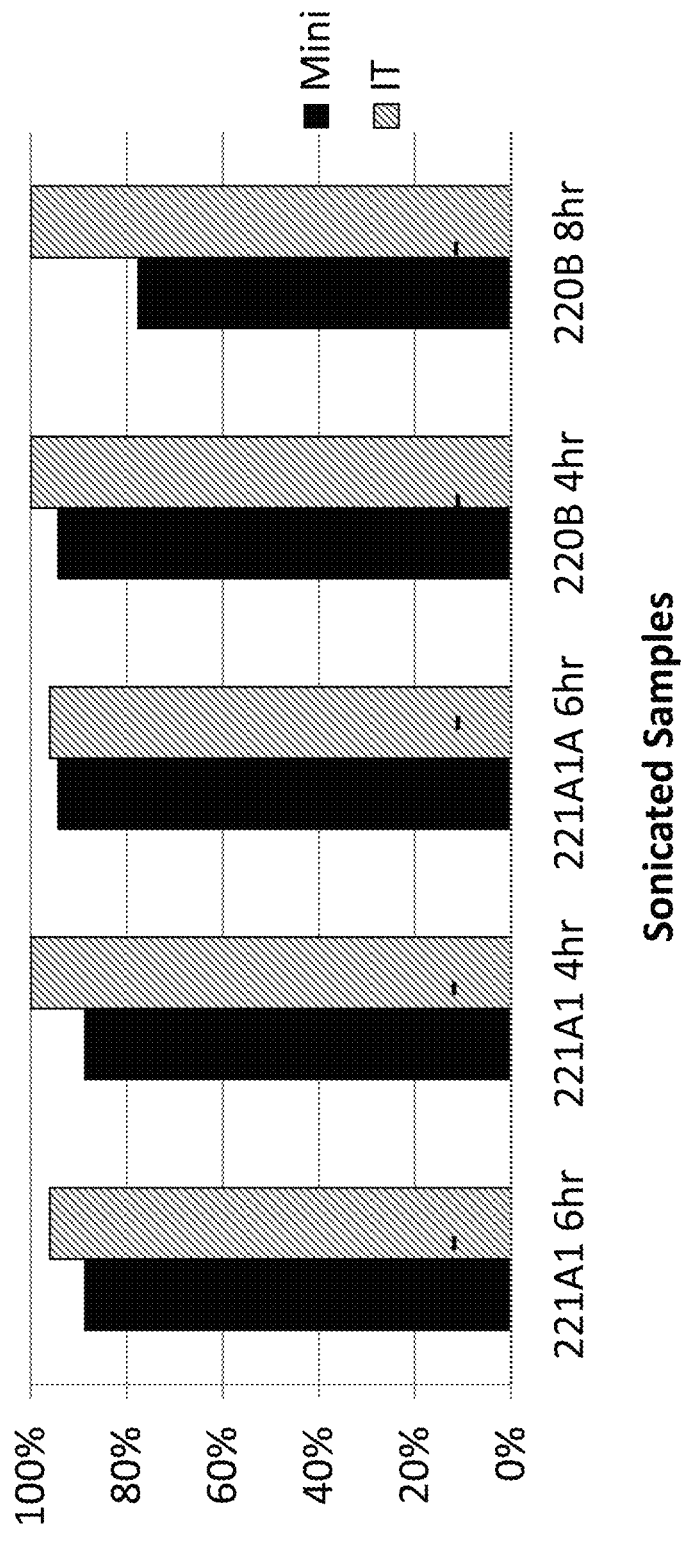

FIG. 12 illustrates the Minifiler Plus™ (Mini) vs. Inno-Typer™ (IT) multiplex. Results confirmed that InnoTyper™ was ten percent more sensitive in number of alleles detected.

FIGS. 13A-13D illustrate a comparison of degraded DNA profiles using STR kits. These figures show electropherograms depicting multiplex analysis of DNA after sonication for eight hours.

FIG. 13A shows electropherograms depicting multiplex analysis of DNA after sonication for eight hours using PowerPlex® 16HS (Promega) (average peak height=373 RFU).

FIG. 13B shows electropherograms depicting multiplex analysis of DNA after sonication for eight hours using Identifiler® Plus (Applied Biosystems) (average peak height=111 RFU).

FIG. 13C shows electropherograms depicting multiplex analysis of DNA after sonication for eight hours using Minifiler™ (Applied Biosystems) (average peak height=384 RFU).

FIG. 13D shows electropherograms depicting multiplex analysis of DNA after sonication for eight hours using the InnoTyper™ 16 marker multiplex (Innogenomics, LLC) (average peak height=956 RFU).

FIG. 14 illustrates a sensitivity study of markers showing the average peak height of empty and filled primers at varying concentrations of DNA (0.5-0.05 ng/µL). Empty results showed slightly higher peak intensities than Filled results.

Figure 15A:
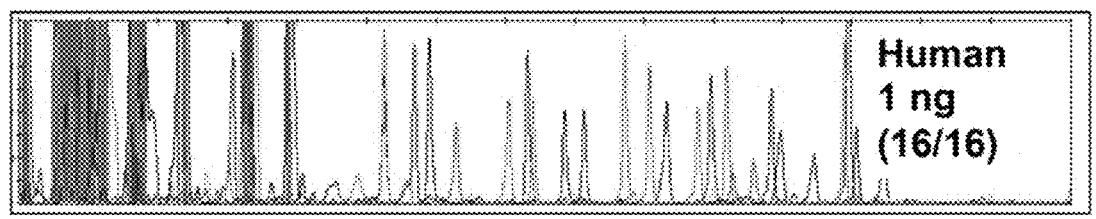

FIG. 15A illustrates an electropherogram obtained using InnoTyper™ and a human DNA sample.

Figure 15B:

FIG. 15B illustrates an electropherogram obtained using InnoTyper™ and an orangutan DNA sample.

Figure 15C:

FIG. 15C illustrates an electropherogram obtained using InnoTyper™ and a cat DNA sample.

Figure 15D:
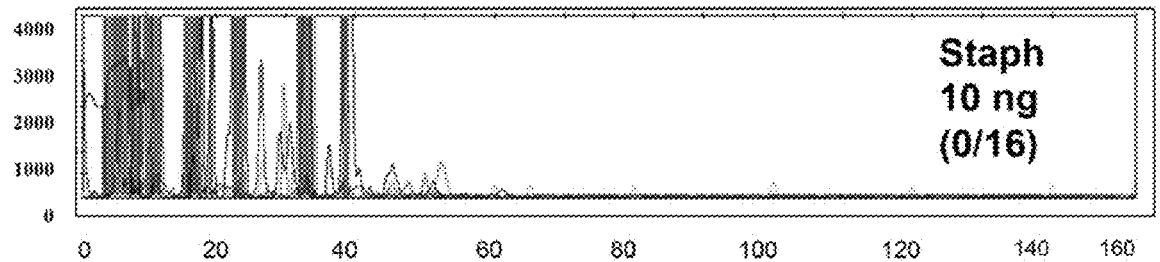

FIG. 15D illustrates an electropherogram obtained using InnoTyper™ and a staph DNA sample.

DETAILED DESCRIPTION OF THE INVENTION

Embodiments of the present invention provide for the first time for the use of LINEs, SINEs, or SVA element insertions for forensic applications. One object of the present invention is to design and obtain synthetic primers based on the mini-primer design (see U.S. Pat. No. 7,794,983 B2, to Sinha, et al.) for Interspersed Element Insertion polymorphisms that would produce small PCR products that include as few as 50 to 150 base pairs (bp) when human genomic DNA is amplified. All retrotransposon insertion has a characteristic sequence that appears at the beginning and again at the end of insertion, and this is referred to as Target Site Duplication (TSD). One embodiment of the present invention includes the design of synthetic primers to include a part or full TSD sequence in order to quantitate specific insertion or no-insertion alleles using a multiplex system. In another embodiment of the present invention, based on the power of discrimination and analytical performance, markers were selected and chosen as suitable for either forensic or bioancestry applications. Another embodiment of the present invention provides for the design, optimization and validation of a multiplex amplification system (single amplification for multiple targets) containing LINEs, SINEs, and SVAs for forensic applications.

In addition to developing a practical method for using SINEs for genotyping individuals, the present invention demonstrates for the first time that LINEs and SVAs can be used as potential markers for human identification. Fifteen forensically suitable markers were selected to include in a 4-dye multiplex system. Among the 15 markers (including LINEs and Alu), the amplicon sizes ranged between 56 and 125 bp. A population study using 51 Caucasian and 51 African American samples was performed using 11 fluorescently labeled primer sets. The same 102 samples were analyzed with STR and compared with the RE results by a statistician. The data indicated that the retrotransposable element (RE) markers are statistically independent of STR loci as well as among themselves. This statistical independence is critically important in establishing the validity of the use of RE markers for the forensic evaluation of DNA. The total power of discrimination for the combination of only these 11 markers was greater than 1 in 1000s for the Caucasian population and almost 10 fold more, greater than 1 in 10,000, for the African American population. The ability to discriminate among samples will only increase with the addition of more loci.

A degradation study was performed to assess the performance of retrotransposable element (RE) markers on compromised samples, such as those encountered in forensic cases. Results demonstrate that the system is successful in obtaining meaningful results from highly degraded DNA.

A sensitivity study was performed to establish the minimum DNA quantity from which results can accurately be obtained. This study has demonstrated that bi-allelic INNULs in the range of 56-125 bp in size can be multiplexed for genotyping of individuals and provide a sensitivity of detection and a power of discrimination that would make them useful for human identification of degraded samples.

The following will describe an organization of REs and a primer design strategy that may be useful in certain embodiments of the inventive multiplex system.

In one embodiment of the present invention, synthetic primers are provided, the synthetic primers including part or full TSD sequences and being capable of amplifying specific insertion or no-insertion alleles within a multiplex system. Interpretation of the results obtained using these primers will depend upon the earlier described characterization of respective allele frequencies of dimorphic Alu repeats in various population groups. The allele frequencies of these repeats can be quite variable, ranging from as low as 0.01 for HS4.65 among US Caucasians, to as high as 0.99 for HS3.23 among African-Americans. Several of the Alu elements have heterozygosity values approaching 0.5, the theoretical maximum for bi-allelic loci. A survey of numerous dimorphic Alu repeats across several worldwide population groups reveals that approximately 80% of the markers display allele frequencies between 0.3-0.7.

For paternity testing, these frequencies are ideal for the calculation of exclusion and inclusion probabilities (Wang, J., et al., *dbRIP: A highly integrated database of retrotransposon insertion polymorphisms in humans*, Human Mutation, 27(4): 323-329 (2006)). The few markers that are present in very high frequencies within specific population groups are extremely useful for estimating the geographic origin of unknown samples in forensic casework. In general, by genotyping any unknown sample using all the dimorphic Alu repeats that have been characterized to date, it is possible to ascertain the geographic origin of the sample with a very high degree of certainty (Benson, D. A., et al., *GenBank*, Nucleic Acids Research, 33 (suppl. 1): D34-D38 (2005)).

Alus are bi-allelic with a large size difference (of 300 base pairs) between the filled (contains Alu) and empty (absent for Alu) sites. Fundamental design flaws have appeared in Alu primer designs of the prior art. When several primer sets are multiplexed, subsequent allele "drop-out" occurs and is due to allele size differences or stochastic effects. To circumvent this issue, embodiments of the present invention provide a primer design methodology that essentially removes the intra-specific locus competition that occurs in heterozygotes (see Anderson, et al., referenced supra). This design involves utilization of the direct repeat units that flank an Alu element. The Alu and flanking direct repeat sequence make for a completely unique genomic site. There are hundreds of polymorphic Alu's that contain direct repeats (Excoffier, L., et al., *Arlequin (version 3.0): an integrated software package for population genetics data analysis*, Evolutionary Bioinformatics Online, 1: 47 (2005)). The reverse primers for filled site reactions may contain some 5' Alu sequence, the direct repeat unit and some flanking genomic sequence extending beyond the direct repeat unit. Reverse primers for empty site reactions may contain the pre-integration site and flanking genomic sequence of both sides such that the length of the oligo traverses flanking genomic sequence 5' and 3' to the pre-integration site. The 5' end of the empty site reverse primer may contain only one or two base pairs of genomic sequence beyond the pre-integration site.

FIG. 3 demonstrates the improved "mini-primer" design methodology that has been adopted in order to detect individual Alu loci. This design results in the elimination of intra-locus specific competition which reduces the potential for allele-drop out that is common in STR-based systems, especially when trace amounts of template DNA are used. Using this primer design methodology may also result in the ability to amplify nuclear DNA in a single cut/shed hair sample. Once the target site products have been amplified, they can be detected using a standard capillary electrophoresis system (Applied Biosystems 310 or 3130) or micro fluidic based capillary electrophoresis systems.

The design of the primers of embodiments of the present invention, described herein and referred to subsequently as mini-primers, reduces the overall amplicon size as well as the difference in amplicon sizes between the two allelic states of INNULs. Amplification of the two alleles may occur through a common fluorescently-labeled forward primer and two unlabeled reverse primers. The labeled forward primer for the null allele may overlap the insertion site of the RE, and the unlabeled reverse primer for the insertion allele may have an overlap region with the junction and the RE itself, or just inside the RE. With this design the resulting INNUL allelic amplicons may be designed to differ by as little as one base pair. Additionally, the amplicon size can be reduced substantially, to a size much smaller than currently used STR markers, such that substantially degraded samples can be typed. With this design a more simplified and automated typing technology can be applied for LINE and SINE typing.

Selection criteria for INNUL markers to include in a multiplex depend on the application. Markers that are highly polymorphic in all major populations (i.e., approaching 50% heterozygosity) are desirable for human identity testing (LaFountain, M. J., et al., *TWGDAM Validation of the AmpFeSTR Profiler Plus and AmpFeSTR COfiler STR Multiplex Systems Using Capillary Electrophoresis*, Journal of Forensic Sciences, 46(5): 1191-1198 (2001); Moretti, T., et al., *Validation of short tandem repeats (STRs) for forensic usage: performance testing of fluorescent multiplex STR systems and analysis of authentic and simulated forensic samples*, Journal of Forensic Sciences, 46(3): 647 (2001); Budowle, B., *SNP typing strategies*. Forensic Science International, 146: S139 (2004); Syvanen, A. C., et al., referenced supra; LaRue, B. L., et al., referenced supra) while those demonstrating high coefficients of inbreeding (e.g., single nucleotide polymorphisms (SNPs) in which the different allelic states approach fixation in different populations) can be used for bio-ancestry analyses (see Shriver, M. D., et al., referenced supra). To demonstrate the potential of the newly designed primer sets for human identity testing that would support high quality DNA typing applications, such as in paternity testing, and low quality samples that may be encountered in criminal forensic casework, an initial set of INNUL markers based on Alu's and LINEs were chosen. The Alu based INNUL markers were selected based on molecular characteristics and extant population data (Wang, J., et al., *dbRIP: A highly integrated database of retrotransposon insertion polymorphisms in humans*, Human Mutation, 27(4): 323-329 (2006); Benson, D. A., et al., referenced supra; Cheung, K. H., et al., *ALFRED: an allele frequency database for diverse populations and DNA polymorphisms*, Nucleic Acids Research, 28(1): 361 (2000)). There was no available population data on LINE based INNUL markers, so only molecular characteristics were used as selection criteria for this study.

The ability of the patented inventive primer design to analyze heavily degraded and fragmented DNA samples is a substantial improvement over the prior art, as current forensic technologies such as mini-STR kits often give inconclusive results on such samples. In order to assess the potential of these new markers for forensic use, three fluorescently labeled markers were tested on mechanically and enzymatically degraded DNA samples. In theory, the primers designed based on the mini-primer design strategy should yield useful results on these samples even though they are degraded. Because the system relies upon the uniqueness of the repeat unit sequence in the flanking region of Alu and other Retrotransposon insertion sites, it requires only a small amplicon length, <100 bp, to give conclusive results.

For forensic casework applications, it is an absolute requirement that the primers selected can be multiplexed into a single amplification reaction. Forensic casework samples are often in very low quantity as well as being degraded. A suitable multiplexed system should be able to amplify multiple target sequences at the same time with no non-specific amplification product and also have the sensitivity to amplify DNA concentration as low as 100 pg or less. The most challenging technical task in multiplexing various markers is to co-amplify, in a single amplification, a plurality of markers with the same high sensitivity and specificity as is obtained when each marker is amplified individually. The number of markers needed within a useful system depends on the statistically calculated power of discrimination of the resulting reagent kit. Several multiplex systems containing as many as 32 markers are currently in commercial use (LaRue, B. L., et al., referenced supra). There are several published reports with guidance for achieving a successful PCR multiplex (Markoulatos, P., et al., *Multiplex Polymerase Chain Reaction: A Practical Approach*, Journal of Clinical Laboratory Analysis 16: 47-51 (2002); Schoske, R., et al., *Multiplex PCR Design Strategy Used for the Simultaneous Amplification of 10 Y Chromosome Short Tandem Repeat (STR) Loci*, Analytical & Bioanalytical Chemistry 375: 333-343 (2003); O. Henegariu, et al, *Multiplex PCR: Critical Parameters and Step-by-Step Protocol*, BioTechniques 23: 504-511 (1997); Shuber, A. P., et al., *A Simplified Procedure for Developing Multiplex PCRs*, Genome Research 5: 488-493 (1995)). The parameters to consider for developing a multiplexed PCR system are: primer length and sequence, melting temperature of each primer, relative concentration of primers, concentration of PCR buffer, balance between magnesium chloride and dNTP concentration, cycling temperatures and times, concentration of Taq DNA polymerase, and the addition of PCR modifiers. The optimization of each step for target DNA amplification is essential in order to achieve a multiplexed amplification with specificity and high sensitivity. One embodiment of the present invention, the creation of a four-dye multiplex for forensic applications, is described below.

The description herein, including the Examples below, demonstrates that by utilizing the Mini-Primer strategy, INNUL markers, which include SINEs, LINEs, and SVAs, can be effectively used as markers for human identification and bio-ancestry studies regardless of the size of the inserted element. The size of the amplicons for INNULs and the difference between allelic states can be reduced substantially such that these markers have utility for analyzing high and low quality human DNA samples. In addition, the preliminary results demonstrate that sensitivity of detection can be sufficient to enable human identity and bio-ancestry studies on forensic and anthropological samples. Depending on the markers selected and the distribution of the alleles in global populations, INNULs can be selected for human identity testing or for bio-ancestry studies.

The description herein, together with the Examples below, also demonstrates the optimization of INNUL markers into a single-tube, multi-locus reaction. The inclusion of these markers in a multiplexed reaction produces an INNUL-based human identity test set that is a powerful tool for use in many forensic settings without the need for investment in new instrumentation. The multiplexed system is able to amplify multiple target sequences at the same time with minimal non-specific amplification products and also exhibits the sensitivity to amplify DNA concentrations as low as 100 pg or less. With an amplicon size range of 56-125 base pairs, this multiplexed system contains the smallest size amplicons that are both amenable for use with extensively degraded DNA samples and generally available for use by the forensic community. Thus, the INNUL multiplex systems presented in this study provide a statistically discriminating tool that is useful for forensic applications where the sample is limited in quantity as well as quality.

While this invention is particularly shown and described with reference to the embodiments described in the Examples below, those skilled in the art will recognize that other embodiments are possible without departing from the spirit and scope of the present description. For example, the PCR amplification products of the methods and systems described herein may be characterized using Next Generation Sequence analysis (NGS) analysis methods (Mak, H. C., *Next-Generation Sequence Analysis*, Nature Biotechnology 29: 45-46 (2011); Metzker, M. L., *Sequencing Technologies—The Next Generation*, Nature Reviews/Genetics 11: 31-46 (2010)). Additional embodiments of the invention may make use of rapid DNA analysis platforms (see, e.g., Khandurina, et al., Integrated System for Rapid PCR-Based DNA Analysis in Microfluidic Devices, Analytical Chemistry 72: 2995-3000 (2000)) for characterization of the PCR amplification products of the methods and systems of the invention. In other embodiments, practitioners may find that labeling the reverse primers instead of labeling the forward primers is more effective for a particular purpose.

EXAMPLES

Example 1

A Four Dye Multiplex System for Forensic Applications

A number of markers were selected for multiplexing for a forensically useful kit. The forward primers for each marker were labeled with one of four fluorophores, 6-carboxyfluorescein (6-FAM), 4,5-dichloro-dimethoxy-fluorescein (JOE), carboxytetramethylrhodamine (TAMRA), or 5-carboxy-Xrhodamine (ROX) and a fifth fluorophore in the orange wavelength as the size standard). The selected markers' amplicons range in size between approximately 56 and 125 bp, and individual INNUL alleles differ in amplicon size between 3 and 10 bps. The gender marker Amelogenin was also added to the multiplex. Multiplex optimization experiments addressing primer concentration and peak heights were performed.

Markers were selected from dbRIP.org, existing literature, and through BLAST sequence analysis (A F. A. Smit, et al.; Batzer, M. A., et al. (2002); Batzer, M. A. et al. (1994); Feng, q., et al.; Houck, C. M., et al.; Kazazian, H. H., et al.; Ostertag, E. M., et al.; Ustyugova, S. V., et al.; Mamedov, I. Z., et al.; Novick, G. E., et al.; Wang, J., et al. (2006), all referenced supra; McGinnis, S., et al., BLAST: at the core of a powerful and diverse set of sequence analysis tools, Nucleic Acids Research, 32(suppl 2): W20-W25 (2004)). After initial selection, the potential loci were assessed for their suitability for primer design (Zangenberg, G., et al., referenced supra).

Genomic DNA was extracted from human buccal swabs using ChargeSwitch® gDNA Buccal Cell Kit (Invitrogen) via magnetic bead separation. All extractions were run with a reagent blank. Samples were stored at −20° C. until amplification.

Extracted samples were quantified using the Quantifiler® Human Quantification Kit (Applied Biosystems) or the InnoQuant™ Human DNA Quantification & Degradation Assessment Kit and performed on the 7500 Real-Time PCR System (Applied Biosystems). The cycle conditions were based upon the Quantifiler™ Kit or InnoQuant™ Kit User's Manual (Applied Biosystems, 2010). The data was analyzed using the HID Real-Time PCR Analysis Software v1.1 (Applied Biosystems) with a threshold value set per the manufacturer recommendations.

Example 2

Primer Design

Primers were designed using Primer3 (Untergrasser A., et al., "Primer3—New Capabilities and Interfaces," Nucleic Acids Research 40(15): e115 (2012); Koressaar T., et al., "Enhancements and Modifications of Primer Design Program Primer3," Bioinformatics 23(10): 1289-91 (2007); input version 0.4.0; frodo.wi.mit.edu/primer3/). A set of three primers was designed for each marker: one forward primer and two reverse primers, one for the insertion and one for the null allele. All of the designed primers have Tm values in the ranges of 58°-63° C. The program "Reverse Complement" from the Harvard Medical Technology Group and Lipper Center for Computational Genomics was used (arep.med.harvard.edu/labgc/adnan/projects/Utilities/revcomp.html). Subsequently, the primers were screened against the GenBank non-redundant database (National Center for Biotechnology Information, U.S. National Library of Medicine, National Institutes of Health) to determine whether they were unique DNA sequences. Table 1 provides the selected markers, and Table 2 provides the primer sequences used for the selected markers.

TABLE 1

Selected retrotransposable element (RE) markers.

| | Selected Marker | Chromosome | Type | Reverse Empty (bp) | Reverse Filled (bp) | Location | Band | Gene ID |
|---|---|---|---|---|---|---|---|---|
| 1 | CH1-6217 | 1 | LINE | 160 | 157 | chr1: 219894446-219894446 | 1q41 | chr1-2182; 1104685475315; RIP_L1_chr1_218_01 |
| 2 | pAlu1-2767 | 1 | Alu | 101 | 101 | chr1: 26362411-26362722 | 1p36.11 | pAlu1-25722767; RIP_Alu_chr1_026_01 |
| 3 | TARBP1*‡ | 1 | Alu | 75 | 71 | chr1: 234,527,060-234,614,849 | 1q42.2 | AL136124.10; 3310_33420Sdel |
| 4 | Ya5-MLS48* | 2 | Alu | 87 | 81 | chr 2: 74,024,900-74,034,900 | 2p13.1 | AC073577.32; 48284_48612del |
| 5 | Yb8AC1141*‡ | 3 | Alu | 67 | 62 | chr3: 96598900-96599212 | 3q11.2 | pAlu3-96397335; RIP_Alu_chr3_096_01 |
| 6 | LC3-2601 | 3 | LINE | 178 | 127 | chr3: 26414512-26420540 | 3p24.1 | 238595; L1HS364; RIP_L1_chr3_026_01 |
| 7 | Ya5NBC51*‡ | 3 | Alu | 121 | 125 | chr3: 191773344-191773631 | 3q28 | Ya5NBC345; RIP_Alu_chr3_191_01 |
| 8 | HS4.69*‡ (NC000005.10) | 5 | Alu | 115 | 110 | chr5: 164366293-164366709 | 5q34 | NT_023133 |
| 9 | CH26240 | 5 | LINE | 153 | 132 | chr5: 151436625-151442640 | 5q33.1 | L1HS446; Druze75; RIP_L1_chr5_I51_01 |
| 10 | YA5NBC327 | 6 | Alu | 131 | 127 | chr6: 50560439-50560754 | 6p12.3 | RIP_Alu_chr6_050_01 |
| 11 | CH6-28-9163 | 6 | LINE | 112 | 115 | chr6: 19873106-19879163 | 6p22.3 | AL022726; RIP_L1_chr6_019_01; AC206603 |
| 12 | Ya5ACA1736* | 8 | Alu | 112 | 109 | chr8: 126093295-126093295 | 8q24.13 | pAlu8-125692903; RIP_Alu_chr8_I26_01 |

TABLE 1-continued

Selected retrotransposable element (RE) markers.

| | Selected Marker | Chromosome | Type | Reverse Empty (bp) | Reverse Filled (bp) | Location | Band | Gene ID |
|---|---|---|---|---|---|---|---|---|
| 13 | Ya5NBC239 | 9 | Alu | 69 | 65 | chr9: 118516900-118517218 | 9q33.1 | RIP_Alu_chr9_I16_01 |
| 14 | Yb7AD155 | 10 | Alu | 102 | 101 | chr10: 10493725-10493824 | 10q21.1 | gi|224514932|rel|NT_008705.16 |
| 15 | Ya5-MLS18* | 11 | Alu | 79 | 76 | chr11: 24749534-24749534 | 11p14.3 | RIP_Alu_chr11_024_01 |
| 16 | CH4-12-7012 | 12 | LINE | 150 | 122 | chr4: 20769969-20775752 | 4p15.31 | L1HS39; RIP_L1_chr4_016_01 |
| 17 | Ya5ac2305‡ | 13 | Alu | 94 | 93 | chr13: 38926483-38926791 | 13q13.3 | RIP_Alu_chr13_038_01 |
| 18 | Ya5ac2265*‡ | 13 | Alu | 102 | 98 | chr13: 102807866-102808174 | 13q33.1 | pAlu13-102846400; 79718; RIP_Alu_chr13_102_01 |
| 19 | Ya5NBC241* | 15 | Alu | 104 | 103 | chr15: 41447735-41448045 | 15q15.3 | 238740; RIP_Alu_chr15_041_01 |
| 20 | Yb8NBC13*‡ | 16 | Alu | 91 | 89 | chr16: 26515540-26515866 | 16p12.1 | pAlu16-26535378; RIP_Alu_chr16_026_02 |
| 21 | Yb8AC1796 | 18 | Alu | 100 | 100 | chr18: 42592433-42592753 | 18q21.1 | RIP_Alu_chr18_042_01 |
| 22 | CHR20-79712*‡ | 20 | LINE | 97 | 93 | chr20: 11465280-11465588 | 20p12.2 | 79712; RIP_Alu_chr20_011_01 |
| 23 | Yb8NBC106*‡ | 21 | Alu | 120 | 115 | chr21: 40508751-40509060 | 21q22.2 | RIP_Alu_chr21_040_01 |
| 24 | Ch22-Ya5533 | 22 | LINE | 112 | 115 | chr22: 14733466-14733466 | 22q11.1 | Ya5533; RIP_Alu_chr22_014_01 |
| 25 | Ya5-MLS09*‡ | 1 | Alu | 119 | 113 | chr1: 179124190-179124190 | 1q25.3 | AK023131.1, 1453_1773del |
| 26 | Ya5-MLS26‡ | 3 | Alu | 83 | 81 | chr3: 40216628-40216628 | 3p22.1 | AY736289; 157_483del |
| 27 | AC4027‡ | 7 | Alu | 70 | 67 | chr7: 82559246-82559572 (bg16/Human) | 7q21.11 | AC004027.1; 997_1332del |
| 28 | SVA306 | 14 | SVA | 71 | 74 | chr14: 64430151-64433293 | 14q23.3 | SPTB; H14_E_66; RIP_SVA_chr14_064_01; dbRP ID: 3000006 |
| 29 | SVA323 | 3 | SVA | 120 | 117 | chr3: 195602463-195603210 | 3q29 | AFURS1; RIP_SVA_chr3_195_01; dbRIP ID: 3000023 |
| 30 | Yc1RG148‡ | 2 | Alu | 82 | 75 | chr2: 150467557-150467867 | 2q23.3 | Yc1RG148; RIP_Alu_chr2_I50_03 |
| 31 | Yb9NBC10‡ | 4 | Alu | 89 | 83 | chr4: 144792753-144793064 | 4q31.21 | Yb9NBC10; RIP_Alu_chr4_144_01 |
| 32 | Ya5NBC216‡ | 7 | Alu | 110 | 101 | chr7: 3847999-38475312 | 7q14.1 | Ya5NBC216; 4601; Ya5505; RIP_Alu_chr7_038_01 |
| 33 | Ya5ACA1766*‡ | 8 | Alu | 68 | 63 | chr8: 61367553-61367857 | 8q12.1 | Ya5ACA1766; RIP_Alu_chr8_061_01 |
| 34 | Yb8NBC148‡ | 14 | Alu | 116 | 114 | chr14: 80666808-80667112 | 14q31.1 | YbSNBC148; RIP_Alu_chr14_080_02 |
| 35 | Ya5NBC102‡ | 17 | Alu | 95 | 99 | chr17: 58919634-58919634 | 17q23.3 | Ya5NBC102; Ya5ACE; RIP_Alu_chr17_058_01 |
| 36 | SB19.12‡ | 19 | Alu | 111 | 106 | chr19: 61803374-61803676 | 19q13.43 | Sb19.12; RIP_Alu_chr19_061_01 |
| 37 | Yb8NBC120‡ | 22 | Alu | 80 | 75 | chr22: 16427377-16427718 | 22q11.21 | Yb8NBC120; RIP_Alu_chr22_016_04 |
| 38 | CH1-2250* pAlu1-27480751|238884 | 1 | ALU | 105 | 102 | chr1: 27931950-27932250 | 1p35.3 | Yb8SINE; RIP_Alu_chr1_027_02 |
| 39 | Yb8AC1197 | 3 | ALU | 104 | 105 | chr3: 123621143-123621458 | 3q21.1 | Yb8SINE RIP_Alu_chr3_123_01 |
| 40 | Yb8AC1439 | 8 | ALU | 154 | 159 | chr8: 138978354-138978557 | 8q24.23 | Yb8AC1439; RIP_Alu_chr8_138_01 |
| 41 | Yb8NBC69 | 7 | ALU | 134 | 126 | chr7: 95905459-95905763 | 7q21.3 | Yb8NBC69; RIP_Alu_chr7_095_02 |
| 42 | Yb8NBC126 | 2 | ALU | 178 | 177 | chr2: 114079139-114079440 | 2q14.1 | Yb8NBC126; RIP_Alu_chr2_114_01 |
| 43 | Yb8NBC622 | 11 | ALU | 118 | 118 | chr11: 6837937-6838542 | 11p15.4 | Yb8NBC622; RIP_Alu_chr11_006_01 |
| 44 | Ya5ACA1153 | 4 | ALU | 169 | 168 | chr4: 181786436-181786736 | 4q34.3 | pAlu4-182133785; Ya5ACA1153; RIP_Alu_chr4_I81_01 |
| 45 | YbSNBC18 | 21 | ALU | 132 | 131 | chr21: 9991029-9991309 | 21p11.2 | Yb8NBC18; RIP_Alu_chr21_009_01 |
| 46 | Yb8NBC67 | 6 | ALU | 137 | 147 | chr6: 25637865-25637990 | 6p22.2 | Yb8NBC67; 7451; RIP_Alu_chr6_025_01 |
| 47 | Yb8NBC237 | 7 | ALU | 106 | 98 | chr7: 8716802-8717116 | 7p21.3 | Yb8NBC237; RIP_Alu_chr7_008_01 |
| 48 | Yc1NBC60 | 10 | ALU | 111 | 103 | chr10: 00748551-10748858 | 10p14 | Yc1NBC60; RIP_Alu_chr10_010_01 |
| 49 | Ya5NBC157 | 17 | ALU | 156 | 155 | chr17: 58095057-58095351 | 17q23.2 | Ya5NBC157; RIP_Alu_chr17_058_02 |
| 50 | HS4.75 | 3 | ALU | 110 | 109 | chr3: 176098317-176098628 | 3q26.31 | Ya5HS4.75; RIP_Alu_chr3_176_01 |
| 51 | pAlu1-90961213 | 1 | ALU | 124 | 129 | chr1: 91397377-91397644 | 1p22.2 | pAlu1-90961213; RIP_Alu_chr1_091_01 |
| 52 | Ya5ACA912 | 2 | ALU | 100 | 102 | chr2: 41796105-41796419 | 2p21 | Ya5ACA912; RIP_Alu_chr2_041_01 |

TABLE 1-continued

Selected retrotransposable element (RE) markers.

| | Selected Marker | Chromosome | Type | Reverse Empty (bp) | Reverse Filled (bp) | Location | Band | Gene ID |
|---|---|---|---|---|---|---|---|---|
| 53 | Yc1RG148 | 2 | ALU | 91 | 76 | chr2: 150467557-150467867 | 2q23.3 | Yc1RG148; RIP__Alu__chr2__150__03 |
| 54 | Ya5-NBC171 | 6 | ALU | 99 | 97 | chr6: 62111955-62112258 | 6q11.1 | Ya5NBC171; RIP__Alu__chr6__062__01 |
| 55 | Ya5NBC212 | 7 | ALU | 71 | 60 | chr7: 93796281-93796580 | 7q21.3 | Ya5NBC212; RIP__Alu__chr7__093__01 |
| 56 | Ya5NBC54 | 6 | ALU | 88 | 90 | chr6: 108372816-108373108 | 6q21 | pAlu6-108266151; Ya5NBC54; 31139; RIP__Alu__chr6__108__01 |
| 57 | Ya5NBC335 | 20 | ALU | 63 | 62 | chr20: 24217612-24217829 | 20p11.21 | Ya5NBC335; RIP__Alu__chr20__024__01 |
| 58 | Ya5-MLS37 | 10 | ALU | 68 | 69 | chr10: 85973241-85973241 | 10q23.1 | Ya5-MLS37; RIP__Alu__chr10__085__03 |
| 59 | Ya5ACA1549 | 6 | ALU | 65 | 63 | chr6: 65241885-65242187 | 6q12 | Ya5ACA1549; RIP__Alu__chr6__065__01 |
| 60 | Ya5-MLS04 | 5 | ALU | 66 | 64 | chr5: 91516545-91516886 | 5q14.3 | Ya5-MLS04; RIP__Alu__chr5__091__01 |
| 61 | Yb8NBC225 | 12 | ALU | 85 | 79 | chr12: 125471071-125471368 | 12q24.32 | Yb8NBC225; 2166; RIP__Alu__chr12__125__01 |

*Selected for multiplex including 15 markers plus amelogenin (see Example 6)
‡Selected for multiplex including 20 markers plus amelogenin (see Example 7)

TABLE 2

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| CH1-6217 | [JOE]TGGCCCACCTATG TCTAAAA SEQ ID NO: 1 TGGCCCACCTATGTCT AAAA SEQ ID NO: 2 | GTTGATTCAAAGCAA CCAATCC SEQ ID NO: 3 | GTCAAGGCAAACCA ATCCAA SEQ ID NO: 4 | 81 | 77 |
| pAlu1-2767 | [Label]TGTACTTGGGAG CTCAGAGCAG SEQ ID NO: 5 TGTACTTGGGAGCTCA GAGCAG SEQ ID NO: 6 | [FAM]TGCTCnCCTTC TTCCTTCT SEQ ID NO: 7 TGCTCTTCCTTCTTCC TTCT SEQ ID NO: 8 | [JOE]TTCCGGCCCCC TTCTTCCTT SEQ ID NO: 9 TTCCGGCCCCCTTCT TCCT SEQ ID NO: 10 | 101 | 103 |
| TARBP1 | [TMR]CCAAAGTTTACT ATAAGGAGGCAAA SEQ ID NO: 11 CCAAAGTTTACTATAA GGAGGCAAA SEQ ID NO: 12 | TGATCCAGTCATTCAT CATTTTAT SEQ ID NO: 13 | CGGCCCATTCATCA GTTT SEQ ID NO: 14 | 75 | 71 |
| TARBP1 | [Label]AAGGAGGCAAA GGAAGAATACA SEQ ID NO: 15 AAGGAGGCAAAGGAA GAATACA SEQ ID NO: 16 | GTTGATCCAGTCATTC ATCATTTTAT SEQ ID NO: 17 | GCGGCCCATTCATC AGTTT SEQ ID NO: 18 | 65 | 60 |
| Ya5-MLS48 | [6~FAM]TGGCTTGTAA ACTAATTGCTG SEQ ID NO: 19 TTGGCTTGTAAACTAA TTGCTG SEQ ID NO: 20 | GCAAAGCAACTTGCA CCTTTTCTA SEQ ID NO: 21 | GCGGCCGCACCTTT TCTATTG SEQ ID NO: 22 | 87 | 81 |

TABLE 2-continued

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| Yb8AC1141 | [TMR]TACAAATACTAC AGACAAAAGCTACTGA SEQ ID NO: 23 TACAAATACTACAGAC AAAGCTACTGA SEQ ID NO: 24 | GAGAACCCCACCAAC CTGACT SEQ ID NO: 25 | CCGGCCCAACCTGA CTTA SEQ ID NO: 26 | 67 | 62 |
| Yb8AC1141 | [ROX]ACAAATACTACA GACAAAAGCTACTGA SEQ ID NO: 27 ACAAATACTACAGACA AAAGCTACTGA SEQ ID NO: 28 | GAACCCCACCAACCT GACT SEQ ID NO: 29 | GGCCCAACCTGACT TACT SEQ ID NO: 30 | 66 | 59 |
| LC3-2601 | [Label]TTGGCCATAGAA AAACCAGTC SEQ ID NO: 31 TTGGCCATAGAAAAAC CAGTC SEQ ID NO: 32 | [FAM]AGAATCAGAAT GGGGTCTT SEQ ID NO: 33 AGAATCAGAATGGGG TCTT SEQ ID NO: 34 | [JOE]ATCTTGGCTCC TCCGTTTGT SEQ ID NO: 35 ATCTTGGCTCCTCC GTTTGT SEQ ID NO: 36 | 176 | 125 |
| Ya5NBC51 | [TMR]TCGCCATCTCTTC TTCCTTCA SEQ ID NO: 37 TCGCCATCTCTTCTTCC TTCA SEQ ID NO: 38 | GTCCAGGGTTAATGC TTTGTT SEQ ID NO: 39 | TTACAGGCGTGAGA ATGCTT SEQ ID NO: 40 | 121 | 125 |
| Ya5NB | [ROX]TCGCCATCTCTTC TTCCTTCA SEQ ID NO: 41 | GTCCAGGGTTAATGC TTTGT SEQ ID NO: 42 | GTCCAGGGTTAATG CTTTGT SEQ ID NO: 43 | 122 | 124 |
| HS4.69 | [TMR]TGCCAGGTGATA GTATTAGGAGGTG SEQ ID NO: 44 TGCCAGGTGATAGTAT TACGAGGTG SEQ ID NO: 45 | GCTAGCTAACTCTCTA AGGTC SEQ ID NO: 46 | CCGGCCTCTAAGGT CTTTTT SEQ ID NO: 47 | 115 | 110 |
| HS4.69 | [ROX]TGCCAGGTGATA GTATTAGGAGGTG SEQ ID NO: 48 | GGCATCGTATCTATTC ATGTGATTTTTA SEQ ID NO: 49 | CCGGCCTATTCATG TGATTT SEQ ID NO: 50 | 81 | 77 |
| Ya5ACA1736 | [FAM]CCTGCTCTGCAC ACTTCTTG SEQ ID NO: 51 CCTGCTCTGCACACTTC TTG SEQ ID NO: 52 | GACCTTGACCTAGAG AAGGCAAT SEQ ID NO: 53 | GCCGAGAAGGCAAT TTTCTA SEQ ID NO: 54 | 109 | 100 |
| CH26240 | [Label]TGGTGACAGAGT GAGACCTTG SEQ ID NO: 55 TGGTGACAGAGTGAGA CCTTG SEQ ID NO: 56 | [FAM]TGACTCATGTA ACTTGTCTGCTTG SEQ ID NO: 57 TGACTCATGTAACTTG TCTGCTTG SEQ ID NO: 58 | [JOE]TGTTGGACATT TGCATACCC SEQ ID NO: 59 TGTTGGACATTTGC ATACCC SEQ ID NO: 60 | 153 | 132 |
| Ya5NBC327 | [Label]TGTCATGTACAA ACAGGGATAGTT SEQ ID NO: 61 TGTCATGTACAAACAG GGATAGTT SEQ ID NO: 62 | GCGCCCGGCCCTCAT TATTC SEQ ID NO: 63 | CAAGGATACCCATT CTCATTATTCTTA SEQ ID NO: 64 | 127 | 131 |
| CH6-28-9163 | [FAM]TGGCTGTGGTGG AGGATAA SEQ ID NO: 65 TGGCTGTGGTGGAGGA TAA SEQ ID NO: 66 | GCACATGCCACCATA CCCAG SEQ ID NO: 67 | GOCATCTTGGCTCC AGTTAGTT SEQ ID NO: 68 | 116 | 112 |

TABLE 2-continued

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| Ya5NBC239 | [FAM]TTCCTGCTATGA GCCACGTA SEQ ID NO: 69 TTCCTGCTATGAGCCA CGTA SEQ ID NO: 70 | CATTTAGATCTCACAT GATTCTTATGC SEQ ID NO: 71 | CCGGCCTCACATGA TTCTTA SEQ ID NO: 72 | 69 | 65 |
| Yb7AD155 | [ROX]TGTACACATTAA GCACATGGAAGTCA SEQ ID NO: 73 TGTACACATTAAGCAC ATGGAAGTCA SEQ ID NO: 74 | GCATGAAATGTTCTTT TTCATCT SEQ ID NO: 75 | GCCCGGCCGTTCTT TTTC SEQ ID NO: 76 | 102 | 101 |
| Ya5-MLS18 | [ROX]AACTTCAAGGTA TTTGCATCATG SEQ ID NO: 77 AACTTCAAGGTATTTG CATCATG SEQ ID NO: 78 | TGCTAGCTAACTCTCT AAGGTCTT SEQ ID NO: 79 | CCGGCCTCTAAGGT CTTTTT SEQ ID NO: 80 | 79 | 76 |
| Ya5-MLS18 | [JOE]AACTTCAAGGTAT TTGCATCATG SEQ ID NO: 81 | GGCATCGTATCTATTC ATGTGATTTTA SEQ ID NO: 82 | CCGGCCTATTCATG TGATTT SEQ ID NO. 83 | 73 | 70 |
| CH4-12-7012 L1HS39 | [Label]GGAAAGGTACA AGATGTAATGAGGA SEQ ID NO: 84 GGAAAGGTACAAGATG TAATGAGGA SEQ ID NO: 85 | [FAM]TTGCCCACACC TTGATCTTGA SEQ ID NO: 86 TTGCCCACACCTTGAT CTTGA SEQ ID NO: 87 | [JOE]CGGAGGAAAA TGGCCAAGACAA SEQ ID NO: 88 CGOAGGAAAATGGC CAAGACAA SEQ ID NO: 89 | 152 | 125 |
| Ya5ac2305 | [TMR]TTTAAAATACAA TCCAACACCATTT SEQ ID NO: 90 TTTAAAATACAATCCA ACACCATTT SEQ ID NO: 91 | GGCATCCTTTGATTAC AACTCTTA SEQ ID NO: 92 | GGCCCAATTACAA CTCT SEQ ID NO: 93 | 94 | 93 |
| Ya5ac2305 | [JOE]GGTGACACTCCA ATTTCTTCT SEQ ID NO: 94 TGGTGACACTCCAATT TCTTCT SEQ ID NO: 95 | | GCCCCAATTACAAC TCTTAAGGAAA SEQ ID NO: 96 | 52 | 49 |
| Ya5AC2265 | [JOE]AGAAGAGTGAAT GCACATTTATGA SEQ ID NO: 97 AGAAGAGTGAATGCAC ATTTATGA SEQ ID NO: 98 | GGAGTCATGAATTCA GTTTCTTA SEQ ID NO: 99 | GCCCGGCCCAGTTT CTTA SEQ ID NO: 100 | 102 | 98 |
| Ya5NBC241 | [TMR]TTTAGTTCCCCA CAATTAACATGA SEQ ID NO: 101 TTTAGTTCCCCACAATT AACATGA SEQ ID NO: 102 | GCTTTCCCCCAGAAG ATCCAT SEQ ID NO: 103 | GCCGGCCAAGATCC ATTCT SEQ ID NO: 104 | 98 | 93 |
| YB8NBC13 | [JOE]TCTGGCAAATGCTA CCCAAGT SEQ ID NO: 105 CTGGCAAATGCTACCC AAGT SEQ ID NO: 106 | GCATCTTCCTCTTCAC ATCTTAT SEQ ID NO: 107 | GGCCCCTCTTCACA TCT SEQ ID NO: 108 | 91 | 89 |
| Yb8NBC13 | [FAM]CTGGCAAATGCT ACCCAAGT SEQ ID NO: 109 | GCTGAAGCATCTTCCT CTTCACA SEQ ID NO: 110 | GCGGCCCCTCTTCA CATCTTA SEQ ID NO: 111 | 96 | 91 |

TABLE 2-continued

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| Yb8NDC13 | [JOE]TCTGGCAAATGCT ACCCAAGT SEQ ID NO: 112 TCTGGCAAATGCTACC CAAGT SEQ ID NO: 113 | GGCATCTTCCTCTTCA CATCTTAT SEQ ID NO: 114 | GGCCCCTCTTCACA TCTTATC SEQ ID NO: 115 | 87 | 91 |
| CHR20-79712 | [FAM]CTGGACCTCTCC ATCCCTAT SEQ ID NO: 116 CTGGACCTCTCCATCCC TAT SEQ ID NO: 117 | AGTTTGCACGTAAGA CAGAATTT SEQ ID NO: 118 | CCGGCCAAGACAGA ATTT SEQ ID NO: 119 | 97 | 93 |
| CHR20-79712 | [FAM]ATTTGCACAGTG CTCCACAC SEQ ID NO: 120 ATTTGCACAGTGCTCC ACAC SEQ ID NO: 121 | GTTGCACGTAAGACA GAATTTGA SEQ ID NO: 122 | GCGGCCAAGACAG AATTTGA SEQ ID NO: 123 | 55 | 53 |
| CHR20-79712 | | GTTTTGCACGTAAGA CAGAATTTGA SEQ ID NO: 124 | GCGGCCAAGACAG AATTT SEQ ID NO: 125 | 57 | 52 |
| Yb8AC1796 | [JOE]TGCCAGACAGCA AACAAATA SEQ ID NO: 126 TGCCAGACAGCAAACA AATA SEQ ID NO: 127 | GCAAGGTCACAGGTA GGCTTTTTA SEQ ID NO: 128 | GGCCACAGGTAGGC TTTTTA SEQ ID NO: 129 | 95 | 90 |
| Yb8NBC106 | [FAM]CATCAAACTCCA GAGTTCCTAAG SEQ ID NO: 130 CATCAAACTCCAGAGT TCCTAAG SEQ ID NO: 131 | GATTGATGAGGACTC AGGTTGA SEQ ID NO: 132 | GGATTACAGGCGTG AGGATT SEQ ID NO: 133 | 120 | 115 |
| Ya5-MLS09 | [JOE]AGCAGATTTCAGG TCATTATTGTTT SEQ ID NO: 134 AGCAGATTTCAGGTCA TTATTGTTT SEQ ID NO: 135 | TTTCTCTCAGAGCTAT CTCAATTTTAA SEQ ID NO: 136 | CGGCCTGCTATCTC AATTT SEQ ID NO: 137 | 119 | 113 |
| Ya5-MLS09 | | GTTTCTCTCAGAAGCT ATCTCAATTTTAA SEQ ID NO: 138 | GCGGCCTGCTATCT CAATTT SEQ ID NO: 139 | 118 | 112 |
| Ch22-Ya5533 | [FAM]AGAGAAAAACA AACATGTAAACTGCT SEQ ID NO: 140 AGAGAAAAACAAACAT GTAAACTGCT SEQ ID NO: 141 | CGGTCTTGTAAATCTT AATTTGTTG SEQ ID NO: 142 | AAAGTGCTGGGTAA ATCTTAATTTG SEQ ID NO: 143 | 112 | 115 |
| AC4027 | [FAM]AAGGTCTAAGCG CAGTGGAA SEQ ID NO: 144 AAGGTCTAAGCGCAGT GGAA SEQ ID NO: 145 | TGTGTTTTGTACAGAG TTCTTAATTGC SEQ ID NO: 146 | CCGGCCCAGAGTTC TTAA SEQ ID NO: 147 | 70 | 67 |
| AC4027 | [JOE]AAGGTCTAAGCG CAGTGGAA SEQ ID NO: 148 | GTGTTTTGTACAGAGT TCTTAATTGC SEQ ID NO: 149 | GGCCCAGAGTTCTT AATTGC SEQ ID NO: 150 | | 64 |

TABLE 2-continued

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| Amelogenin | [TMR]CCCTTTGAAGTGGTACCAGAGCA SEQ ID NO: 151 CCCTTTGAAGTGGTACCAGAGCA SEQ ID NO: 152 | GCATGCCTAATATTTTCAGGGAATA SEQ ID NO: 153 | . | X = 79 | Y = 81 |
| Amelogenin | [Label]CCCTTTGAAGTGGTACCAG SEQ ID NO: 154 CCCTTTGAAGTGGTACCAG SEQ ID NO: 155 | | | | |
| Yc1RG148 | [JOE]AACACGTTCTGAAACATCCATC SEQ ID NO: 156 AACACGTTCTGAAACATCCATC SEQ ID NO: 157 | TTTCATATTTATTTTTGCTTGTTTGT SEQ ID NO: 158 | CCGGCCTGCTTGTTTGTT SEQ ID NO: 159 | 82 | 75 |
| Yc1RG148 | [Label]CACGTTCTGAAACATCCATCTC SEQ ID NO: 260 CACCTTCTGAAACATCCATCTC SEQ ID NO: 261 | TCCAGTITCATATTTATTTTTGCTTG SEQ ID NO: 262 | CGGCCTGCTTGTTTGTTTTA SEQ ID NO: 263 | 91 | 76 |
| SVA306 | [TMR]TGGAGGCCTCTGCTATTTTC SEQ ID NO: 160 TGGAGGCCTCTGCTATTTTC SEQ ID NO: 161 | GAAGGGTTCATTAAAGAATTTTCATAG SEQ ID NO: 162 | GAGAGGGAGAGGGACAAGAA SEQ ID NO: 163 | 71 | 74 |
| SVA323 | [TMR]TGTGCTTCATTTGAGAAAGCTG SEQ ID NO: 164 TGTGCTTCATTTGAGAAAGCTG SEQ ID NO: 165 | GCTGGCCGGAAGTCTTAATGC SEQ ID NO: 166 | GTTGAAGGATAGAAGTCTTAATGCAG SEQ ID NO: 167 | 120 | 117 |
| Ya5-MLS26 | [FAM]AGGGAAGCCAAAAGATTGGA SEQ ID NO: 168 AGGGAAGCCAAAAGATTGGA SEQ ID NO: 169 | TTGTGCCTCTTACATTTTCTTTTTA SEQ ID NO: 170 | CCGGCCTACATTTTCTTTT SEQ ID NO: 171 | 83 | 81 |
| YB9NBC10 | [ROX]TTGCCACTTTCATTTCTATTGC SEQ ID NO: 172 TTGCCACTTTCATTTCTATTGC SEQ ID NO: 173 | CATTCAAATGGTCTTTTTCCTT SEQ ID NO: 174 | CGGCCCTTTTTCCTTTCTTA SEQ ID NO: 175 | 89 | 83 |
| Ya5NBC216 | [FAM]TGAATGAAGAAACTTGGCACTC SEQ ID NO: 176 TGAATGAATAAACTTGGCACTC SEQ ID NO: 177 | GGTATGCTGGTACTCTGTGTCTG SEQ ID NO: 178 | GCCCGGCCGTCTGTATGTT SEQ ID NO: 179 | 110 | 101 |
| Ya5ACA1766 | [ROX]TCCTTGAGCACAAAGACCAA SEQ ID NO: 180 TCCTTGAGCACAAAGACCAA SEQ ID NO: 181 | GGTACTCTGGAAGACACTGTCCTAA SEQ ID NO: 182 | CGGCCGACACTGTCCTAA SEQ ID NO: 183 | 68 | 63 |

TABLE 2-continued

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| Ya5ACA1766 | | GCGGCCGACACTGT CCTAA SEQ ID NO: 184 | | | |
| Yb8NBC148 | [ROX]CCTTGGTGATCTT ATCCACTTGT SEQ ID NO: 185 CCTTGGTGATCTTATCC ACTTGT SEQ ID NO: 186 | GACGGCAGTCAAGCA GTGT SEQ ID NO: 187 | CGGCCCAAGCAGTG TTTT SEQ ID NO: 188 | 116 | 114 |
| Ya5NBC102 | [ROX]TAGCTCACCTCT GCTTGTAAGG SEQ ID NO: 189 TAGCTCACCTCTGCTTG TAAGG SEQ ID NO: 190 | GACCTGCTGCCTATA CAGTCACTT SEQ ID NO: 191 | GGATTACAGGCGTG ATACAGTCA SEQ ID NO: 192 | 95 | 99 |
| SB19.12 | [ROX]GAGACTAGAATG ATGAAGAAACCTGA SEQ ID NO: 193 GAGACTAGAATGATGA AGAAACCTGA SEQ ID NO: 194 | GCTCACTGCAACCCT CTGTA SEQ ID NO: 195 | GCCCGGCCCTCTGT ATTT SEQ ID NO: 196 | 111 | 106 |
| Yb8NBC120 | [ROX]GAAAGTGGCAAT TGATTTTGG SEQ ID NO: 197 GAAAGTGGCAATTGAT TTTGG SEQ ID NO: 198 | TTTTACCTCTCTATCC TTGCTTTTATA SEQ ID NO: 199 | CGGCCTTATCCTTG CTTTT SEQ ID NO: 200 | 80 | 75 |
| ch1-2250 | [ROX]TGGACCTGTGCA GTTCAAACC SEQ ID NO: 201 TGGACCTGTGCAGTTC AAACC SEQ ID NO: 298 | GCCCAAAGGTTTGAT TTCAAGTT SEQ ID NO: 202 | GCCGGCCTTGATTT CAAGTTT SEQ ID NO: 203 | 105 | 102 |
| YB8AC1197 | [Label]TGCTGCCCTTAA TCTTTACCA SEQ ID NO: 204 TGCTGCCCTTAATCTTT ACCA SEQ ID NO: 205 | GAGACTTTCATTTCTA AGATGTCTGG SEQ ID NO: 206 | CCCGGCCTTCATTT CTAAG SEQ ID NO: 207 | 104 | 105 |
| Yb8AC1439 | [Label]TGCTGAGCTCCA TGCTATTC SEQ ID NO 208 TGCTGAGCTCCATGCT ATTC SEQ ID NO: 209 | GCTCACCAGCTCTTG ACGTA SEQ ID NO: 210 | AGACGGGGTACCAG CTCTTG SEQ ID NO: 211 | 154 | 159 |
| Yb8NBC69 | [Label]AAATGGTGCTGG GATAGCTG SEQ ID NO: 212 AAATGGTGCTGGGATA GCTG SEQ ID NO: 213 | ATAAGAATTCCAGAA GAAAACCTAGG SEQ ID NO: 214 | ATAAGAATTCCGGC CGGG SEQ ID NO: 215 | 134 | 126 |
| Yb8NBC126 | [Label]AGCTCCTGGAAA AGGGAAAG SEQ ID NO: 216 AGCTCCTGGAAAAGGG AAAG SEQ ID NO: 217 | ATGATGATTGGGGCA CCTTA SEQ ID NO: 218 | ATCCGATTGGGGCA CCTTA SEQ ID NO: 219 | 178 | 177 |

TABLE 2-continued

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| Yb8NBC622 | [Label]GGAATACAATGT AACTGGGGATATGC SEQ ID NO: 220 GGAATACAATGTAACT GGGGATATGC SEQ ID NO: 221 | TGTGCAGGGGAATTC CTTCTAA SEQ ID NO: 222 | GCGCAATCTCGGCT CCTT SEQ ID NO: 223 | 118 | 118 |
| Ya5ACA1153 | [Label]TCGTGGAGGTAC AGTGGATAA SEQ ID NO: 224 TCGTGOAGGTACAGTG GATAA SEQ ID NO: 225 | TGTCCTTCTGTGTCTT CTTAAATATC SEQ ID NO: 226 | CCGGCCCTGTGTCT TCTT SEQ ID NO: 227 | 169 | 168 |
| Yb8NBC18 | [Label]TGCATACGTOTG TCTTCATGT SEQ ID NO: 228 TGCATACGTGTGTCTTC ATGT SEQ ID NO: 229 | AGGAATCGCGTCTCC TATCTGA SEQ ID NO: 230 | CCTCCCAAAGTGCT GCTG SEQ ID NO: 231 | 132 | 131 |
| Yb8NBC67 | [Label]AGAGCGAGATG AACAAAGGAA SEQ ID NO: 232 AGAGCGAGATGAACAA AGGAA SEQ ID NO: 233 | TGTTCATAGCAGCCT ATTCTAGC SEQ ID NO: 234 | CGGGTTCACGCCAT TCTAAGC SEQ ID NO: 235 | 137 | 147 |
| Yb8NBC237 | [Label]TGCTGAGGATAG AGCTATAGCAGA SEQ ID NO: 236 TGCTGAGGATAGAGCT ATAGCAGA SEQ ID NO: 237 | CAAAGCATGTCAACT GTTACGTA SEQ ID NO: 238 | CCCGGCCGTTACGG TTT SEQ ID NO: 239 | 106 | 98 |
| Yc1NBC60 | [Label]AGCAAACAAGG AAGGAGAGAA SEQ ID NO: 240 AGCAAACAAGGAAGG AGAGAA SEQ ID NO: 241 | AGGITAAACCATCTT CTTTCTACA SEQ ID NO: 242 | CCCGGCCTCTTTCTT ACAA SEQ ID NO: 243 | 111 | 103 |
| Ya5NBC157 | [Label]TCACTACCAACC CTCTG SEQ ID NO: 244 TCACTACCAACCCTCT G SEQ ID NO: 245 | TGGAGTTGGGTTTGCT SEQ ID NO: 246 | CGGCCTGGGTTTGC TT SEQ ID NO: 247 | 156 | 155 |
| HS4.75 | [Label]CAGCATTACATA CAATAGTTAGGAGCA SEQ ID NO: 248 CAGCATTACATACAAT AGTTAGGAGCA SEQ ID NO: 249 | ATGATAAGATCTCAT TCTTTTT SEQ ID NO: 250 | CCGGCCGATCTCAT TCTTTT SEQ ID NO: 251 | 110 | 109 |
| pAlu1-90961213 | [Label]TCCTAACAAGGG ACTTTGCAG SEQ ID NO: 252 TCCTAACAAGGGACTT TGCAG SEQ ID NO: 253 | AGATGGGAAAGATTC TCCACTTT SEQ ID NO: 254 | CGGCCTCCCAAAGA AGAT SEQ ID NO: 255 | 124 | 129 |
| Ya5ACA912 | [Label]ACAGAGGCCACC CTGTAGG SEQ ID NO: 256 ACAGAGGCCACCCTGT AGG SEQ ID NO: 257 | TGAGACTGGGTGACT GTGTTTT SEQ ID NO: 258 | ACCTGGCCTGGGTG ACTG SEQ ID NO: 259 | 100 | 102 |

TABLE 2-continued

Primer sequences used for each INNUL marker and the resulting amplicon sizes produced

| Marker | Forward Sequence | Reverse Empty Sequence | Reverse Filled Sequence | Amplicon Size of Empty Allele | Amplicon Size of Filled Allele |
|---|---|---|---|---|---|
| Ya5-NBC171 | [Label]TCCCTGCTAACA TAACATCCA SEQ ID NO: 264 TCCCTGCTAACATAAC ATCCA SEQ ID NO: 265 | CGCACCCAGCTCAAA ATGTA SEQ ID NO: 266 | ACCCGGCCTCAAAA TGTAT SEQ ID NO: 267 | 99 | 97 |
| Ya5NBC212 | [Label]CTTTGGCGCAA GTGGT SEQ ID NO: 268 CATTTGGCGCAAGTGG T SEQ ID NO: 269 | CATGTATTGCATGTTG CTTTTGT SEQ ID NO: 270 | CGCCCGGCCTGTAT T SEQ ID NO: 271 | 71 | 60 |
| Ya5NBC54 | [Label]TCATTGTATCAT CTGCTCTACCTG SEQ ID NO: 272 TCATTGTATCATCTGCT GTACCTG SEQ ID NO: 273 | TTTTTGCTTTAGATTT TTGTT SEQ ID NO: 274 | CGCGCCCGGCCTAG AT SEQ ID NO: 275 | 88 | 90 |
| Ya5NBC335 | [Label]TGGGTACTTTGG CCTTAGAGAA SEQ ID NO: 276 TGGGTACTTTGGCCTTA GAGAA SEQ ID NO: 277 | TGTGAATGACATTTTT ATCCTGT SEQ ID NO: 278 | TTTAGCCGGGATGG TATCCT SEQ ID NO. 279 | 63 | 62 |
| Ya5-MLS37 | [Label]TTTGCCCAGGTA TTTGTTATACATT SEQ ID NO: 280 TTTGCCCAGGTATTTGT TATACATT SEQ ID NO: 281 | TTCAGTTAATTGGGTA TTTTTTAAACCA SEQ ID NO: 282 | CCGGCCTTAATTGG GTATTT SEQ ID NO: 283 | 68 | 69 |
| YaSACA1549 | [Label]ACTCCACAAATA GGTTCTACTTCA SEQ ID NO: 284 ACTCCACAAATAGGTT CTACTTCA SEQ ID NO: 285 | TTTGGTATTTTTCTT TTCATTTAC SEQ ID NO: 286 | CCCGGCCTTTTCTTT TC SEQ ID NO: 287 | 65 | 63 |
| Ya5-MLS04 | [Label]AGGAATCCCTTT CCCAAAAA SEQ ID NO: 288 AGGAATCCCTTTCCCA AAAA SEQ ID NO: 289 | TnTGTGATAATAGAC TTTACTTT SEQ ID NO: 290 | CCCGGCCAATAGAC TTTA SEQ ID NO: 291 | 66 | 64 |
| Yb8NBC225 | [Label]TGAGTCCAGCCC ATTTTAGC SEQ ID NO: 292 TGAGTCCAGCCCATTTT AGC SEQ ID NO: 293 | AATTAGTGTGAAGCA TATAAAAA SEQ ID NO: 294 | TGCACCCGGCATAA AAATAC SEQ ID NO: 295 | 85 | 79 |

*Hill C. et al., *Characterization of 26 MiniSTR Loci for Improved Analysis of Degraded DNA Samples*, Journal of Forensic Science 53(1): 73-80(2008).

Example 3

Primer Preparation

The fluorescently labeled and unlabeled oligonucleotide primers were synthesized by Eurofins MWG Operon (Huntsville, Ala., USA) or Integrated DNA Technologies (Skokie, Ill.). All lyophilized primers (labeled and unlabeled) were dissolved in 10 mM TE (tris(hydroxymethyl) aminomethane ("Tris") and ethylenediamine tetraacetic acid ("EDTA")) Buffer (pH 8.0) to a 100 µM stock concentration (10×), The stock primers were stored at 4° C. until used. Following reconstitution, each primer was diluted using TE Buffer to a final concentration of 10 µM (1×). Each primer mix consisted of three primers: one labeled forward primer and two corresponding unlabeled reverse primers. The combined volume of the two reverse primers was equivalent to the volume of the forward primer. All labeled primers were stored in opaque polypropylene tubes to avoid quenching of the fluorescent tags.

Example 4

Amplification of Labeled Primers

All labeled markers were amplified using the GeneAmp® PCR System 9700 thermal cycler (Applied Biosystems). The final concentrations of reaction components (Bio-Rad) were as follows: 0.625 units of iTaq DNA Polymerase, 1× iTaq buffer composed of 20 mM Tris-HCl, pH 8.4 and 50 mM KCl, 5 mM $MgCl_2$ and 200 μM of each dNTP mix. The volumes of each component are as follows; 0.125 μL of iTaq DNA Polymerase, 2.5 μL of iTaq buffer, 2.5 μL of $MgCl_2$, 0.5 μL of dNTP mix, 17.375 μL of nuclease-free water, 1 μL of primer mix and 1 μL of 0.5 ng DNA, bringing the final reaction volume to 25 μL. All runs included 0.5 ng/μL of K562 DNA standard (Promega Corporation) as a positive control and negative control. All labeled markers were amplified using the same conditions:

| Cycling parameters: | | | |
|---|---|---|---|
| 95° C. for 3 min | 95° C. for 0.30 min \| 60° C. for 0.30 min \| 72° C. for 0.30 min \| | 32 cycles | 72° C. for 10.00 min 4° C. for Infinite Time |

Example 5

Data Analysis Using ABI 310 and 3130 Capillary Electrophoresis Systems

After amplification, samples were prepared by combining 20 μL of Hi-Di™ formamide, 0.25 μL of 350 ROX™ (or CC5 Internal Lane Standard 500) size standard and 1 μL of DNA product per reaction. Samples were incubated at 95° C. for 3 minutes. Separation and detection of STR amplification products were performed on an ABI Prism® 310 Genetic Analyzer (Applied Biosystems) using the following parameters for the GS STR POP4 (1 ml) F module: injection at 15 kV for 5 seconds, 15 kV separation at 60° C., run time of 28 minutes. Separation and detection of STR amplification products were performed on an ABI Prism® 3130 Genetic Analyzer (Applied Biosystems) using the following parameters for the GS STR POP4 (1 ml) G5v2 module: injection at 1.2 kV for 12 seconds, data delay time at 1 second and run time at 960 seconds. Data was analyzed using the GeneMapper ID Software version 3.2 (Applied Biosystems).

Electropherograms were interpreted based on peak height and allele drop-out for each marker when compared to the control, based on a minimum detection threshold of 50 RFUs. A macro was created for each marker to identify all peaks as either Insertion or No Insertion and to determine the peak height and amplicon size. The labeled markers were then tested for quality control and reproducibility, re-amplifying DNA samples with all three genotypes (heterozygote, No Insertion homozygote, and Insertion homozygote) to ensure that accurate profiles were obtained.

Example 6

Design of a Multiplex for Simultaneous Amplification of Fifteen and Twenty Markers Fifteen retrotransposable element (RE) markers and Amelogenin were multiplexed to provide simultaneous amplification of all the Insertion and No-insertion alleles for each marker in a four-dye system. The expected sizes of markers are presented in FIG. 4. For each of the fifteen markers and Amelogenin, Table 3a shows the dye attached to the associated forward primer, the type of allele, the sequence lengths of corresponding null and insertion alleles and the chromosome number corresponding to the location in the genome where the allele is found.

TABLE 3a

Fifteen marker multiplex showing name, type, dye label, chromosome number, and amplicon sizes

| | Selected Marker | Dye | Type | Null Allele Size (bp) | Insertion Allele Size (bp) | Chromosome Number |
|---|---|---|---|---|---|---|
| 1 | CHR20-79712 | FAM | LINE | 56 | 52 | 20 |
| 2 | Ya5-MLS48 | FAM | Alu | 79 | 73 | 2 |
| 3 | Ya5ACA1736 | FAM | Alu | 108 | 99 | 8 |
| 4 | Yb8NBC106 | FAM | Alu | 119 | 115 | 21 |
| 5 | Yb8AC1141 | JOE | Alu | 58 | 52 | 3 |
| 6 | Ya5-MLS18 | JOE | Alu | 73 | 70 | 11 |
| 7 | Yb8NBC13 | JOE | Alu | 87 | 90 | 16 |
| 8 | YA5ac2265 | JOE | Alu | 101 | 97 | 13 |
| 9 | MLS9R | JOE | Alu | 118 | 112 | 1 |
| 10 | TARBP1 | TMR | Alu | 59 | 55 | 1 |
| 11 | Amelogenin | TMR | — | X = 79 | Y = 82 | X & Y |
| 12 | Ya5NBC241 | TMR | Alu | 98 | 93 | 15 |
| 13 | HS4.69 | TMR | Alu | 114 | 109 | 5 |
| 14 | Ya5NBC51 | TMR | Alu | 120 | 124 | 3 |
| 15 | Ya5ACA1766 | ROX | Alu | 68 | 63 | 8 |
| 16 | CH1-2250 | ROX | LINE | 105 | 102 | 1 |

Twenty retrotransposable element (RE) markers and Amelogenin were multiplexed to provide simultaneous amplification of all the Insertion and No-Insertion alleles for each marker in a four-dye system. The expected sizes of markers are presented in FIG. 5. For each of the twenty markers and Amelogenin, Table 3b shows the dye attached to the associated forward primer, the type of allele, the sequence lengths of corresponding null and insertion alleles and the chromosome number corresponding to the location in the genome where the allele is found.

TABLE 3b

Twenty marker multiplex showing name, type, dye label, chromosome, number and amplicon sizes

| | Selected Marker | Florescence Dye | Type | Chromosome | Insertion Amplicon Size (bp) | Non-Insertion Amplicon Size (bp) |
|---|---|---|---|---|---|---|
| 1 | AC 004027.1 | FAM | Alu | 7 | 67 | 70 |
| 2 | Ya5-MLS26 | FAM | Alu | 3 | 81 | 83 |
| 3 | 79712 | FAM | LINE | 20 | 93 | 97 |
| 4 | Ya5NBC216 | FAM | Alu | 7 | 101 | 110 |
| 5 | Yb8NBC106 | FAM | Alu | 21 | 115 | 120 |

TABLE 3b-continued

Twenty marker multiplex showing name, type, dye label, chromosome, number and amplicon sizes

|   | Selected Marker | Florescence Dye | Type | Chromosome | Insertion Amplicon Size (bp) | Non-Insertion Amplicon Size (bp) |
|---|---|---|---|---|---|---|
| 6 | Yc1RG148 | JOE | Alu | 2 | 75 | 82 |
| 7 | Yb8NBC13 | JOE | Alu | 16 | 89 | 91 |
| 8 | Ya5ac2265 | JOE | Alu | 13 | 98 | 102 |
| 9 | Ya5-MLS09 | JOE | Alu | 1 | 113 | 119 |
| 10 | Yb8AC1141 | TAMRA | Alu | 3 | 62 | 67 |
| 11 | TARBP1 | TAMRA | Alu | 1 | 71 | 75 |
| 12 | Amelogenin | TAMRA | INDEL | X, Y | 79 | 81 |
| 13 | Ya5ac2305 | TAMRA | Alu | 13 | 93 | 94 |
| 14 | NC 000005.10 | TAMRA | Alu | 5 | 110 | 115 |
| 15 | Ya5NBC51 | TAMRA | Alu | 3 | 125 | 121 |
| 16 | Ya5ACA1766 | ROX | Alu | 8 | 63 | 68 |
| 17 | Yb8NBC120 | ROX | Alu | 22 | 75 | 80 |
| 18 | Yb9NBC10 | ROX | Alu | 4 | 83 | 89 |
| 19 | Ya5NBC102 | ROX | Alu | 17 | 99 | 95 |
| 20 | Sb19.12 | ROX | Alu | 19 | 106 | 111 |
| 21 | Yb8NBC148 | ROX | Alu | 14 | 114 | 116 |

The markers were selected, and the system was optimized as follows:

Initial efforts towards marker selection focused on the set of forensic candidate markers discussed in Mamedov, et al, referenced supra. Using these markers as a benchmark, and the previously described Mini-Primer strategy, an attempt was made to reduce the amplicon size of a subset of markers from Mamedov, et al., referenced supra. Primers for five markers were designed such that all amplicons were less than 120 bp in size for both the insertion and null alleles. Gel electrophoresis was used to visualize the products of the reactions. This result supported the validity of the Mini-Primer strategy.

Following this initial success, retrotransposable element (RE) markers (Alu's, LINES and SVA) were chosen from the literature (Batzer, M. A., et al. (1994); Feng, Q., et al.; Ustyugova, S. V., et al.; Mamedov, I. Z., et al.; Novick, G. E., et al.; Wang, J., et al.; McGinnis, S., et al., all referenced supra). Through analysis of amplicon size and analytical performance of individual markers, a set of candidate markers were selected to demonstrate the validity of the Mini-Primer approach for multiplexing INNULs. These loci are described in Table 3c. Once selected, the primer concentration for each marker was optimized. Heterozygous samples for each marker were balanced and the peak height ratios were determined. Optimization through increasing the primer concentration of "weak" alleles and decreasing the primer concentration of "strong" alleles was performed in a series of reactions. Using the same DNA samples, the peaks for each marker were rebalanced in a multiplex by adding the markers to reactions in a stepwise fashion. Most markers already exhibited balanced peaks while other primer mix ratios were modified.

TABLE 3c

Markers meeting preferred amplicon size and analytical performance criteria.

|   | Selected Marker |
|---|---|
| 1 | TARBP1 |
| 2 | Ya5-MLS48 |
| 3 | Yb8AC1141 |
| 4 | Ya5NBC51 |

TABLE 3c-continued

Markers meeting preferred amplicon size and analytical performance criteria.

|   | Selected Marker |
|---|---|
| 5 | HS4.69 (NC000005.10) |
| 6 | Ya5ACA1736 |
| 7 | Ya5-MLS18 |
| 8 | Y5ac2305 |
| 9 | Ya5NBC241 |
| 10 | Yb8NBC13 |
| 11 | CHR20-79712 |
| 12 | Yb8NBC106 |
| 13 | Ya5-MLS09 |
| 14 | Ya5-MLS26 |
| 15 | AC4027 |
| 16 | Yc1RG148 |
| 17 | Yb9NBC10 |
| 18 | Ya5NBC216 |
| 19 | Ya5ACA1766 |
| 20 | Yb8NBC148 |
| 21 | Ya5NBC102 |
| 22 | SB19.12 |
| 23 | Yb8NBC120 |

The selected markers for multiplexing represent a total of 20 markers, 15 Alu's, and 2 LINEs, 2 SVAs and Amelogenin with amplicons that are between 56 and 125 bp in length. FIG. 6 shows an example electropherogram of the size range of alleles for 9 multiplexed retrotransposable element (RE) markers and Amelogenin. Thus, it is feasible to generate amplified products of the allelic states of Alu's, LINEs and SVAs in a multiplexed reaction that is more suited for forensic samples and in actuality is better suited for high quality samples as well. When the size is similar for amplified products of allelic states, assays tend to be more robust and demonstrate less preferential amplification of the smaller sized allele.

Example 7

Optimization of the Multiplex Reaction for Simultaneous Amplification of Fifteen Markers Primer quality was assured as follows. One of the biggest hurdles to optimizing the multiplex reaction for primers that produce products with large PCR product size differences is allele drop out of larger alleles due to preferential amplification of the shorter product. This issue is addressed by designing the primers with comparable allele sizes (generally between 2-8 bp difference between the Empty and Filled alleles). Primer designs were performed using Primer 3 software. For each primer the $T_m$ value calculated using a default salt concentration was within 5° C. (57°-62° C.). Primer nucleotide composition and sequences were examined to eliminate primer-primer interaction in order to prevent the primers from binding among themselves rather than the target DNA template.

Primer modification with "G" tail and fluorescent dye labeling is another way to improve the quality of the data. During amplification, Taq DNA polymerase often adds an extra Adenosine (A) nucleotide at the 3' end of the product (Magnuson V. L., et. al., *Substrate Nucleotide-Determined Non-Templated Addition of Adenine by Taq DNA Polymerase: Implications for PCR-Based Genotyping and Cloning*, BioTechniques 2.1(4): 700-709 (1996)). The resulting product is termed "+A" product. The extent of this extra A addition depends on the sequence at the 5' end of the opposing primer. This gives a split peak with "−A" and +A, one base difference in size of the PCR product. Brownstein and coworkers (Brownstein M. J., et. al., *Modulation of Non-Templated Nucleotide Addition by Taq DNA Polymerase: Primer Modifications that Facilitate Genotyping*, BioTechniques 20(6): 1004-1006, 1008-1010 (1996)) reported that if the nucleotide on the 5' terminus of the unlabeled primer is a Guanine (G), complete addition of A is favored and the resulting product is homogeneous. The presence of a G adjacent to the dye label decreases the fluorescence intensity and thus the detection of +A/−A products is avoided. To avoid +A/−A products with many of the primer sets, an extra step at the end of the amplification cycle, for 10 minutes at 72° C. is performed.

An optimum concentration of the primers for use in the multiplex reaction was found as follows. Initially, five markers labeled with 6-carboxyfluorescein (6-FAM) were multiplexed using 1.0 µL, 1.5 µL and 2.0 µL of each primer mix per reaction. Samples were then amplified and analyzed using the Amplification of Labeled Primers and Data Analysis for ABI 310 or 3130 protocols, respectively. Results suggest that 1 µL of primer mix was more effective and showed optimum peak heights of 1000-2000 RFUs when compared to 1000 RFUs and 500 RFUs for 1.5 µL and 2 µL respectively. 1 µL of each primer mix was used when performing the peak ratio test for multiplexed samples. Heterozygous samples were used to assess peak balance and optimize peak height ratios.

The $MgCl_2$ concentration used in the multiplex reaction was optimized. Optimization of the $Mg^{2+}$ ion was performed for each selected marker individually. Final concentrations of $MgCl_2$ tested in various multiplexes were 1.5 mM, 2.0 mM, 2.5 mM 5.0 mM, and 6.0 mM. A 6 mM concentration was selected for InnoTyper™ 21 due to optimal peak morphology and balance, and reduction of non-specific artifacts at this concentration.

The above testing and optimization resulted in a preferred multiplex of 15 markers and Amelogenin, termed InnoTyper™. and a preferred multiplex of 20 markers and Amelogenin, termed InnoTyper 21™. These multiplex marker sets correspond to those of Tables 3 and 3a above, respectively. Useful primer sets for InnoTyper™ and InnoTyper 21™ are shown in Tables 4 and 5 below.

TABLE 4

InnoTyper ™ markers and primers

| Marker | Forward Sequence | Reverse Empty Sequence | Reverse Filled Sequence | Amplicon Size of Empty Allele | Amplicon Size of Filled Allele |
|---|---|---|---|---|---|
| CHR20-79712 | [6~FAM]CTGGACCTCTCCATCCCTAT SEQ ID NO: 116 | AGTTTGCACGTAAGACAGAATTT SEQ ID NO: 118 | CCGGCCAAGACAGAATTT SEQ ID NO: 119 | 97 | 93 |
| Ya5-MLS48 | [6~FAM]TTGGCTTGTAAACTAATTGCTG SEQ ID NO: 19 | GCAAAGCAACTTGCACCTTTTCTA SEQ ID NO: 21 | GCGGCCGCACCTTTTCTATTG SEQ ID NO: 22 | 87 | 81 |
| Ya5ACA 1736 | [6~FAM]CCTGCTCTGCACACTTCTTG SEQ ID NO: 51 | GACCTTGACCTAGAGAAGGCAAT SEQ ID NO: 53 | GCCGAGAAGGCAATTTTCTA SEQ ID NO: 54 | 112 | 109 |
| Yb8NBC106 | [6~FAM]CATCAAACTCCAGAGTTCCTAAG SEQ ID NO: 130 | GATTGATGAGGACTCAGGTTGA SEQ ID NO: 132 | GGATTACAGGCGTGAGGATT SEQ ID NO: 133 | 120 | 115 |
| Yb8AC1141 | [TMR]TACAAATACTACAGACAAAGCTACTGA SEQ ID NO: 23 | GAGAACCCCACCAACCTGACT SEQ ID NO: 25 | CCGGCCCAACCTGACTTA SEQ ID NO: 26 | 67 | 62 |
| Ya5-MLS18 | [ROX]AACTTCAAGGTATTTGCATCATG SEQ ID NO: 77 | TGCTAGCTAACTCTCTAAGGTCTT SEQ ID NO: 79 | CCGGCCTCTAAGGTCTTTTT SEQ ID NO: 80 | 79 | 76 |
| Yb8NBC13 | [JOE]CTGGCAAATGCTACCCAACT SEQ ID NO: 105 | GCATCTTCCTCTTCACATCTTAT SEQ ID NO: 107 | GGCCCCTCTTCACATCT SEQ ID NO: 108 | 91 | 89 |
| Ya5ac2265 | [JOE]AGAAGAGTGAATGCACATTTATGA SEQ ID NO: 97 | GGAGTCATGAATTCAGTTTCTTA SEQ ID NO: 99 | GCCCGGCCCAGTTTCTTA SEQ ID NO: 100 | 102 | 98 |

TABLE 4-continued

InnoTyper ™ markers and primers

| Marker | Forward Sequence | Reverse Empty Sequence | Reverse Filled Sequence | Amplicon Size of Empty Allele | Amplicon Size of Filled Allele |
|---|---|---|---|---|---|
| Ya5-MLS09 | [JOE]AGCAGATTTCAGGTCATT ATTGTTT SEQ ID NO: 134 | TTTCTCTCAGAAGCTAT CTCAATTTTAA SEQ ID NO: 136 | CGGCCTGCTATCTC AATTT SEQ ID NO: 137 | 119 | 113 |
| TARBP1 | [TMR]CCAAAGTTTACTATAAG GAGGCAAA SEQ ID NO: 11 | TGATCCAGTCATTCATC ATTTTAT SEQ ID NO: 13 | CGGCCCATTCATCA GTTT SEQ ID NO: 14 | 75 | 71 |
| Amelogenin | [TMR]CCCTTTGAAGTGGTACC AGAGCA SEQ ID NO: 151 | GCATGCCTAATATTTTC AGGGAATA SEQ ID NO: 153 | • | X = 79 | Y = 81 |
| Ya5NBC241 | [TMR]TTTAGTTCCCCACAATT AACATGA SEQ ID NO: 101 | GCTTTCCCCCAGAAGAT CCAT SEQ ID NO: 103 | GCCGGCCAAGATCC ATTCT SEQ ID NO: 104 | 98 | 93 |
| HS4.69 (NC0000 05.10) | [TMR]TGCCAGGTGATAGTATT AGGAGGTG SEQ ID NO: 44 | GCTAGCTAACTCTCTAA GGTC SEQ ID NO: 46 | CCCGGCCTCTAAGGT CTTTTT SEQ ID NO: 47 | 115 | 110 |
| YaSNBC51 | [TMR]TCGCCATCTCTTCTTCCT TCA SEQ ID NO: 37 | GTCCAGGGTTAATGCTT TGTT SEQ ID NO: 39 | TTACAGGCGTGAGA ATGCTT SEQ ID NO: 40 | 121 | 125 |
| Ya5ACA 1766 | [ROX]TCCTTGAGCACAAAGAC CAA SEQ ID NO: 180 | GGTACTCTGGAAGACA CTGTCCTAA SEQ ID NO: 182 | CGGCCGACACTGTC CTAA SEQ ID NO: 183 | 68 | 63 |
| CH1-2250 | [ROX]TGGACCTGTGCAGTTCA AACC SEQ ID NO: 201 | GCCCAAAGGTTTGATTT CAAGTT SEQ ID NO: 202 | GCCGGCCTTGATTT CAAGTTT SEQ ID NO: 203 | 105 | 102 |

TABLE 5

InnoTyper 21 ™ markers and primers.

| Marker | Forward Sequence | Reverse Empty Sequence | Reverse Filled Sequence | Amplicon Size of Empty Allele | Amplicon Size of Filled Allele |
|---|---|---|---|---|---|
| AC 004027.1 | [6~FAM]AAGGTCTAAGCGCA GTGGAA SEQ ID NO: 144 | TGTGTTTTGTACAGAGT TCTTAATTGCTAA SEQ ID NO: 146 | CCGGCCCAGAGTTCT TAA SEQ ID NO: 147 | 70 | 67 |
| YA5-MLS26 | [6~FAM]AGGGAAGCCAAAAG ATTGGA SEQ ID NO: 168 | TTGTGCCTCTTACATTTT CTTTTTA SEQ ID NO: 170 | CCGGCCTACATTTTC TTTT SEQ ID NO: 171 | 83 | 81 |
| 79712 | [6~FAM]CTGGACCTCTCCATC CCTAT SEQ ID NO: 116 | AGTTTGCACGTAAGACA GAATTT SEQ ID NO: 118 | CCGGCCAAGACAGA ATTT SEQ ID NO: 119 | 97 | 93 |
| Ya5NBC216 | [6~FAM]TGAATGAAGAAACTT GGCACTC SEQ ID NO: 176 | GGTATGCTGGTACTCTG TGTCTG SEQ ID NO: 178 | GCCCGGCCGTCTGTA TGTT SEQ ID NO: 179 | 110 | 101 |
| Yb8NbC106 | [6~FAM]CATCAAACTCCAGAG TTCCTAAG SEQ ID NO: 130 | GATTGATGAGGACTCAG GTTGA SEQ ID NO: 132 | GGATTACAGGCGTG AGGATT SEQ ID NO: 133 | 120 | 115 |
| Yc1RG148 | [JOE]AACACGTTCTGAAACAT CCATC SEQ ID NO: 156 | TTTCATATTTATTTTTGC TTGTTTGT SEQ ID NO: 158 | CCGGCCTGCTTGTTT GTT SEQ ID NO: 159 | 82 | 75 |
| Yb5NBC13 | [JOE]CTGGCAAATGCTACCCA AGT SEQ ID NO: 105 | GCATCTTCCTCTTCACAT CTTAT SEQ ID NO: 107 | GGCCCCTCTTCACAT CT SEQ ID NO: 108 | 91 | 89 |
| Ya5ac2265 | [JOE]AGAAGAGTGAATGCAC ATTTATGA SEQ ID NO: 97 | GGAGTCATGAATTCAGT TTCTTA SEQ ID NO: 99 | GCCCGGCCCAGTTTC TTA SEQ ID NO: 100 | 102 | 98 |

TABLE 5-continued

InnoTyper 21 ™ markers and primers.

| Marker | Forward Sequence | Reverse Empty Sequence | Reverse Filled Sequence | Amplicon Size of Empty Allele | Amplicon Size of Filled Allele |
|---|---|---|---|---|---|
| Ya5-MLS09 | [JOE]AGCAGATTTCAGGTCAT TATTGTTT SEQ ID NO: 134 | TTTCTCTCAGAAGCTAT CTCAATTTTAA SEQ ID NO: 136 | CGGCCTGCTATCTCA ATTT SEQ ID NO: 137 | 119 | 113 |
| YbSAC1141 | [TMR]TACAAATACTACAGAC AAAAGCTACTGA SEQ ID NO: 23 | GAGAACCCCACCAACCT GACT SEQ ID NO: 25 | CCGGCCCAACCTGA CTTA SEQ ID NO: 26 | 67 | 62 |
| TARBP1 | [TMR]CCAAAGTTTACTATAA GGAGGCAAA SEQ ID NO: 11 | TGATCCAGTCATTCATC ATTTTAT SEQ ID NO: 13 | CGGCCCATTCATCAG TTT SEQ ID NO: 14 | 75 | 71 |
| Amelogein | [TMR]CCCTTTGAAGTGGTAC CAGAGCA SEQ ID NO: 151 | GCATGCCTAATATTTTC AGGGAATA SEQ ID NO: 153 | . | X = 79 | Y = 81 |
| YA5ac2305 | [TMR]TTAAAATACAATCCA ACACCATTT SEQ ID NO: 90 | GGCATCCTTTGATTACA ACTCTTA SEQ ID NO: 92 | GGCCCCAATTACAA CTCT SEQ ID NO: 93 | 94 | 93 |
| HS4.69 (NC0000 05.10) | [TMR]TGCCAGGTGATAGTAT TAGGAGGTG SEQ ID NO: 44 | GCTAGCTAACTCTCTAA GGTC SEQ ID NO: 46 | CCGGCCTCTAAGGTC TTTTT SEQ ID NO: 47 | 115 | 110 |
| Ya5NBC51 | [TMR]TCGCCATCTCTTCTTCC TTCA SEQ ID NO: 37 | GTCCAGGGTTAATGCTT TGTT SEQ ID NO: 39 | TTACAGGCGTGAGA ATGCTT SEQ ID NO: 40 | 121 | 125 |
| Ya5AC A1766 | [ROX]TCCTTGAGCACAAAGA CCAA SEQ ID NO: 180 | GGTACTCTGGAAGACAC TGTCCTAA SEQ ID NO: 182 | CGGCCGACACTGTC CTAA SEQ ID NO: 183 | 68 | 63 |
| Yb8NBC120 | [ROX]GAAAGTGGCAATTGAT TTTGG SEQ ID NO: 197 | TTTTACCTCTCTATCCTT GCTTITATA SEQ ID NO: 199 | CGGCCTTATCCYTGC TTTT SEQ ID NO: 200 | 80 | 75 |
| Yb9NBC10 | [ROX]TTGCCACTTTCATTTCT ATTGC SEQ ID NO: 172 | CATTCAAATGGTCTTTTT CCTT SEQ ID NO: 174 | CGGCCCTTTTTCCTT TCTTA SEQ ID NO: 175 | 89 | 83 |
| Ya5NBC102 | [ROX]TAGCTCACCTCTGCTTG TAAGG SEQ ID NO: 189 | GACCTGCTGCCTATACA GTCACTT SEQ ID NO: 191 | GGATTACAGGCGTG ATACAGTCA SEQ ID NO: 192 | 95 | 99 |
| Sb19.12 | [ROX]GAGACTAGAATGATGA AGAAACCTGA SEQ ID NO: 193 | GCTCACTGCAACCCTCT GTA SEQ ID NO: 195 | GCCCGGCCCTCTGTA TTT SEQ ID NO: 196 | 111 | 106 |
| YB8NBC148 | [ROX]CCTTGGTGATCTTATCC ACTTGT SEQ ID NO: 185 | GACGGCAGTCAAGCAGT GT SEQ ID NO: 187 | CGGCCCAAGCAGTG TTTT SEQ ID NO: 188 | 116 | 114 |

As described in detail above, a method for forming a multiplexed DNA analysis system may comprise using literature sources and BLAST sequence analysis to identify loci that may potentially be of use in the multiplexed DNA analysis system; assessing the identified loci for their suitability for primer design, a DNA marker being associated with each locus; selecting a set of markers for use in the multiplexed DNA analysis system, each marker corresponding to an insertion allele and a null allele; designing a set of three primers for each selected marker using primer design software, each set of three primers consisting of a forward primer and two reverse primers, one reverse primer corresponding to the insertion allele and the other reverse primer corresponding to the null allele, all designed primers having $T_m$ values in the range of 58-63° C., each primer set being designed to generate by polymerase chain reaction (PCR) means an amplicon corresponding to the insertion allele and an amplicon corresponding to the null allele, the amplicons differing in size by about 2 to about 10 base pairs, each primer comprising a nucleotide base sequence and being capable of forming a DNA amplicon by polymerase chain reaction (PCR) means; adding size-modifying moieties at the 5' end of one or more of the primer sequences in order to obtain size-modified primers, the size-modified primers corresponding to amplicons having sizes suitable for inclusion in a multiplex; synthesizing each set of three size-modified primers for each selected marker, the primers being size-modified as needed, attaching a fluorescent label to each forward primer, a plurality of fluorescent labels being selected, each distinct fluorescent label being associated with a series of markers; amplifying each marker of the set of markers using a PCR method; optimizing the primer concentration for each selected marker; testing labeled markers for quality control and reproducibility by amplifying with heterozygote, no insertion homozygote and insertion homozygote genotypes; multiplexing the selected set of markers and amplifying the set of markers simultaneously using the PCR method; separating a resulting set of amplicons using electrophoresis, the amplicons corresponding to each marker being well separated according to amplicon size from amplicons corresponding to each other marker in the same series of markers; and optimizing a concentration of magnesium chloride used in the multiplex reaction.

In certain embodiments, the size-modifying moieties used in the method for forming a multiplexed DNA analysis system of the present invention may be non-hybridizing additional nucleic acids, but useful size-modifying moieties in this context are not limited thereto.

The present invention additionally includes a kit for multiplexed DNA analysis, the kit comprising a DNA standard, the DNA standard comprising DNA at a known DNA concentration, the DNA standard being useful as a positive amplification control during a polymerase chain reaction (PCR) analysis; a Master Mix to support a PCR analysis, the Master Mix comprising a plurality of deoxynucleotides (dNTPs), magnesium chloride and a buffer; a DNA polymerase; a mixture of primers corresponding to a group of chromosomal INNUL markers selected for multiplexing, the mixture of primers including for each selected chromosomal marker a primer set including a forward primer, a reverse primer corresponding to a null allele and a reverse primer corresponding to a filled allele, at least one primer of each primer set including an observable label; and instructions for using the kit in conjunction with one or more instruments comprised by a PCR DNA analysis system, the PCR system providing an amplicon corresponding to each primer, the amplicons corresponding to each primer set being distinguishable from amplicons corresponding to each other primer set by means of a unique combination of amplicon size and observable label.

The kit for multiplexed DNA analysis according to the present invention may provide a DNA genetic profile and may further comprise a software template, the software template being capable of generating a forensic-related or bioancestry-related conclusion from the DNA genetic profile.

Example 8

Population and Statistical Analyses

Two North American sample populations (African American, N=134; and Caucasian, N=48) were typed for the 15 INNUL loci of InnoTyper™. The frequencies of the No-Insertion (N) allele and Insertion (I) allele per locus were determined. Observed heterozygosity, random match probability, and power of discrimination were calculated. Heterozygosities for the markers' departures from linkage equilibrium (i.e., linkage disequilibrium (LD) between pairs of loci) were tested for each of the three populations. Markers with allele frequencies that differ substantially in one or more of the populations tend to be more useful for bioancestry studies. Parentage analysis of 100 cases containing samples from mother, child, and alleged father from Caucasian and African American populations were analyzed using the 16 marker (15 RE's and Amelogenin) multiplex referred as InnoTyper™. Results for father and mother samples from African American and Caucasian populations were used for allele frequencies and genotype frequencies and are presented in Table 6 and Table 7. Analogous population (allele insertion) frequencies for the markers of the InnoTyper 21™ multiplex (20 RE's and Amelogenin) are presented in Table 8.

TABLE 6

Population studies data: Allele frequencies for Caucasian and African American DNA samples obtained by analyzing using 15 RE's Marker Multiplex (InnoTyper ™).
Allele Frequencies for 15 Markers

| MARKER | ALLELE | IN BLACKS | | IN CAUCASIAN | |
|---|---|---|---|---|---|
| | | NUMBER | PERCENT | NUMBER | PERCENT |
| 79712 | I | 0.347 | 34.7 | 0.4896 | 48.96 |
| | N | 0.653 | 65.3 | 0.5104 | 51.04 |
| MLS48 | I | 0.3694 | 36.94 | 0.7813 | 78.13 |
| | N | 0.6306 | 63.06 | 0.2188 | 21.88 |
| 1736 | I | 0.3769 | 37.69 | 0.2083 | 20.83 |
| | N | 0.6231 | 62.31 | 0.7917 | 7917 |
| NBC106 | I | 0.5336 | 53.36 | 0.4167 | 41.67 |
| | N | 0.4664 | 46.64 | 0.5834 | 58.34 |
| 1141 | I | 0.2574 | 25.74 | 0.5625 | 56.25 |
| | N | 0.7425 | 74.25 | 0.4375 | 43.75 |
| MLS18 | I | 0.5714 | 57.14 | 0.6875 | 68.75 |
| | N | 0.4286 | 42.86 | 0.3125 | 31.25 |
| NBC13 | I | 0.3439 | 34.39 | 0.3646 | 36.46 |
| | N | 0.6567 | 65.67 | 0.6354 | 63.54 |
| 2265 | I | 0.3993 | 39.93 | 0.7083 | 70.83 |
| | N | 0.6007 | 60.07 | 0.2917 | 29.17 |
| MLS9 | I | 0.2201 | 22.01 | 0.4583 | 45.83 |
| | N | 0.7799 | 77.99 | 0.5417 | 54.17 |
| TARBP1 | I | 0.2836 | 28.36 | 0.5938 | 59.38 |
| | N | 0.7164 | 71.64 | 0.4062 | 40.62 |
| NBC241 | I | 0.1269 | 12.69 | 0.6979 | 69.79 |
| | N | 0.8731 | 87.31 | 0.3021 | 30.21 |
| HS4.69 (NC000005.10) | I | 0.3022 | 30.22 | 0.3958 | 39.58 |
| | N | 0.6978 | 69.78 | 0.6042 | 60.42 |
| NBC51 | I | 0.4328 | 43.28 | 0.25 | 25 |
| | N | 0.5671 | 56.71 | 0.75 | 75 |
| 1766 | I | 0.7351 | 73.51 | 0.6562 | 65.62 |
| | N | 0.2649 | 26.49 | 0.3438 | 34.38 |
| 2250 | I | 0.0821 | 8.21 | 0.25 | 25 |
| | N | 0.9179 | 91.79 | 0.75 | 75 |

TABLE 7

Population studies: Genotype frequencies of Caucasian and African American populations for 15 retrotransposable element (RE) markers analyzed using the multiplex system.
Genotype Frequencies for 15 Markers

| MARKER | GENOTYPE | IN BLACK | | IN CAUCASIAN | |
|---|---|---|---|---|---|
| | | NUMBER | PERCENT | NUMBER | PERCENT |
| 79712 | I, I | 18 | 13.43 | 10 | 20.83 |
| | I, N | 57 | 42.54 | 27 | 56.25 |
| | N, N | 59 | 44.03 | 11 | 22.92 |
| MLS48 | I, I | 21 | 15.67 | 29 | 60.42 |
| | I, N | 57 | 42.54 | 17 | 35.42 |
| | N, N | 56 | 41.79 | 2 | 4.17 |
| 1736 | I, I | 16 | 11.94 | 3 | 6.25 |
| | I, N | 69 | 51.49 | 14 | 29.17 |
| | N, N | 49 | 36.57 | 31 | 64.58 |
| NBC106 | I, I | 44 | 32.84 | 7 | 14.58 |
| | I, N | 55 | 41.04 | 26 | 54.17 |
| | N, N | 35 | 26.12 | 15 | 31.25 |
| 1141 | I, I | 7 | 5.22 | 17 | 35.42 |
| | I, N | 55 | 41.04 | 20 | 41.67 |
| | N, N | 72 | 53.73 | 11 | 22.92 |
| MLSI8 | I, I | 61 | 45.86 | 25 | 52.08 |
| | I, N | 30 | 22.56 | 16 | 33.33 |
| | N, N | 42 | 31.58 | 7 | 14.58 |

TABLE 7-continued

Population studies: Genotype frequencies of Caucasian and African American populations for 15 retrotransposable element (RE) markers analyzed using the multiplex system.
Genotype Frequencies for 15 Markers

| MARKER | GENOTYPE | IN BLACK NUMBER | IN BLACK PERCENT | IN CAUCASIAN NUMBER | IN CAUCASIAN PERCENT |
|---|---|---|---|---|---|
| NBC13 | I, I | 86 | 64.18 | 14 | 29.17 |
| | I, N | 4 | 2.99 | 7 | 14.58 |
| | N, N | 44 | 32.84 | 27 | 56.25 |
| 2265 | I, I | 22 | 16.42 | 28 | 58.33 |
| | I, N | 63 | 47.01 | 12 | 25 |
| | N, N | 49 | 36.57 | 8 | 16.67 |
| MLS9 | I, I | 4 | 2.99 | 10 | 20.83 |
| | I, N | 51 | 38.06 | 24 | 50 |
| | N, N | 79 | 58.96 | 14 | 29.17 |
| TARBP1 | I, I | 11 | 8.21 | 18 | 37.5 |
| | I, N | 54 | 40.3 | 21 | 43.75 |
| | N, N | 69 | 51.49 | 9 | 18.75 |
| AMEL | XX | 63 | 47.01 | 23 | 47.92 |
| | XY | 71 | 52.99 | 25 | 52.08 |
| NBC241 | I, I | 1 | 0.75 | 24 | 50 |
| | I, N | 32 | 23.88 | 19 | 39.58 |
| | N, N | 101 | 75.37 | 5 | 10.42 |
| HS4.69 (NC000005.10) | I, I | 11 | 8.21 | 7 | 14.58 |
| | I, N | 59 | 44.03 | 24 | 50 |
| | N, N | 64 | 47.76 | 17 | 35.42 |
| NBC51 | I, I | 46 | 34.33 | 9 | 18.75 |
| | I, N | 24 | 17.91 | 6 | 12.5 |
| | N, N | 64 | 47.76 | 33 | 68.75 |
| 1766 | I, I | 72 | 53.73 | 22 | 45.83 |
| | I, N | 53 | 39.55 | 19 | 39.58 |
| | N, N | 9 | 6.72 | 7 | 14.58 |
| 2250 | I, I | 0 | 0 | 4 | 8.33 |
| | I, N | 22 | 16.42 | 16 | 33.33 |
| | N, N | 112 | 83.58 | 28 | 58.33 |

TABLE 8

Population studies data: Allele frequencies for Caucasian and African American DNA samples obtained by analyzing using 20 RE's Marker Multiplex (InnoTyper 21 ™).
Allele frequencies for InnoTyper ™ 21

| MARKER | ALLELE | Caucasian n = 208 FREQUENCY NUMBER | African American n = 202 FREQUENCY NUMBER |
|---|---|---|---|
| AC004027 | I | 0.438 | 0.537 |
| | N | 0.563 | 0.463 |
| Ya5-MLS26 | I | 0.373 | 0.149 |
| | N | 0.627 | 0.851 |
| CHR20-79712 | I | 0.481 | 0.309 |
| | N | 0.519 | 0.691 |
| Ya5NBC216 | I | 0.709 | 0.599 |
| | N | 0.291 | 0.401 |
| Yb8NBC106 | I | 0.442 | 0.574 |
| | N | 0.558 | 0.426 |
| Yc1RG148 | I | 0.293 | 0.530 |
| | N | 0.707 | 0.470 |
| Yb8NBC13 | I | 0.365 | 0.225 |
| | N | 0.635 | 0.775 |
| Ya5ac2265 | I | 0.726 | 0.396 |
| | N | 0.274 | 0.604 |
| Ya5-MLS09 | I | 0.428 | 0.233 |
| | N | 0.572 | 0.767 |
| Yb8AC1141 | I | 0.611 | 0.233 |
| | N | 0.389 | 0.767 |
| TARBP1 | I | 0.577 | 0.282 |
| | N | 0.423 | 0.718 |
| Ya5ac2305 | I | 0.560 | 0.304 |
| | N | 0.440 | 0.696 |
| ALU-HS4.69 | I | 0.380 | 0.317 |
| | N | 0.620 | 0.683 |
| Ya5NBC51 | I | 0.517 | 0.594 |
| | N | 0.483 | 0.406 |
| Ya5ACA1766 | I | 0.613 | 0.728 |
| | N | 0.387 | 0.272 |
| Yb8NBC120 | I | 0.409 | 0.597 |
| | N | 0.591 | 0.403 |
| Yb9NBC10 | I | 0.442 | 0.661 |
| | N | 0.558 | 0.339 |
| Ya5NBC102 | I | 0.421 | 0.391 |
| | N | 0.579 | 0.609 |
| Sb19.12 | I | 0.310 | 0.391 |
| | N | 0.690 | 0.609 |
| Yb8NBC148 | I | 0.863 | 0.547 |
| | N | 0.137 | 0.453 |

Parentage analysis of 100 cases containing samples from mother, child, and alleged father were analyzed for the following parameters:

RMP=Random Match Probability (sum of squares of three genotype frequencies under HWE assumption)

PD=Probability of Discrimination=1−RMP

PE (Trio)=Paternity Exclusion Probability with data on Trio (i.e., mother-child-Alleged father)=H(2−H)/4, where H is the expected Heterozygosity for a hi-allelic locus under HWE PE (Det) Paternity Exclusion Probability in motherless cases with data on child and Alleged father only)=½. $H^2$ PI(min) Minimum Paternity Index (for a non-excluded allege father)=1/{4(1−p)}, where p is the frequency of the rarer allele of a hi-allelic locus PI(max)=Maximum Paternity Index (for a non-excluded allege father)=1/p, where p is the frequency of the rarer allele of a bi-allelic locus The results are summarized in Table 9 and Table 10.

TABLE 9

Estimates of Forensic and Parentage Testing Parameters of the 15 Markers in the Caucasian Population

| Marker | RMP | PD | PE (Trio) | PE (Def) | PI (min) | PI (Max) |
|---|---|---|---|---|---|---|
| 79712 | 0.3751 | 0.6249 | 0.1875 | 0.1249 | 0.4898 | 2.0425 |
| MLS48 | 0.4917 | 0.5083 | 0.1417 | 0.0584 | 0.3200 | 4.5725 |
| 1736 | 0.3915 | 0.6085 | 0.1797 | 0.1103 | 0.4012 | 2.6532 |
| NBC106 | 0.3761 | 0.6239 | 0.1869 | 0.1239 | 0.4685 | 2.1441 |
| 1141 | 0.4545 | 0.5454 | 0.1546 | 0.0731 | 0.3367 | 3.8835 |

TABLE 9-continued

Estimates of Forensic and Parentage Testing Parameters of the
15 Markers in the Caucasian Population

| Marker | RMP | PD | PE (Trio) | PE (Def) | PI (min) | PI (Max) |
|---|---|---|---|---|---|---|
| MLS9 | 0.4902 | 0.5098 | 0.1422 | 0.0589 | 0.3206 | 4.5434 |
| TARBP1 | 0.4350 | 0.5650 | 0.1619 | 0.0825 | 0.3490 | 3.5261 |
| NBC241 | 0.6305 | 0.3695 | 0.0985 | 0.0246 | 0.2863 | 7.8802 |
| HS4.69 (NC000005.10) | 0.4233 | 0.5767 | 0.1663 | 0.0889 | 0.3583 | 3.3091 |
| 1766 | 0.4196 | 0.5804 | 0.1679 | 0.0911 | 0.3401 | 3.7750 |
| 2250 | 0.7327 | 0.2673 | 0.0697 | 0.0114 | 0.2724 | 12.1803 |
| MLS18 | 0.3803 | 0.6197 | 0.1849 | 0.1200 | 0.4375 | 2.3332 |
| NBC13 | 0.4032 | 0.5968 | 0.1746 | 0.1017 | 0.3807 | 2.9129 |
| NBC51 | 0.3796 | 0.6204 | 0.1852 | 0.1205 | 0.4408 | 2.3105 |
| 2265 | 0.3858 | 0.6142 | 0.1823 | 0.1151 | 0.4162 | 2.5044 |
| Combined | | | | | | |
| 15 loci | $4.85 \times 10^{-6}$ | 0.999995 | 0.9263 | 0.7474 | $3.22 \times 10^{-7}$ | 156 million |

TABLE 10

Estimates of Forensic and Parentage Testing Parameters of the
15 Markers in the African-American Population

| Marker | RMP | PD | PE (Trio) | PE (Def) | PI (min) | PI (Max) |
|---|---|---|---|---|---|---|
| 79712 | 0.4017 | 0.5983 | 0.1753 | 0.1027 | 0.3828 | 2.8818 |
| MLS48 | 0.3938 | 0.6062 | 0.1787 | 0.1085 | 0.3964 | 2.7071 |
| 1736 | 0.3915 | 0.6085 | 0.1797 | 0.1103 | 0.4012 | 2.6532 |
| NBC106 | 0.3761 | 0.6239 | 0.1869 | 0.1239 | 0.4685 | 2.1441 |
| 1141 | 0.4545 | 0.5455 | 0.1546 | 0.0731 | 0.3367 | 3.8835 |
| MLS9 | 0.4902 | 0.5098 | 0.1422 | 0.0589 | 0.3206 | 4.5434 |
| TARBP1 | 0.4350 | 0.5650 | 0.1619 | 0.0825 | 0.3490 | 3.5261 |
| NBC241 | 0.6305 | 0.3695 | 0.0985 | 0.0246 | 0.2863 | 7.8802 |
| HS4.69 (NC000005.10) | 0.4233 | 0.5767 | 0.1664 | 0.0889 | 0.3583 | 3.3091 |
| 1766 | 0.4196 | 0.5804 | 0.1679 | 0.0911 | 0.3401 | 3.7750 |
| 2250 | 0.7327 | 0.2673 | 0.0697 | 0.0114 | 0.2724 | 12.1803 |
| MLS18 | 0.3803 | 0.6197 | 0.1849 | 0.1200 | 0.4375 | 2.3331 |
| NBC13 | 0.4032 | 0.5968 | 0.1746 | 0.1017 | 0.3807 | 2.9129 |
| NBC51 | 0.3796 | 0.6204 | 0.1852 | 0.1205 | 0.4408 | 2.3105 |
| 2265 | 0.3858 | 0.6142 | 0.1823 | 0.1151 | 0.4162 | 2.5044 |
| Combined | | | | | | |
| 15 loci | $4.16 \times 10^{-6}$ | 0.999996 | 0.9284 | 0.7548 | $3.12 \times 10^{-7}$ | 130 million |

The results indicated that most of the markers follow Hardy Weinberg Equilibrium. Since the populations samples were from Mother and Father of Paternity cases and samples were collected from a rural county, relatedness among donors could be a possibility, further analysis using random DNA samples obtained from unrelated individuals are needed to confirm whether to eliminate a few of the markers to make the multiplex more suitable for forensic and paternity applications. However, the preliminary data indicate that a 15-20 marker multiplexed RE will provide high Paternity index and high power of discrimination and can be successfully used for paternity application as a standalone marker system.

Population and statistical analysis were performed with either GDA software (Lewis, P. O., et al., *Genetic Data Analysis: Computer program for the analysis of allelic data*, Version 1.0 (2001)), Arlequin 3.11 (Excoffier, L., et al., *Arlequin (version 3.0): an integrated software package for population genetics data analysis*, Evolutionary Bioinformatics Online, 1: 47 (2005)), or in-house developed software. Departures from Hardy-Weinberg equilibrium (HWE) and linkage equilibrium were tested using Fisher's exact test. Bonferroni's correction for multiple comparisons was performed according to Weir and Cockerham [33].

Allele frequency is a measure of the relative frequency of an allele of a genetic locus in a specific population. Usually it is expressed as a proportion or a percentage. Allele frequencies show the genetic diversity of a species population or equivalently the richness of its gene pool. Allele frequencies for the INNUL markers were analyzed in the Caucasian and African American populations, and the results are shown in Table 11. The frequency of the empty (or no insertion) marker is represented by $P_E$. The frequency of the filled (or insertion) marker is represented by $P_F$. Allele frequencies following Hardy Weinberg equilibrium as described as $a^2$ for the homozygous empty genotype; 2ab for the heterozygote genotype; and $b^2$ for the homozygous filled genotype.

TABLE 11

Allele Frequencies of Markers

| Markers | Alias | Marker Type | Caucasian Probability $P_E$ | $P_F$ | Allele Frequency $a^2$ | 2ab | $b^2$ | African American Probability $P_E$ | $P_F$ | Allele Frequency $a^2$ | 2ab | $b^2$ |
|---|---|---|---|---|---|---|---|---|---|---|---|---|
| LC3-2601 | L2601 | Ancestry | 0.016 | 0.984 | 3E-04 | 0.032 | 0.968 | 0.523 | 0.477 | 0.273 | 0.499 | 0.228 |
| Yac52265 | 2265 | Forensic | 0.247 | 0.753 | 0.061 | 0.372 | 0.567 | 0.72 | 0.28 | 0.518 | 0.403 | 0.079 |
| CH14-50-6236 | 6236 | Forensic | 0.726 | 0.274 | 0.527 | 0.398 | 0.075 | 0.488 | 0.512 | 0.238 | 0.5 | 0.262 |
| CH4-12-7012 | 7012 | Ancestry | 0.022 | 0.9795 | E-04 | 0.042 | 0.957 | 0.198 | 0.802 | 0.039 | 0.317 | 0.644 |
| Y5ac2305 | 2305 | Forensic | 0.441 | 0.559 | 0.194 | 0.493 | 0.312 | 0.755 | 0.245 | 0.57 | 0.37 | 0.06 |
| Ya5NBC51 | 51 | Forensic | 0.467 | 0.533 | 0.218 | 0.498 | 0.284 | 0.421 | 0.58 | 0.177 | 0.487 | 0.336 |
| Yb7AD155 | 155 | Forensic | 0.544 | 0.456 | 0.296 | 0.496 | 0.208 | 0.587 | 0.413 | 0.345 | 0.485 | 0.17 |
| CH6-28-9163 | 9163 | Ancestry | 0.467 | 0.533 | 0.218 | 0.498 | 0.284 | 0.758 | 0.242 | 0.575 | 0.367 | 0.058 |
| Yb8NBC106 | 106 | Forensic | 0.5 | 0.5 | 0.25 | 0.5 | 0.25 | 0.449 | 0.551 | 0.202 | 0.495 | 0.303 |
| Yb8AC1141 | 1141 | Forensic | 0.39 | 0.61 | 0.152 | 0.476 | 0.372 | | | | | |
| Ya5-MLS48 | MLS48 | Forensic | 0.206 | 0.794 | 0.042 | 0.327 | 0.63 | 0.628 | 0.372 | 0.394 | 0.467 | 0.138 |
| TARBP1R | TARBP1 | Forensic | 0.436 | 0.565 | 0.19 | 0.492 | 0.319 | 0.683 | 0.317 | 0.467 | 0.433 | 0.1 |
| HS4.69 (NC000005.10) | HS4.69R | Forensic | 0.59 | 0.41 | 0.348 | 0.484 | 0.168 | | | | | |
| CHR22-19250 | 9250 | Forensic | 0.34 | 0.66 | 0.116 | 0.449 | 0.436 | | | | | |
| Yb8AC1796 | 1796 | Forensic | 0.63 | 0.37 | 0.397 | 0.466 | 0.137 | | | | | |
| CHR20-79712 | 9712 | Forensic | 0.51 | 0.49 | 0.26 | 0.5 | 0.24 | | | | | |
| CH1-6217R | 6217R | Forensic | 0.69 | 0.31 | 0.476 | 0.428 | 0.096 | 0.539 | 0.461 | 0.291 | 0.497 | 0.213 |
| Ya5ACA1766 | 1766 | Forensic | 0.32 | 0.68 | 0.102 | 0.435 | 0.462 | | | | | |
| pAlu-19-2139 | 2139 | Forensic | 0.54 | 0.46 | 0.292 | 0.497 | 0.212 | | | | | |
| Ya5-MLS18R | MLS18R | Forensic | 0.39 | 0.61 | 0.152 | 0.476 | 0.372 | | | | | |
| MLS9 | MLS9 | Forensic | 0.54 | 0.46 | 0.292 | 0.497 | 0.212 | | | | | |
| YA5-MLS26 | MLS26 | Forensic | 0.55 | 0.45 | 0.303 | 0.495 | 0.203 | | | | | |
| AC4027 | 4027 | Forensic | 0.58 | 0.42 | 0.336 | 0.487 | 0.176 | | | | | |

Example 9

Study of the Effectiveness of the Multiplex Reaction Using Degraded DNA Samples

Five single source DNA samples were sonicated up to eight hours. One ng input DNA was amplified with the 15 RE+Amelogenin multiplex that is referred to as Inno-Typer™ and compared to PowerPlex® 16HS, Identifiler® Plus and Minifiler™ using an ABI Prism® 3130 Genetic Analyzer (Applied Biosystems).

InnoTyper™ produced results at more loci for the degraded samples than did the STR kits and, therefore, outperformed all three STR kits tested, including Mini-Filer™. This data shows that the InnoTyper™ kit is highly successful as compared with any STR kit currently used in the market.

In more detail, the degradation study was conducted as follows. An ultrasonic cleaning device provided the method for mechanically shearing the DNA samples into fragments. The device was filled with distilled water and set at 50° C. Volumes of 30 µL of extracted DNA, from three different samples, were sonicated for up to eight hours. Additionally, two treatment levels of DNase I provided the enzymatic method of cleaving genomic material and severely decreased the DNA sample quality. Samples underwent 10 units of DNase I treatment for 30 minutes at 37° C. and 100 units of DNase I treatment for 20 minutes at 37° C. The DNase reaction was stopped by the addition of 0.5 M EDTA, and samples were purified using the Microcon YM-30 (Millipore Corp) and eluted with TE buffer. In order to test the effectiveness of the primers on degraded DNA, Inno-Typer™ markers were used, as their amplicon lengths are no greater than 125 bp. The degraded samples were amplified under previously described conditions. A corresponding non-degraded DNA sample served as the positive control.

Example 10

Sensitivity Study of the Multiplex Reaction

All markers selected for the above multiplex reaction produced full profiles using 0.5 to 0.2 ng/µL DNA concentrations. At 0.1 ng/µL, all markers except Y5ac2305 displayed full profiles. At 0.05 ng/L, all but six markers displayed full profiles. Markers CH4-12-7012, LC3-2601 and CH1-6217 displayed partial profiles, while Yb7AD155, Y5ac2305 and Yb8NBC106 displayed no profiles. Results showed the 200 pg range to be the optimum DNA concentration for further analysis. A summary of average peak height for all markers is graphically represented in FIG. 12. A full 16 marker DNA profile was obtained from as low as 40 pg of total DNA when amplified using the InnoTyper™ 15 marker RE and Amelogenin multiplex.

The above 15 retrotransposable element (RE) marker plus Amelogenin multiplex system, referred to as InnoTyper™, was further evaluated for intra and inter RE peak height balance and sensitivity of detection. Peak heights of the 300 database samples were analyzed. Homozygous peak heights were divided by 2. Some loci had higher peak heights than others, but on the average, all peaks fell between 1000-2000 RFU when 1 ng of total DNA target sample was used. FIG. 6 demonstrates the peak height analysis of 150 database samples.

Heterozygosity percentages of the database samples were also examined. With the exception of MLS48, all markers produced heterozygous peaks above 70% heterozygosity (see FIG. 9). MLS48 was above 50%.

Heterozygous DNA profiles for each marker were diluted in 10 mM TE Buffer (pH 8.0) to obtain the following concentrations: 0.5, 0.2, 0.1 and 0.05 ng/µL. The dilutions were amplified with the following markers under previously described conditions. Table 12 shows that peak intensities were similar in magnitude for most pairs of corresponding empty and filled alleles.

TABLE 12

Primer Optimization using 2 µL primer mix.
For each genetic marker, amplicon length, peak
height ratio and peak intensity were determined.

| Markers | Alias | Reverse E primer size* (bp) | Reverse F primer size* (bp) | Peak Ratio (Empty: Filled) | Peak Intensity at 0.25 ng DNA (RFU) |
|---|---|---|---|---|---|
| CH1-6217 | 6217 | 161 | 156 | 1:2 | 1200:1200 |
| LC3-2601 | L2601 | 177 | 123 | 1:2 | 2000:800 |
| Yac52265 | 2265 | 104 | 100 | 1:1 | 1600:1200 |
| CH14-50-6236 | 6236 | 176 | 123 | 1:2.5 | 1400:1400 |
| CH4-12-7012 | 7012 | 152 | 123 | 1:1 | 1300:1700 |
| Y5ac2305 | 2305 | 58.5 | 60 | 1:1 | 1000:1300 |
| Ya5NBC51 | 51 | 119 | 118.5 | 1:1 | 1600:1600 |
| Yb7AD155 | 155 | 99 | 98.5 | 1:1 | 1500:1200 |
| CH6-28-9163 | 9163 | 112 | 112.5 | 1:1 | 1300:1300 |
| CH2-5-6240 | 6240 | 149 | 127 | 1:3 | 1800:1500 |
| Yb8NBC106 | 106 | 122 | 117.5 | 1:1 | 1200:1100 |
| Ya5ACA1736 | 1736 | 109 | 105 | 1:1 | 1250:1200 |
| HS4.69R | HS4.69R | 110 | 103 | 1:1 | 800:800 |
| Yb8AC1141 | 1141 | 60 | 56 | 1:1.5 | 1200:800 |
| Ya5-MLS48 | MLS48 | 82 | 76 | 1:1 | 1400:1300 |
| CH1-2250 | 2250 | 102 | 100 | 1:1 | 1000:1100 |
| Yb8NBC13 | 13 | 96 | 89 | 1:1 | 1000:1000 |
| TARBP1 | TARBP1 | 55 | 49 | 1.5:1 | 900:1600 |

Asterisk (*) indicates the amplicon bp sizes based on the 310 Genetic Analyzer.

Example 11

Species Specificity Study

To determine any cross-reactivity with nonhuman species, DNA from various nonhuman species was extracted and amplified with the InnoTyper™ 16 multiplex. The following species were tested with the total input DNA shown in Table 13.

TABLE 13

Types and amounts of DNA used to evaluate
species specificity of the 15 RE multiplex.

| Species | Input DNA |
|---|---|
| Human | 1 ng |
| Chimpanzee | 1 ng |
| Orangutan | 1 ng |
| Vero Monkey | 1 ng |
| Deer | 10 ng |
| Cat | 10 ng |
| Dog | 10 ng |
| Mouse | 10 ng |
| Chicken | 10 ng |
| Mosquito | 10 ng |
| *Staph* | 10 ng |

Of the species tested, only higher primate samples produced some partial DNA profiles with InnoTyper™. Some cross reactivity was observed with the nonhuman primate species tested (chimpanzee, orangutan, and vero monkey). Nonspecific artifacts were observed with some mammalian species (cat and deer), but none of the observed artifacts in the non-primate species resemble true alleles in morphology and/or size. See FIG. 15 for results. Cross reactivity of non-human primate species with the commonly used STR systems has been previously demonstrated (B. Budowle, et al., *DNA Typing Protocols: Molecular Biology and Forensic Analysis*, Natick: Eaton Publishing, 2000, pp. 41-42). An extremely low level of cross-amplification has been observed for some mobile element based genetic systems because of the ubiquitous nature of 7SL- and tRNA-related SINE families. However, this factor typically does not interfere with the assay used for human DNA. These results demonstrate that the InnoTyper™ kit is adequately species-specific for forensic use and does not yield results with non-primate samples.

While this invention has been particularly shown and described with reference to embodiments thereof, it will be understood by those skilled in the art that various changes in form and details may be made therein without departing from the spirit and scope of the invention as defined by the appended claims.

What is claimed is:

1. Primers for a multiplexed DNA analysis system, comprising:
at least 15 INNUL primer sets from SEQ ID NOS: 1-295 that are functionally operational in a multiplexed DNA analysis, each primer set including one forward primer and two reverse primers;
wherein the forward primer includes a detectable label, and each primer set corresponds to an INNUL marker including TARBP1, Ya5-MLS48, Yb8AC1141, Ya5NBC51, HS4.69 (NC000005.10), YaCA1736, Ya5-MLS18, Y5ac2305, Ya5NBC241, Yb8NBC13, CHR20-79712, Yb8NBC106, Ya5-MLS09, Ya5-MLS26, AC4027, Yc1RG148, Yb9NBC10, Ya5NBC216, Ya5ACA1766, Yb8NBC148, Ya5NBC102, SB19.12, or Yb8NBC120.

2. The primers for a multiplexed DNA analysis system of claim 1, the markers further including Amelogenin.

3. The primers for a multiplexed DNA analysis system of claim 1, the detectable label comprising 6-carboxyfluorescein (6-FAM), 6-carboxy-4',5'-dichloro-2',7'-dimethoxyfluorescein (JOE), or 6-carboxytetramethylrhodamine (TAMRA); and a label comprising at least one of 5-carboxy-X-rhodamine and 6-carboxy-X-rhodamine (ROX).

4. The primers for a multiplexed DNA analysis system of claim 1, further comprised of the forward primer including a detectable label, and each primer set corresponding to an INNUL marker including CHR20-79712, Ya5-MLS48, Ya5ACA1736, Yb8NBC106, Yb8AC1141, Ya5-MLS18, Yb8NBC13, Ya5-MLS09, TARBP1, Ya5NBC241, HS4.69 (NC000005.10), Ya5NBC51, Ya5ACA1766, or CHI-2250.

5. The primers for a multiplexed DNA analysis system of claim 4, the markers further including Amelogenin.

6. The primers for a multiplexed DNA analysis system of claim 4, the detectable label including 6-FAM, JOE, TAMRA or ROX.

7. The primers for a multiplexed DNA analysis system of claim 1, the detectable label including a fluorescent organic dye.

8. A method for genetic detection, comprising:
providing a sample to be analyzed;
selecting a plurality of Retrotransposable element (RE) markers, each selected RE marker being an INNUL marker that is associated with both a filled allele representing a filled genomic site and an empty allele representing an empty genomic site, each INNUL marker comprising a nucleic acid sequence, the nucleic acid sequence being found at a location within the genome of a target species;
providing at least 15 primer sets from SEQ ID NOS: 1-295 corresponding to each selected INNUL marker, each primer set consisting of a forward primer and two reverse primers, the two reverse primers consisting of a primer corresponding to a filled site of the INNUL marker and a primer corresponding to an empty site of the INNUL marker, at least one primer in each primer set comprising an observable label, the three primers within each primer set differing from each other in size by about 2 to about 10 base pairs;
combining the primer sets with the sample to form a reaction mixture;
amplifying the markers using the primer sets to form a mixture of amplicon products;
separating the amplicon products from the remainder of the reaction mixture and from each other on the basis of size; and
detecting and quantitating each labeled amplification product, each marker being distinguished from each other marker by a unique combination of size and observable label;
the INNUL markers comprising TARBP1, Ya5-MLS48, Yb8AC1141, Ya5NBC51, HS4.69 (NC000005.10), YaCA1736, Ya5-MLS18, Y5ac2305, Ya5NBC241, Yb8NBC13, CHR20-79712, Yb8NBC106, Ya5-MLS09, Ya5-MLS26, AC4027, Yc1RG148, Yb9NBC10, Ya5NBC216, Ya5ACA1766, Yb8NBC148, Ya5NBC102, SB19.12, or Yb8NBC120.

9. The method of claim 8, the markers further including Amelogenin.

10. The method of claim 8, the INNUL markers including CHR20-79712, Ya5-MLS48, Ya5ACA1736, Yb8NBC106, Yb8AC1141, Ya5-MLS18, Yb8NBC13, Ya5-MLS09, TARBP1, Ya5NBC241, HS4.69(NC000005.10), Ya5NBC51, or Ya5ACA1766.

11. The method of claim 10, the markers further including Amelogenin.

12. The method of claim 8, wherein separating the amplicon products from the reaction mixture includes electrophoresis.

13. The method of claim 8, the sample comprising 50 pg of DNA or more.

14. The method of claim 8, the sample comprising human DNA.

15. The method of claim 8, the amplifying the markers including the use of a real-time PCR system, the real-time PCR system including a calibration curve corresponding to each amplicon, each calibration curve being a plot of a threshold cycle number vs. the logarithm of a DNA concentration, the calibration curve providing for quantitation of the PCR amplicons.

16. The method of claim 8, further comprised of providing a determination of paternity or other human familial relationship or a human identity determination from the amplification product.

17. The method of claim 16, further comprising the use of allele insertion frequency population data to make the determination of paternity or other human familial relationship, where statistics comparing quantitation of amplicons corresponding to allegedly related family members are collected and compared to random match probabilities.

18. The method of claim 8, further comprising the use of allele insertion frequency population data to make a determination of race from a sample of human DNA, where statistics comparing quantitation of amplicons corresponding to a subject individual are collected and compared to collective quantitation figures.

19. The method of claim 8, further comprising a sample identity/genotype-related determination.

20. The method of claim 16, comprising a a human familial relationship determination.

21. The method of claim 8, wherein the sizes of the amplicons range from about 60 base pairs to about 200 base pairs.

22. The method of claim 8, wherein the INNUL markers include Ya5-MLS9, TARBP1, Yc1RG148, Ya5-MLS26, Yb8AC1141, Ya5NBC51, Yb9NBC10, HS4.69 (NC000005.10), AC4027, Ya5NBC216, Ya5ACA1766, Ya5ac2305, Yb8NBC148, Yb8NBC13, Ya5NBC102, Sb19.12, CHR20-79712, Yb8NBC106, or Yb8NBC120.

23. The method of claim 22, the markers further including Amelogenin.

24. The method of claim 8, further comprised of performing a population study wherein the combined group of selected INNUL markers provides a power of discrimination among individuals of a target species of at least 1 in 1000.

25. The method of claim 16, further comprised of providing the paternity determination via collection of statistics comparing quantitation of amplicons corresponding to mother, child and alleged father and comparing the collection of statistics to random match probabilities, the combination of the selected group of INNUL markers providing for a probability of discrimination of at least 0.999, the probability being determined by parentage analysis of 100 or fewer cases containing samples from mother, child, and alleged father.

26. The method of claim 25, further comprised of providing the paternity determination via collection of statistics comparing quantitation of amplicons corresponding to mother, child, and alleged father and comparing the collection of statistics to random match probabilities, the combination of the selected group of INNUL markers providing for a probability of discrimination of at least 0.99999, the probability being determined by parentage analysis of 100 or fewer cases containing samples from mother, child, and alleged father.

27. The method of claim 8, wherein the sample comprises 500 pg of a DNA standard.

28. A kit for multiplexed DNA analysis, the kit comprising:
 a DNA standard, the DNA standard comprising DNA at a known DNA concentration;
 at least 15 primer sets selected from SEQ IDS NO: 1-295, each primer set corresponding to a group of chromosomal INNUL markers selected for multiplexing, including for each selected chromosomal marker a forward primer, a reverse primer corresponding to a null allele and a reverse primer corresponding to a filled allele, wherein the forward primer includes a detectable label, and each primer set corresponds to an INNUL marker comprising TARBP1, Ya5-MLS48, Yb8AC1141, Ya5NBC51, HS4.69 (NC000005.10), YaCA1736, Ya5-MLS18, Y5ac2305, Ya5NBC241, Yb8NBC13, CHR20-79712, Yb8NBC106, Ya5-MLS09, Ya5-MLS26, AC4027, Yc1RG148, Yb9NBC10, Ya5NBC216, Ya5ACA1766, Yb8NBC148, Ya5NBC102, SB19.12, or Yb8NBC120; and
 instructions directing use of the kit in conjunction with one or more instruments comprising a PCR DNA analysis system, wherein the PCR system provides an amplicon corresponding to each primer set, the amplicons corresponding to each primer set being distinguishable from amplicons corresponding to each of other primer sets by unique combinations of amplicon size and observable label.

29. A kit for multiplexed DNA analysis according to claim 28, wherein the PCR DNA analysis system further provides a DNA genetic profile and the kit further comprises a software template for the determination of human identity, or paternity, or other human familial relationship.

* * * * *